(12) United States Patent
Chan et al.

(10) Patent No.: US 10,925,869 B2
(45) Date of Patent: Feb. 23, 2021

(54) COMPOSITIONS AND METHODS FOR TREATING PULMONARY VASCULAR DISEASE

(71) Applicants: UNIVERSITY OF PITTSBURGH—OF THE COMMONWEALTH SYSTEM OF HIGHER EDUCATION, Pittsburgh, PA (US); THE BRIGHAM AND WOMEN'S HOSPITAL, INC., Boston, MA (US)

(72) Inventors: Stephen Y. Chan, Pittsburgh, PA (US); Thomas Bertero, Nice (FR)

(73) Assignees: University of Pittsburgh—Of The Commonwealth System of Higher Education, Pittsburgh, PA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 16/303,369

(22) PCT Filed: May 25, 2017

(86) PCT No.: PCT/US2017/034420
§ 371 (c)(1),
(2) Date: Nov. 20, 2018

(87) PCT Pub. No.: WO2017/205595
PCT Pub. Date: Nov. 30, 2017

(65) Prior Publication Data
US 2019/0298710 A1    Oct. 3, 2019

Related U.S. Application Data
(60) Provisional application No. 62/341,848, filed on May 26, 2016.

(51) Int. Cl.

| | | |
|---|---|---|
| A61K 31/473 | (2006.01) | |
| A61P 9/12 | (2006.01) | |
| A61K 31/409 | (2006.01) | |
| A61K 31/501 | (2006.01) | |
| A61K 45/06 | (2006.01) | |
| A61P 43/00 | (2006.01) | |
| A61P 11/00 | (2006.01) | |
| A61P 9/10 | (2006.01) | |
| A61P 9/00 | (2006.01) | |
| C12N 15/113 | (2010.01) | |

(52) U.S. Cl.
CPC .......... *A61K 31/473* (2013.01); *A61K 31/409* (2013.01); *A61K 31/501* (2013.01); *A61K 45/06* (2013.01); *A61P 9/00* (2018.01); *A61P 9/10* (2018.01); *A61P 9/12* (2018.01); *A61P 11/00* (2018.01); *A61P 43/00* (2018.01); *C12N 15/113* (2013.01); *C12N 2310/14* (2013.01)

(58) Field of Classification Search
CPC .. A61K 31/409; A61K 31/501; A61K 31/473; A61K 45/06; A61P 9/12; A61P 43/00; A61P 9/00; A61P 11/00; C07D 285/135; C07D 417/06; C07D 417/14
See application file for complete search history.

(56) References Cited

U.S. PATENT DOCUMENTS

| | | | |
|---|---|---|---|
| 4,938,949 A | 7/1990 | Borch et al. | |
| 5,707,608 A | 1/1998 | Liu et al. | |
| 5,756,541 A | 5/1998 | Strong et al. | |
| 5,798,345 A | 8/1998 | Knutson et al. | |
| 8,466,283 B2 * | 6/2013 | Hentemann | A61K 31/5377 544/250 |
| 8,604,016 B2 | 12/2013 | Li et al. | |
| 8,865,718 B2 | 10/2014 | Li et al. | |
| 2009/0202540 A1 * | 8/2009 | Gant | C07F 9/65846 424/133.1 |
| 2009/0317478 A1 | 12/2009 | Han et al. | |
| 2011/0091421 A1 | 4/2011 | Mann | |
| 2016/0058759 A1 | 3/2016 | Heffernan et al. | |
| 2017/0209387 A1 | 7/2017 | Hanes et al. | |

FOREIGN PATENT DOCUMENTS

| | | |
|---|---|---|
| WO | 2015171641 A1 | 11/2015 |
| WO | 2017/095751 | 6/2017 |
| WO | 2017/205595 | 11/2017 |

OTHER PUBLICATIONS

Birsoy K, et al., "An essential role of the mitochondrial electron transport chain in cell proliferation is to enable aspartate synthesis", Cell. 2015;162(3):540-51.

Cottrill KA, et al., "Metabolic dysfunction in pulmonary hypertension: the expanding relevance of the Warburg effect.", European J. of Clin. Invest. 2013;43(8):855-65.

Cowan K, et al., "Complete reversal of fatal pulmonary hypertension in rats by a serine elastase inhibitor", Nature Medicine. 2000;6(6):698-702.

Diebold I, et al., "BMPR2 preserves mitochondrial function and DNA during reoxygenation to promote endothelial cell survival and reverse pulmonary hypertension", Cell Metabolism. 2015;21(4):596-608.

Dupont S, et al., "Role of YAP/TAZ in mechanotransduction", Nature. 2011;474(7350):179-83.

Enzo E, et al., "Aerobic glycolysis tunes YAP/TAZ transcriptional activity", EMBO J. 2015;34(10):1349-70.

(Continued)

*Primary Examiner* — My-Chau T. Tran
(74) *Attorney, Agent, or Firm* — Meunier Carlin & Curfman LLC

(57) ABSTRACT

Provided herein are compositions and methods for treating pulmonary vascular disease in a subject comprising administering to the subject a therapeutically effective amount of a YAP/TAZ inhibiting composition and/or a GLS1 inhibiting composition.

4 Claims, 31 Drawing Sheets
Specification includes a Sequence Listing.

(56) References Cited

OTHER PUBLICATIONS

Freireich et al., "Quantitative comparison of toxicity of anticancer agents in mouse, rat, hamster, dog, monkey, and man.", Cancer Chemother Reports, 1966, 50(4):219-244.
Lammers S, et al., "Mechanics and function of the pulmonary vasculature: implications for pulmonary vascular disease and right ventricular function", Compr Physiol. 2012;2(1):295-319.
Le A, et al., "Glucose-independent glutamine metabolism via TCA cycling for proliferation and survival in B cells", Cell metabolism. 2012;15(1):110-21.
Lunt Sy, et al., "Aerobic glycolysis: meeting the metabolic requirements of cell proliferation.", Annu Rev Cell Dev Biol. 2011;2:441-64.
Mathiowitz and Langer, "Polyanhydride microspheres as drug carriers I. Hot-melt microencapsulation", J Controlled Release, 1987, 5:13-22.
Mathiowitz, et al., "Novel microcapsules for delivery systems", Reactive Polymers, 1987, 6:275-283.
Mathiowitz, et al., "Polyanhydride microspheres as drug carriers. II. Microencapsulation by solvent removal", J. Appl. Polymer Sci, 1988, 35:755-774.
Mecham RP, et al., "Smooth muscle-mediated connective tissue remodeling in pulmonary hypertension", Science. 1987;237(4813):423-6.
Mo JS, et al., "Cellular energy stress induces AMPK-mediated regulation of YAP and the Hippo pathway", Nat Cell Biol. 2015;17(4):500-10.
Nave AH, et al., "Lysyl oxidases play a causal role in vascular remodeling in clinical and experimental pulmonary arterial hypertension.", Arteriosclerosis, thrombosis, and vascular biology. 2014; 34(7):1446-58.
Pan D., "The Hippo Signaling Pathway in Development and Cancer", Dev Cell. 2010;19(4):491-505.
Paulin R, et al., "The metabolic theory of pulmonary arterial hypertension.", Circ. Res. 2014;115(1):148-64.
Piao L, et al., "Cardiac glutaminolysis: a maladaptive cancer metabolism pathway in the right ventricle in pulmonary hypertension", Journal of molecular medicine. 2013;91(10):1185-97.
Sullivan LB, et al., "Supporting aspartate biosynthesis is an essential function of respiration in proliferating cells", Cell. 2015;162(3):552-63.
Wang W, et al., "AMPK modulates Hippo pathway activity to regulate energy homeostasis", Nat Cell Biol. 2015;17(4):490-9.
Zhao L, et al. "The zinc transporter ZIP12 regulates the pulmonary vascular response to chronic hypoxia", Nature. 2015;524(7565):356-60.
Zhao Y, et al., "Targeting cellular metabolism to improve cancer therapeutics", Cell Death Dis. 2013;4(e532).
Kimura et al. "The Hippo pathway mediates inhibition of vascular smooth muscle cell proliferation by cAMP," Journal of Molecular and Cellular Cardiology, Nov. 25, 2015 (Nov. 25, 2015), vol. 90, pp. 1-10.
Bertero et al. "Vascular stiffness mechanoactivates YAP/TAZ-dependent glutaminolysis to drive pulmonary hypertension." J Clin Invest. Sep. 1, 2016;126(9):3313-35.
Dumas et al., "[The paradigm of cancer in pulmonary arterial hypertension: towards anti-remodeling therapies targeting metabolic dysfunction?]" Biol Aujourdhui. 2016;210(4):171-189. See Machine Translation. English Abstract.
Bertero et al. "Matrix Remodeling Promotes Pulmonary Hypertension through Feedback Mechanoactivation of the YAP/TAZ-miR-130/301 Circuit.", vol. 13, Issue 5, Nov. 3, 2015, pp. 1016-1032.
International Search Report and Written Opinion issued for International Application No. PCT/US2017/034420, dated Aug. 16, 2017.
Kudryashova et al., American Journal of respiratory and critical medicine 2016, 194(7): 866-877.
Bram Piersma et al., Frontiers in medicine 2015, 2(3).
Communication pursuant to Rule 164(1) EPC dated Mar. 12, 2020, issued in related EP Application No. 17803564.8, 10 pages.

Acharya AP, Carstens MR, Lewis JS, Dolgova N, Xia CQ, Clare-Salzler MJ and Keselowsky BG. A cell-based microarray to investigate combinatorial effects of microparticle-encapsulated adjuvants on dendritic cell activation. J Mater Chem B. 2016;4:1672-1685.
Acharya AP, Clare-Salzler MJ and Keselowsky BG. A high-throughput microparticle microarray platform for dendritic cell-targeting vaccines. Biomaterials. 2009;30:4168-77.
Arnold JJ. Age-related macular degeneration: anti-vascular endothelial growth factor treatment. BMJ Clin Evid. 2016, 0701.
Bagshawe, K. D., et al. A cytotoxic agent can be generated selectively at cancer sites. British journal of cancer 58.6 (1988): 700-703.
Bagshawe, K. D. Towards generating cytotoxic agents at cancer sites. The First Bagshawe Lecture. Br. J. Cancer 60 (1989): 275-281.
Battelli, M. G., et al. T lymphocyte killing by a xanthine-oxidase-containing immunotoxin. Cancer Immunology, Immunotherapy 35.6 (1992): 421-425.
Bertero T, Lu Y, Annis S, Hale A, Bhat B, Saggar R, Saggar R, Wallace WD, Ross DJ, Vargas SO, Graham BB, Kumar R, Black SM, Fratz S, Fineman JR, West JD, Haley KJ, Waxman AB, Chau BN, Cottrill KA and Chan SY. Systems-level regulation of microRNA networks by miR-130/301 promotes pulmonary hypertension. J Clin Invest. 2014;124:3514-28.
Brown, Valerie I., and Mark I. Greene. Molecular and cellular mechanisms of receptor-mediated endocytosis. DNA and cell biology 10.6 (1991): 399-409.
Chan SY and Loscalzo J. Pathogenic mechanisms of pulmonary arterial hypertension. J Mol Cell Cardiol. 2008;44:14-30.
Chan SY and Rubin LJ. Metabolic dysfunction in pulmonary hypertension: From basic science to clinical practice European Respiratory Review: An Official Journal of the European Respiratory Society. 2017;26:pii: 170094.
Dieffenbach PB, Haeger CM, Coronata AMF, Choi KM, Varelas X, Tschumperlin DJ and Fredenburgh LE. Arterial stiffness induces remodeling phenotypes in pulmonary artery smooth muscle cells via YAP/TAZ-mediated repression of cyclooxygenase-2. Am J Physiol Lung Cell Mol Physiol. 2017;313:L628-L647.
Dumas SJ, Bru-Mercier G, Courboulin A, Quatredeniers M, Rucker-Martin C, Antigny F, Nakhleh MK, Ranchoux B, Gouadon E, Vinhas MC, Vocelle M, Raymond N, Dorfmuller P, Fadel E, Perros F, Humbert M and Cohen-Kaminsky S. NMDA-Type Glutamate Receptor Activation Promotes Vascular Remodeling and Pulmonary Arterial Hypertension. Circulation. 2018.
Ferrone 5 et al., eds., Noges Publications, Park Ridge, N.J., (1985) ch. 22 and pp. 303-357.
Fisher JD, Acharya AP and Little SR. Micro and nanoparticle drug delivery systems for preventing allotransplant rejection. Clin Immunol. 2015;160:24-35.
Ge J, Cui H, Xie N, Banerjee S, Guo S, Dubey S, Barnes S and Liu G. Glutaminolysis Promotes Collagen Translation and Stability via alpha-Ketoglutarate-mediated mTOR Activation and Proline Hydroxylation. Am J Respir Cell Mol Biol. 2018;58:378-390.
Godinas L, Guignabert C, Seferian A, Perros F, Bergot E, Sibille Y, Humbert M and Montani D. Tyrosine kinase inhibitors in pulmonary arterial hypertension: a double-edge sword? Semin Respir Crit Care Med. 2013;34:714-24.
Hoeper MM, Barst RJ, Bourge RC, Feldman J, Frost AE, Galie N, Gomez-Sanchez MA, Grimminger F, Grunig E, Hassoun PM, Morrell NW, Peacock AJ, Satoh T, Simonneau G, Tapson VF, Torres F, Lawrence D, Quinn DA and Ghofrani HA. Imatinib mesylate as add-on therapy for pulmonary arterial hypertension: results of the randomized IMPRES study. Circulation. 2013;127:1128-38.
Hu J, Xu Q, McTiernan C, Lai YC, Osei-Hwedieh D and Gladwin M. Novel Targets of Drug Treatment for Pulmonary Hypertension. Am J Cardiovasc Drugs. 2015;15:225-34.
Hughes, Brenda J., et al. Monoclonal antibody targeting of liposomes to mouse lung in vivo. Cancer research 49.22 (1989): 6214-6220.
Humbert M, Sitbon O and Simonneau G. Treatment of pulmonary arterial hypertension. N Engl J Med. 2004;351:1425-36.
Jain RA. The manufacturing techniques of various drug loaded biodegradable poly(lactide-co-glycolide) (PLGA) devices. Biomaterials. 2000;21:2475-90.
Litzinger and Huang, Biochimica et Biophysica Acta, 1104:179-187, (1992).

(56) References Cited

OTHER PUBLICATIONS

Liu, Lagares D, Choi Km, Stopfer L, Marinkovic A, Vrbanac V, Probst CK, Hiemer SE, Sisson TH, Horowitz JC, Rosas IO, Fredenburgh LE, Feghali-Bostwick C, Varelas X, Tager AM and Tschumperlin DJ. Mechanosignaling through YAP and TAZ drives fibroblast activation and fibrosis. Am J Physiol Lung Cell Mol Physiol. 2015;308:L344-57.

Lo Sardo F, Strano S and Blandino G. YAP and TAZ in Lung Cancer: Oncogenic Role and Clinical Targeting. Cancers (Basel). 2018; 10.

Michelakis ED, Gurtu V, Webster L, Barnes G, Watson G, Howard L, Cupitt J, Paterson I, Thompson RB, Chow K, O'Regan DP, Zhao L, Wharton J, Kiely DG, Kinnaird A, Boukouris AE, White C, Nagendran J, Freed DH, Wort SJ, Gibbs JSR and Wilkins MR. Inhibition of pyruvate dehydrogenase kinase improves pulmonary arterial hypertension in genetically susceptible patients. Sci Transl Med. 2017;9.

Pietersz, Geoffrey A., and Ian FC McKenzie. Antibody conjugates for the treatment of cancer. Immunological reviews 129.1 (1992): 57-80.

Pullamsetti SS, Savai R, Seeger W and Goncharova EA. Translational Advances in the Field of Pulmonary Hypertension. From Cancer Biology to New Pulmonary Arterial Hypertension Therapeutics. Targeting Cell Growth and Proliferation Signaling Hubs. Am J Respir Crit Care Med. 2017;195:425-437.

Ratay ML, Balmert SC, Acharya AP, Greene AC, Meyyappan T and Little SR. TRI Microspheres prevent key signs of dry eye disease in a murine, inflammatory model. Sci Rep. 2017;7:17527.

Roffler, Steven R., et al. Anti-neoplastic glucuronide prodrug treatment of human tumor cells targeted with a monoclonal antibody-enzyme conjugate. Biochemical pharmacology 42.10 (1991): 2062-2065.

Romero R, Sayin VI, Davidson SM, Bauer MR, Singh SX, LeBoeuf SE, Karakousi TR, Ellis DC, Bhutkar A, Sanchez-Rivera FJ, Subbaraj L, Martinez B, Bronson RT, Prigge JR, Schmidt EE, Thomas CJ, Goparaju C, Davies A, Dolgalev I, Heguy A, Allaj V, Poirier JT, Moreira AL, Rudin CM, Pass HI, Vander Heiden MG, Jacks T and Papagiannakopoulos T. Keap1 loss promotes KRAS-driven lung cancer and results in dependence on glutaminolysis. Nat Med. 2017;23:1362-1368.

Schneider CS, Xu Q, Boylan NJ, Chisholm J, Tang BC, Schuster BS, Henning A, Ensign LM, Lee E, Adstamongkonkul P, Simons BW, Wang SS, Gong X, Yu T, Boyle MP, Suk JS and Hanes J. Nanoparticles that do not adhere to mucus provide uniform and long-lasting drug delivery to airways following inhalation. Sci Adv. 2017;3:e1601556.

Senter, Peter D., et al. Generation of 5-fluorouracil from 5-fluorocytosine by monoclonal antibody-cytosine deaminase conjugates. Bioconjugate chemistry 2.6 (1991): 447-451.

Senter, Peter D., et al. Generation of cytotoxic agents by targeted enzymes. Bioconjugate chemistry 4.1 (1993): 3-9.

Smith et al., Antibodies in Human Diagnosis and Therapy, Haber et al., eds., Raven Press, New York (1977) pp. 365-389.

Zamanian RT, Levine DJ, Bourge RC, De Souza SA, Rosenzweig EB, Alnuaimat H, Burger C, Mathai SC, Leedom N, DeAngelis K, Lim A and De Marco T. An observational study of inhaled-treprostinil respiratory-related safety in patients with pulmonary arterial hypertension. Pulm Circ. 2016;6:329-37.

Extended EP Search Report dated Jun. 25, 2020, from related EP Application No. 17803564.8, 10 pages.

International Search Report and Written Opinion dated Feb. 14, 2019, from related International Application No. PCT/US2018/062013, 11 pages.

International Preliminary Report on Patentability dated Jun. 4, 2020, from related International Application No. PCT/US2018/062013, 7 pages.

* cited by examiner

COMPOSITIONS AND METHODS FOR TREATING PULMONARY VASCULAR DISEASE

CROSS REFERENCE TO RELATED APPLICATIONS

This application is a national stage application filed under 35 U.S.C. § 371 of PCT/US2017/034420 filed May 25, 2017, which claims the priority benefit of U.S. Provisional Patent Application Ser. No. 62/341,848 filed on May 26, 2016, the disclosures of which are expressly incorporated herein by reference.

STATEMENT OF GOVERNMENT FUNDING

This invention was made with Government support under Grant No. HL124021 awarded by the National Institutes of Health. The Government has certain rights in the invention.

BACKGROUND OF THE INVENTION

Pulmonary hypertension (PH) and its particularly severe subtype pulmonary arterial hypertension (PAH) are poorly understood vascular diseases, characterized by pro-proliferative cellular phenotypes and adverse pulmonary vascular remodeling. Alterations of the vascular extracellular matrix (ECM) are increasingly being recognized as molecular drivers of P H. Dysregulated collagen and elastin production (Mecham R P, et al., Science. 1987; 237(4813):423-6) has been observed in both end-stage and early disease (Bertero T, et al., Cell Reports. 2015; 13(5): 1016-32) and in both proximal and distal vessels (Lammers S, et al., Compr Physiol. 2012; 2(1):295-319). Pharmacologic targeting of vascular ECM can improve P H (Cowan K, et al., Nature Medicine. 2000; 6(6):698-702; Nave A H, et al. Arteriosclerosis, thrombosis, and vascular biology. 2014; 34(7):1446-58), but the processes that link ECM mechanotransduction (i.e., the processes that enable cells to sense and adapt to external mechanical forces) to the vasculature are just emerging. Two related co-transcription factors inherent to the Hippo signaling pathway, YAP (Yes Associated Protein 1) and TAZ (or WWTR1), are mechanoactivated by stiff ECM and function as central regulators of cellular proliferation and survival across multiple organs, thus modulating tissue growth and development (Dupont S, et al. Nature. 2011; 474(7350):179-83; Pan D. Dev Cell. 2010; 19(4):491-505). Recently, it was determined that pulmonary vascular stiffness activates YAP/TAZ early in disease, thereby inducing the miR-130/301 family to augment further ECM remodeling in PH in vivo (Bertero T, et al., Cell Reports. 2015; 13(5):1016-32). It was also determined that ECM stiffness drives cellular proliferation in PH, but while these functional connections are of considerable importance, their molecular mechanisms still remain unclear.

Separately, aerobic glycolysis, a chronic shift in energy production from mitochondrial oxidative phosphorylation to glycolysis, has been described as a pathogenic driver of pulmonary arterial endothelial and smooth muscle proliferation and migration in PH (as reviewed by Cottrill K A, and Chan S Y. European J. of Clin. Invest. 2013; 43(8):855-65). Prior mechanistic studies in PH related to this metabolic shift have historically relied upon hypoxic disease modeling (Paulin R, and Michelakis E D. Circ. Res. 2014; 115(1): 148-64; Zhao L, et al. Nature. 2015; 524(7565):356-60). Yet, numerous forms of PH—subtypes linked to idiopathic or secondary conditions such as predisposing genetic mutations, congenital heart disease, scleroderma, and human immunodeficiency virus (HIV) infection to name a few—are also characterized by profound metabolic dysregulation in the absence of obvious hypoxic injury. Data are only just emerging (Diebold I, et al. Cell Metabolism. 2015; 21(4): 596-608) regarding the molecular regulators of metabolic dysfunction operating independent of outright hypoxic stress in PH.

With this perspective in mind, increasing evidence suggests a central connection of YAP/TAZ activity with cellular metabolism in contexts beyond PH, including processes related to glucose consumption and aerobic glycolysis (Wang W, et al. Nat Cell Biol. 2015; 17(4):490-9; Mo J S, et al. Nat Cell Biol. 2015; 17(4):500-10; Enzo E, et al. EMBO J. 2015; 34(10):1349-70). However, increased glycolysis alone is insufficient to meet the total metabolic demands of such proliferating cells. The tricarboxylic acid (TCA) cycle also serves as a primary source of energy production via the oxidation of amino acids such as glutamine (Le A, et al. Cell metabolism. 2012; 15(1): 110-21). Continued functioning of the TCA cycle requires the replenishment of carbon intermediates. This replenishment, or anaplerosis, is accomplished via two major pathways: glutaminolysis (deamidation of glutamine via the enzyme glutaminase [GLS]) and carboxylation of pyruvate to oxaloacetate via ATP-dependent pyruvate carboxylase (PC). Specifically, glutaminolysis via GLS activity contributes to anaplerosis by allowing for mobilization of cellular energy, carbon, and nitrogen, particularly in rapidly proliferating cells (Lunt S Y, and Vander Heiden M G. Annu Rev Cell Dev Biol. 2011; 27(441-64)) and serves as a critical process in transformed cells that have switched their metabolism from oxidative phosphorylation to glycolysis in order to maintain cell growth and viability (Zhao Y, et al. Cell Death Dis. 2013; 4(e532). The particular ability of glutaminolysis (and/or pyruvate carboxylation) to support aspartate production for direct induction of proliferation has recently been reported in malignant cells (Sullivan L B, et al. Cell. 2015; 162(3):552-63; Birsoy K, et al. Cell. 2015; 162(3):540-51). In PH, dysregulation of glutaminolysis in the failing right ventricular cardiomyocyte has been observed (Piao L, et al. Journal of molecular medicine. 2013; 91(10): 1185-97). Yet, the pathogenic importance of glutamine metabolism, particularly as driven by pulmonary vascular stiffening or in the context of YAP/TAZ activation, has not been defined.

DETAILED DESCRIPTION OF THE INVENTION

Figure 1:
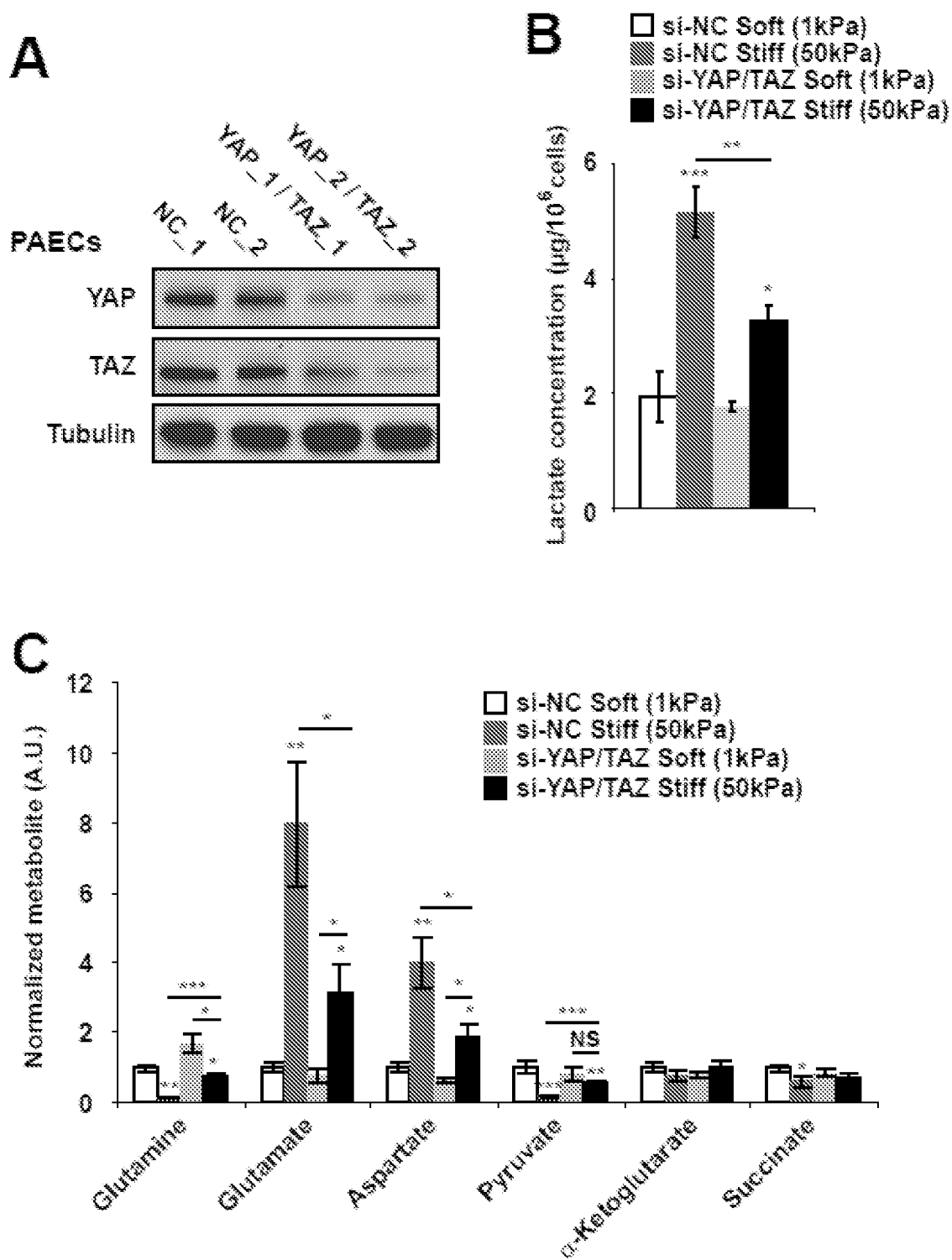
FIG. 1 (A-C) demonstrates a metabolic switch induced by ECM stiffening is coordinated by the mechanoactivation of YAP/TAZ. A) Immunoblot analysis confirmed the knockdown of YAP and TAZ by 2 independent siRNA sequences in PAECs. B-E) PAECs were cultured in soft or stiff matrix. Intracellular lactate was increased in stiff matrix, but such increase was blunted by siRNA knockdown of YAP/TAZ (B). In stiff matrix, YAP/TAZ knockdown also blunted specific metabolite alterations reflective of anaplerotic and glycolytic activity (B) as well as the lactate/pyruvate ratio (C). Data are expressed as mean±SEM (*P<0.05; P<0.01, *P<0.001). Scale bars, 20 µm. (Similar results were found in PASMCs, data not shown).

Provided herein are compositions and methods for treating pulmonary vascular disease in a subject comprising administering to the subject a therapeutically effective amount of a YAP/TAZ inhibiting composition and/or a GLS1 inhibiting composition. In some embodiments, the YAP/TAZ inhibiting composition is a verteporfin, a salt, prodrug, or derivative thereof. In other or further embodiments, the GLS1 inhibiting composition is a CB-839, a salt, prodrug, or derivative thereof. Terms used throughout this application are to be construed with ordinary and typical meaning to those of ordinary skill in the art. However, Applicant desires that the following terms be given the particular definition as defined below.

Definitions

As used in the specification and claims, the singular form "a," "an," and "the" include plural references unless the context clearly dictates otherwise. For example, the term "a cell" includes a plurality of cells, including mixtures thereof.

The term "administering" refers to an administration that is oral, topical, intravenous, cutaneous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intra-hepatic, intralesional, and intracranial injections or infusion techniques. In one embodiment, the administration is intravenous.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The term "CB-839" refers herein to a chemical composition having the chemical structure as shown below, and/or as described in U.S. Pat. No. 8,604,016 and/or U.S. Pat. No. 8,865,718.

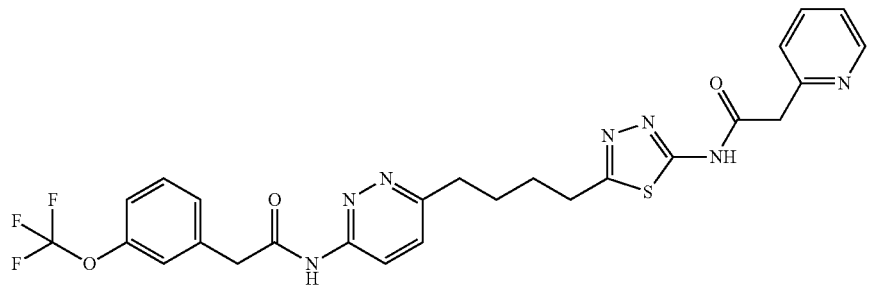 [SMILES: O=C(Cc1cccc(OC(F)(F)F)c1)Nc1ccc(CCCCc2nnc(NC(=O)Cc3ccccn3)s2)nn1]

A "composition" is intended to include a combination of active agent or agents (for example, a verteporfin and/or CB-839 composition) and another compound or composition, inert (for example, a detectable agent or label) or active, such as an adjuvant.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative."

The term "disease" refers to an abnormal condition of a part, organ, or system of a subject resulting from various causes, such as infection, inflammation, environmental factors, or genetic defect, and characterized by an identifiable group of signs, symptoms, or both. In some embodiments, the disease is a cancer.

An "effective amount" is an amount sufficient to effect beneficial or desired results. An effective amount can be administered in one or more administrations, applications or dosages.

The term "GLS1 inhibiting composition" refers herein to any composition that when administered to a subject or vascular cell, decreases or inactivates (partially or wholly) a GLS1. In some embodiments, the term "GLS1 inhibiting composition" refers herein to any composition that when administered to a subject or vascular cell and decreases or inactivates a GLS1 also treats pulmonary hypertension, pulmonary arterial hypertension and/or vascular stiffness. Non-limiting examples of GLS1 inhibiting compositions are CB-839, C-968, DON and BPTES as described herein.

The term "GLS1" refers herein to a GLS1 polypeptide also known as glutaminase and K-glutaminase in humans, is encoded by the GLS gene. The term "GLS1 polynucleotide" refers to a GLS1 encoding polynucleotide and includes a GLS gene in its entirety or a fragment thereof. In some embodiments, the GLS1 polypeptide or polynucleotide is that identified in one or more publicly available databases as follows: HGNC: 4331; Entrez Gene: 2744; Ensembl: ENSG00000115419; OMIM: 138280; and UniProtKB: O94925. In some embodiments, the GLS1 polynucleotide encodes an GLS1 polypeptide comprising the sequence of SEQ ID NO:3 (known as the KGA isoform), or a polypeptide sequence having at or greater than about 80%, at or greater than about 85%, at or greater than about 90%, at or greater than about 95%, or at or greater than about 98% homology with SEQ ID NO:3, or a polypeptide comprising a portion of SEQ ID NO:3. The GLS1 polypeptide of SEQ ID NO:3 may represent an immature or pre-processed form of mature TAZ, and accordingly, included herein are mature or processed portions of the GLS polypeptide in SEQ ID NO:3. In some examples, the GLS1 polypeptide is the GAC isoform wherein its sequence differs from SEQ ID NO:3 as follows: 551-669: VKSVINLLFA . . . TVHKNLDG-LL→HSFGPLDYES . . . YRMESLGEKS.

"Mammal" for purposes of treatment refers to any animal classified as a mammal, including human, domestic and farm animals, nonhuman primates, and zoo, sports, or pet animals, such as dogs, horses, cats, cows, etc.

A "pharmaceutical composition" is intended to include the combination of an active agent with a pharmaceutically acceptable carrier, inert or active, making the composition suitable for diagnostic or therapeutic use in vivo or ex vivo.

The term "pharmaceutically acceptable carrier" means a carrier or excipient that is useful in preparing a pharmaceutical composition that is generally safe and non-toxic, and includes a carrier that is acceptable for veterinary and/or human pharmaceutical use. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below. The pharmaceutical compositions also can include preservatives. A "pharmaceutically acceptable carrier" as used in the specification and claims includes both one and more than one such carrier.

The terms "pharmaceutically effective amount," "therapeutically effective amount," or "therapeutically effective dose" refer to the amount of a composition such as an YAP/TAZ inhibiting composition and/or a GLS1 inhibiting composition, that will elicit the biological or medical response of a tissue, system, animal, or human that is being sought by the researcher, veterinarian, medical doctor or other clinician. In some embodiments, a desired response is a treatment of a vascular disease such as pulmonary hypertension, pulmonary arterial hypertension and/or pulmonary vascular stiffness. Such treatment can be quantified by determining one or more of right ventricular systolic pressure (RVSP), right ventricular hypertrophy (Fulton index, RV/LV+S), vascular remodeling, and arteriolar muscularization.

In some instances, a desired biological or medical response is achieved following administration of multiple dosages of the composition to the subject over a period of days, weeks, or years. The terms "pharmaceutically effective amount," "therapeutically effective amount," or "therapeutically effective dose" include that amount of a composition such as a YAP/TAZ inhibiting composition and/or a GLS1 inhibiting composition, that, when administered, is sufficient to prevent development of, or alleviate to some extent, one or more of the symptoms of the disease being treated. The therapeutically effective amount will vary depending on the composition such as the a YAP/TAZ inhibiting composition and/or a GLS1 inhibiting composition, the disease and its severity, the route of administration, time of administration, rate of excretion, drug combination, judgment of the treating physician, dosage form, and the age, weight, general health, sex and/or diet of the subject to be treated. In the context of the present method, a pharmaceutically or therapeutically effective amount or dose of a YAP/TAZ inhibiting composition and/or a GLS1 inhibiting composition, includes an amount that is sufficient to treat pulmonary hypertension, pulmonary arterial hypertension and/or pulmonary vascular stiffness.

The terms "prevent," "preventing," "prevention," and grammatical variations thereof as used herein, refer to a method of partially or completely delaying or precluding the onset or recurrence of a disease and/or one or more of its attendant symptoms or barring a subject from acquiring or reacquiring a disease or reducing a subject's risk of acquiring or reacquiring a disease or one or more of its attendant symptoms.

The term "pulmonary vascular disease" is used herein to refer to pulmonary vascular hypertension and includes both pulmonary hypertension (PH) and pulmonary arterial hypertension (PAH). Pulmonary vascular disease can be caused by and/or includes pulmonary vascular stiffness.

By "salt" is meant zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002. Example of salts include, but are not limited to, mineral or organic acid salts of basic residues such as amines; and alkali or organic salts of acidic residues such as carboxylic acids.

Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, sodium, potassium, magnesium, and calcium salts of the compounds disclosed herein, and the like can be formed.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

By "prodrug" is meant compounds which, under physiological conditions, are converted into a therapeutically active compound. Prodrugs are administered in an inactive (or significantly less active) form. Once administered, the prodrug is metabolized in the body (in vivo) into the active compound. Certain compounds disclosed herein can also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they can be easier to administer than the compound, or parent drug. They can, for instance, be bioavailable by oral administration whereas the parent drug is not. The prodrug can also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Methods for selecting and preparing suitable prodrugs are provided, for example, in the following: T. Higuchi and V. Stella, "Prodrugs as Novel Delivery Systems," Vol. 14, ACS Symposium Series, 1975; H. Bundgaard, Design of Prodrugs, Elsevier, 1985; and Bioreversible Carriers in Drug Design, ed. Edward Roche, American Pharmaceutical Association and Pergamon Press, 1987. Prodrugs of the active compound can be conventional esters. Some common esters which have been utilized as prodrugs are phenyl esters, aliphatic ($C_7$-$C_8$ or $C_8$-$C_{24}$) esters, cholesterol esters, acyloxymethyl esters, carbamates, and amino acid esters. Preferably, prodrugs of the compounds disclosed herein are pharmaceutically acceptable.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more (e.g., referred to as "disubstituted," "trisubstituted," and the like) and the same or different for appropriate organic compounds. For purposes of this disclosure, the heteroatoms, such as nitrogen and oxygen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Also, as used herein "substitution" or "substituted with" is meant to encompass configurations where one substituent is fused to another substituent. For example, an aryl group substituted with an aryl group (or vice versa) can mean that one aryl group is bonded to the second aryl group via a single sigma bond and also that the two aryl groups are fused, e.g., two carbons of one alkyl group are shared with two carbons of the other aryl group.

The terms "treat," "treating," "treatment" and grammatical variations thereof as used herein, include partially or completely delaying, alleviating, mitigating or reducing the intensity of one or more attendant symptoms of a disease and/or alleviating, mitigating or impeding one or more causes of a disease. Treatments according to the invention may be applied preventively, prophylactically, palliatively or remedially. Prophylactic treatments are administered to a subject prior to onset (e.g., before obvious signs of disease), during early onset (e.g., upon initial signs and symptoms of disease), or after an established development of disease. Prophylactic administration can occur for several days to years prior to the manifestation of symptoms of an infection. In some instances, the terms "treat," "treating," "treatment" and grammatical variations thereof, include partially or completely reducing pulmonary hypertension, pulmonary arterial hypertension and/or vascular stiffness as compared with prior to treatment of the subject or as compared with the incidence of such symptom in a general or study population. The reduction can be by 5%, 10%, 20%, 30%, 40% or more.

The term "YAP/TAZ inhibiting composition" refers herein to any composition that when administered to a subject or vascular cell, decreases or inactivates a constituent in a YAP and/or a TAZ. In some embodiments, the term "YAP/TAZ inhibiting composition" refers herein to any composition that when administered to a subject or vascular cell and decreases or inactivates YAP and/or TAz results in reduced pulmonary hypertension, pulmonary arterial hypertension and/or vascular stiffness.

The term "TAZ" refers herein to a polypeptide also known as WWTR1 or WW Domain Containing Transcription Regulator Protein 1. The term "TAZ polynucleotide" refers to a TAZ/WWTR1 encoding polynucleotide and includes a TAZ/WWTR1 gene in its entirety or a fragment thereof. In some embodiments, the TAZ/WWTR1 polypeptide or polynucleotide is that identified in one or more publicly available databases as follows: HGNC: 24042; Entrez Gene: 25937; Ensembl: ENSG0000018408; OMIM: 607392; and UniProtKB: Q9GZV5. In some embodiments, the TAZ polynucleotide encodes an TAZ polypeptide comprising the sequence of SEQ ID NO: 1, or a polypeptide sequence having at or greater than about 80%, at or greater than about 85%, at or greater than about 90%, at or greater than about 95%, or at or greater than about 98% homology with SEQ ID NO: 1, or a polypeptide comprising a portion of SEQ ID NO: 1. The TAZ polypeptide of SEQ ID NO:1 may represent an immature or pre-processed form of mature TAZ, and accordingly, included herein are mature or processed portions of the TAZ polypeptide in SEQ ID NO:1.

The term "YAP" refers herein to a YAP polypeptide also known as YAP Yes-associated protein 1, or Yap65 and in humans, is encoded by the YAP1 gene. The term "YAP polynucleotide" refers to a YAP encoding polynucleotide and includes a YAP1 gene in its entirety or a fragment thereof. In some embodiments, the YAP polypeptide or polynucleotide is that identified in one or more publicly available databases as follows: HGNC: 16262; Entrez Gene: 10413; Ensembl: ENSG00000137693; OMIM: 606608; and UniProtKB: P46937. In some embodiments, the YAP polynucleotide encodes an YAP polypeptide comprising the sequence of SEQ ID NO:2, or a polypeptide sequence having at or greater than about 80%, at or greater than about 85%, at or greater than about 90%, at or greater than about 95%, or at or greater than about 98% homology with SEQ ID NO:2, or a polypeptide comprising a portion of SEQ ID NO:2. The YAP polypeptide of SEQ ID NO:2 may represent an immature or pre-processed form of mature YAP, and accordingly, included herein are mature or processed portions of the YAP polypeptide in SEQ ID NO:2.

The term "verteporfin" refers herein to a chemical composition having the chemical name 3-[(23S,24R)-14-ethenyl-5-(3-methoxy-3-oxopropyl)-22,23-bis(methoxycarbonyl)-4)-4,10,15,24-tetramethyl-25,26,27,28-tetraazahexacyclo[16.6.1.1$^{3,6}$.1$^{8,11}$.1$^{13,16}$.0$^{19,24}$]octacosa-1,3,5,7,9,11(27),12,14,16,18(25),19,21-dodecaen-9-yl]propanoic acid, having the chemical structure as shown below, and/or as described in U.S. Pat. Nos. 5,707,608, 5,798,345, and/or 5,756,541.

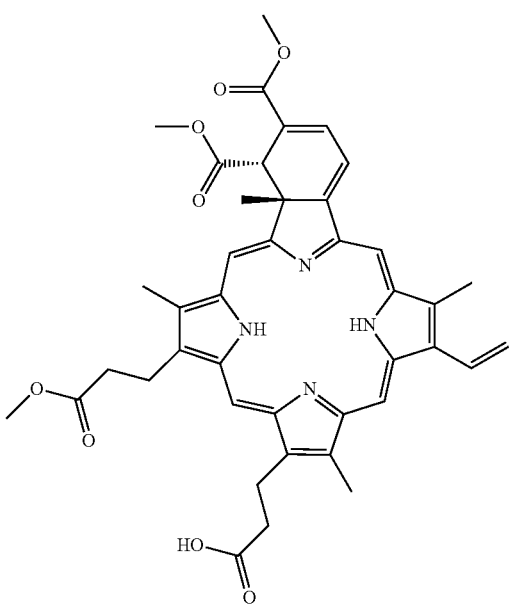 [SMILES: C=Cc1c(C)c2cc3nc(cc4[nH]c(cc5nc(cc1[nH]2)C(C)=C5CCC(=O)O)c(CCC(=O)OC)c4C)[C@@]1(C)C3=CC=C(C(=O)OC)[C@H]1C(=O)OC]

Compounds and Compositions

Disclosed herein are compounds for treating pulmonary hypertension, treating pulmonary arterial hypertension, reducing vascular stiffness and/or inhibiting a YAP/TAZ- and/or a GLS1-mediated pathway. The compounds for treating pulmonary hypertension, treating pulmonary arterial hypertension, reducing vascular stiffness and/or inhibiting a YAP/TAZ- and/or a GLS1-mediated pathway can be a verteporfin, a CB-839, or a prodrug, a derivative, a salt, a solvate thereof, or combinations thereof. Pharmaceutical compositions containing one or more of the compounds described herein can be prepared using a pharmaceutically acceptable carrier. A "pharmaceutically acceptable" carrier is one that is suitable for use with humans and/or animals without undue adverse side effects (such as toxicity, irritation, and allergic response) commensurate with a reasonable benefit/risk ratio. The carrier is all components present in the pharmaceutical composition other than the active ingredient or ingredients. Carrier can include, but is not limited to, diluents, binders, lubricants, disintegrators, pH modifying agents, preservatives, antioxidants, solubility enhancers, stabilizers, surfactants, and coating compositions.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and can include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which can include, by way of example, oxidative reactions.

Surfactants can be anionic, cationic, amphoteric or nonionic surface active agents. Suitable anionic surfactants can include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, POLOXAMER™ 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The coating compositions can include plasticizers, pigments, colorants, stabilizing agents, and glidants. Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT™ (Roth Pharma, Westerstadt, Germany), zein, shellac, and polysaccharides.

The compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, prodrugs, or derivatives thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Compounds and compositions disclosed herein, including pharmaceutically acceptable salts, hydrates, prodrugs, or derivatives thereof, can be administered in controlled release formulations. Such compositions can influence the physical state, stability, rate of in vivo release, and rate of in vivo clearance of the present proteins and derivatives. See, e.g., Remington's Pharmaceutical Sciences, 21st Ed. (2005, Lippincott, Williams & Wilins, Baltimore, Md. 21201) pages 889-964 and "Pharmaceutical dosage form tablets", eds. Liberman et al. (New York, Marcel Dekker, Inc., 1989). These references provide information on carriers, materials, equipment and process for preparing tablets and capsules and delayed release dosage forms of tablets, capsules, and granules.

Controlled release compositions can be made for short or long term release systemically following administration of the composition. The compositions can be prepared in liquid form, in dried powder (e.g., lyophilized) form, or as a polymeric device (rod, cylinder, film, disk). The matrix can be in the form of microparticles such as microspheres, where the active agent is dispersed within a solid polymeric matrix or microcapsules, where the core is of a different material than the polymeric shell, and the active agent is dispersed or suspended in the core, which can be liquid or solid in nature. Alternatively, the polymer can be cast as a thin slab or film, ranging from nanometers to four centimeters, a powder produced by grinding or other standard techniques, or even a gel such as a hydrogel.

Either non-biodegradable or biodegradable matrices can be used for delivery of the compounds disclosed, although biodegradable matrices are preferred. These can be natural or synthetic polymers. The polymer is selected based on the period over which release is desired. In some cases linear release can be most useful, although in others a pulse release or "bulk release" can provide more effective results. The polymer can be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J Controlled Release*, 1987, 5:13-22; Mathiowitz, et al., *Reactive Polymers*, 1987, 6:275-283; and Mathiowitz, et al., *J. Appl. Polymer Sci*, 1988, 35:755-774.

Compounds and compositions disclosed herein, including pharmaceutically acceptable salts, hydrates, prodrugs, or derivatives thereof, can be incorporated into an inert matrix which permits release by either diffusion or leaching mechanisms, e.g., films or gums. Slowly disintegrating matrices can also be incorporated into the formulation. Another form of a controlled release is one in which the drug is enclosed in a semipermeable membrane which allows water to enter and push drug out through a single small opening due to osmotic effects. For oral formulations, the location of release can be the stomach, the small intestine (the duodenum, the jejunem, or the ileum), or the large intestine. Preferably, the release will avoid the deleterious effects of the stomach environment, either by protection of the active agent (or derivative) or by release of the active agent beyond the stomach environment, such as in the intestine. To ensure full gastric resistance an enteric coating (i.e., impermeable to at least pH 5.0) is essential. These coatings can be used as mixed films or as capsules such as those available from Banner Pharmacaps.

Methods

Also provided herein are methods of treating vascular disease, pulmonary hypertension, and/or pulmonary arterial hypertension, reducing vascular stiffness, and/or inhibiting a YAP/TAZ- and/or GLS1-mediated pathway in a subject in need of such treatment. The methods can include administering to a subject a therapeutically effective amount of one or more of the compounds or compositions described herein. In some examples, the method includes administering a therapeutically effective amount of a verteporfin or a pharmaceutical composition comprising the same, to a subject. In some examples, the method can include administering a therapeutically effective amount of a verteporfin, a salt, prodrug, or derivative thereof, or a combination thereof to a subject. In other or further examples, the method includes administering a therapeutically effective amount of a CB-839 or a pharmaceutical composition comprising the same, to a subject. In some examples, the method can include administering a therapeutically effective amount of a CB-839. Accordingly, included herein are methods of administering a therapeutically effective amount of a verteporfin and a CB-839, which therapeutic effectiveness can be due to the administration of both compositions.

These methods reflect the novel results provided herein demonstrating that there is a crucial connection of YAP/TAZ mechanoactivation to the glutaminolytic enzyme GLS1 required to coordinate the cellular energetic needs for proliferation in the setting of aerobic glycolysis. Such molecular insights advance the paradigm of vascular stiffness beyond merely the study of hemodynamic effects on vascular compliance, but rather as a specific metabolic cause of vascular remodeling and PH development. These results also alter the fundamental understanding of the dysregulated metabolic axis in PH itself beyond direct hypoxic injury by revealing both glutamine metabolism and aerobic glycolysis as integrally linked through a shared hierarchy of regulation via YAP/TAZ. Finally, by placing glutaminolysis as a central mechanism of how the extracellular environment dictates pulmonary vascular dysfunction, these results form the basis for developing novel therapeutics, or even more likely, re-purposing in PH already approved medications, that target the YAP1-GLS1 axis.

Recent work has advanced the concept that vascular stiffening in PH is an early and potent pathogenic trigger in PH. Yet, beyond the association with vascular proliferation, a detailed characterization is missing of the downstream molecular pathways affected by such mechanical stimuli. Alternatively, while previous studies have demonstrated profound mitochondrial and metabolic dysfunction in PH, the complex initiating triggers of such metabolic events have been elusive, particularly those beyond the direct consequences of hypoxic injury. To date, such metabolic phenotypes in part are known to be driven by hypoxia, leading to a glycolytic switch via pyruvate dehydrogenase kinase (PDK)-mediated inhibition of pyruvate dehydrogenase. More recent data have linked non-coding RNAs, loss of function in the bone morphogenetic protein receptor type 2 (BMPR2), and sirtuin 3 deficiency to global mitochondrial dysfunction in PH. Here, the identification of glutaminolysis as a mechanoactivated process and co-regulated with aerobic glycolysis advances the understanding of the regulatory hierarchy seen in the metabolic reprogramming in PH. Such an interface between stiffness and metabolism draws parallels to related reprogramming events proposed in tumors in relation to matrix remodeling. By its direct causative relation to metabolic dysregulation, it also reinforces the paradigm of vascular stiffness as an initiating pathogenic trigger of this disease rather than merely an end-stage feature.

Elucidation of a functional connection linking vessel stiffness to glutaminolysis and proliferation also provides fundamental insight into the interplay between cellular proliferation, migration, and apoptosis among multiple vascular cell types during the initiation and development of PH. As described in other biological contexts, increased glutaminolysis and anaplerosis in response to stiff matrix and YAP/TAZ activation answers a key metabolic need to sustain the hyperproliferative state, particularly in PASMCs and thus drive pathologic vascular remodeling in PH. Beyond PASMCs, a YAP/TAZ-microRNA-130/301 feedback loop was recently described whereby matrix stiffening is augmented and spreads through pulmonary vasculature and perhaps even pulmonary parenchyma via mechanoactivation of naïve fibroblasts that contact adjacent stiffened matrix. In light of the current findings implicating YAP/TAZ activation with glutaminolysis, it is possible that glutaminolysis and anaplerosis in fibroblasts are inherently linked to the control of matrix stiffening and remodeling.

On the other hand, the role of stiffness and glutaminolysis may be more complex in controlling the still incompletely described dysfunction of PAECs in PH. To date, it is thought that PAEC apoptosis plays an initiating, early role in triggering PH pathogenesis. Initial EC apoptosis then gives rise to a separate population of hyperproliferative and pathogenic PAECs that are crucial to disease progression. Such a spatio-temporal balance of PAEC apoptosis and proliferation was originally described by Voelkel and colleagues and others since then. The findings are consistent with this kinetic model of PAEC apoptosis, indicating that the initiating wave of injury and apoptosis are followed closely thereafter by YAP/TAZ-GLS1 activation and glutaminolyis, thus promoting proliferation of PAECs thereafter. Notably, this model does not rule out continued PAEC apoptosis even at later time points after PH initiation, as reported by others, particularly in situations of more slowly progressive PH. However, these apoptotic events have to be occurring in cells other than the proliferative component—a component that we find is more prevalent in more severe models of PH when overt vascular stiffness and glutaminolysis are even more evident. Such proliferation may reflect increased PAEC turnover at earlier stages of PH (represented by D3-D7 post-monocrotaline injection in rats, data not shown) where a balance of apoptosis and proliferation was more evident in the PAEC population. However, during later stages of severe PH when YAP1 and GLS1 up-regulation was persistent, the predominance of PAEC proliferation over apoptosis was unambiguous. This finding correlates with observations of human plexiform lesions in PAH (data not shown), where YAP up-regulation and glutaminolytic processes accompany obvious overgrowth of PAEC-like cells. Even in settings where the endothelial layer is not obviously overgrown, it is possible that hyperproliferative, anti-apoptotic PAECs are re-programmed for endothelial-to-mesenchymal transition—a process that has now been directly connected to PH pathogenesis and where further proliferation would allow for endothelial cells to feed into medial layer (rather than simply intimal) hyperplasia. Finally, correlating with increased proliferative capacity in PAECs, these findings also revealed a pro-migratory phenotype promoted by matrix stiffness and the YAP-GLS1 axis (data not shown). A disorder of proliferation and migration has been observed in human plexiform lesions, and more recent studies of hyperproliferative PAECs in PH have described an accompanying migratory phenotype. Such disordered migration may contribute to abnormal angiogenesis in PH—which in some cases has been linked a pro-angiogenic and pathogenic remodeling of the pulmonary arteriole and in other cases has been linked to a deficiency of angiogenesis and thus a pruning of the entire pulmonary vascular tree. Consequently, the results described herein place vessel stiffness, the YAP/TAZ-GLS1 axis, and glutaminolysis at central points in PH pathogenesis, affecting multiple pulmonary vascular cell phenotypes in a precisely timed and stage-specific manner.

The mechanoactivation of YAP/TAZ as a central mediator of glutaminolysis also advances the understanding of the intricate control of metabolism by Hippo signaling, in general. Notably, the data indicated that both YAP and TAZ together, but not alone, are necessary for GLS1, LDHA, and PC expression (FIG. 2C-E), at least in conditions of endogenous response to matrix stiffening. Yet, because overexpression of YAP1 alone can increase these downstream genes (FIG. 2F-H), it is concluded that YAP1 is sufficient for this phenotype and may hold some redundant functions in regulating glutaminolysis. This redundancy, however, is not obvious when TAZ is also up-regulated during matrix stiffening, thus suggesting the activity of YAP with TAZ represents the preferential partnership to allow for glutaminolysis induction under stiff conditions. Furthermore, previous studies have implicated cellular energy status as potent regulators of YAP activity either through AMP-kinase activation or direct promotion of transcriptional activity of YAP/TAZ via aerobic glycolysis. Mevalonate metabolism can also activate Rho GTPase which, in turn, de-phosphorylates YAP/TAZ. Notably, a connection between YAP activity and glutamine synthase (GS) has been reported specifically in the liver where GS expression can predominate. Yet, in other tissue compartments such as the pulmonary vasculature, complementary to the notion that YAP/TAZ respond to metabolic signals, these findings more directly define these factors as mechanical sensors to reprogram glycolytic and glutaminolytic pathways and coordinate with cellular proliferation. This reciprocity among YAP/TAZ with upstream and downstream metabolic cues suggests an adjustable, feedback-driven property inherent to this pathway and may be partly responsible for individualized "tuning" of the metabolic program, depending upon burden of ECM remodelling, PH subtype, severity, or temporal stage. Furthermore, given the expanding repertoire of known environmental cues that affect YAP/TAZ, it is likely that the metabolic actions of Hippo signaling extend to an even wider sphere of influence than vascular stiffness or PH alone. Certainly, in the contexts of organ development and tumorigenesis, it is tempting to speculate on the master regulatory role of Hippo signaling on glutaminolysis and glycolysis as a primary mechanism to balance proliferative capacity with efficient energy production.

The identification of glutaminolysis as a crucial mediator of the PH pathophenotype shifts attention to essential regulatory metabolic checkpoints beyond aerobic glycolysis in this disease. The identification of GLS1 as a nodal control point emphasizes glutaminolysis and anaplerosis as key molecular determinants in general underlying the overarching similarity between the pathogenesis of PH and cancer. These findings may also suggest that other aspects of glutamine handling, such as glutamine transporters, may be involved. Moreover, beyond GLS1, two additional enzymes—LDHA and pyruvate carboxylase—were identified here as linked checkpoints in stiffness-mediated alterations of glycolysis and anaplerosis (FIG. 1), indicating an even broader level of control over the metabolic landscape in PH that awaits future characterization.

The mechanistic connection of the YAP/TAZ-GLS axis to HIV-PAH also contributes needed insight into the pathogenesis of this enigmatic form of PH. There exists an increased prevalence of PAH in HIV-infected individuals, but little is known about the molecular pathogenesis of HIV-PAH. By establishing the actions of YAP/TAZ and GLS in primate and human models of PAH secondary to HIV or SIV infection, these findings provide long-awaited evidence that, beyond histopathologic associations, the molecular and cellular pathophenotypes active in this subtype of PAH overlap with other PAH forms and may be amenable to treatment with similarly targeted therapeutics.

Figure 4:
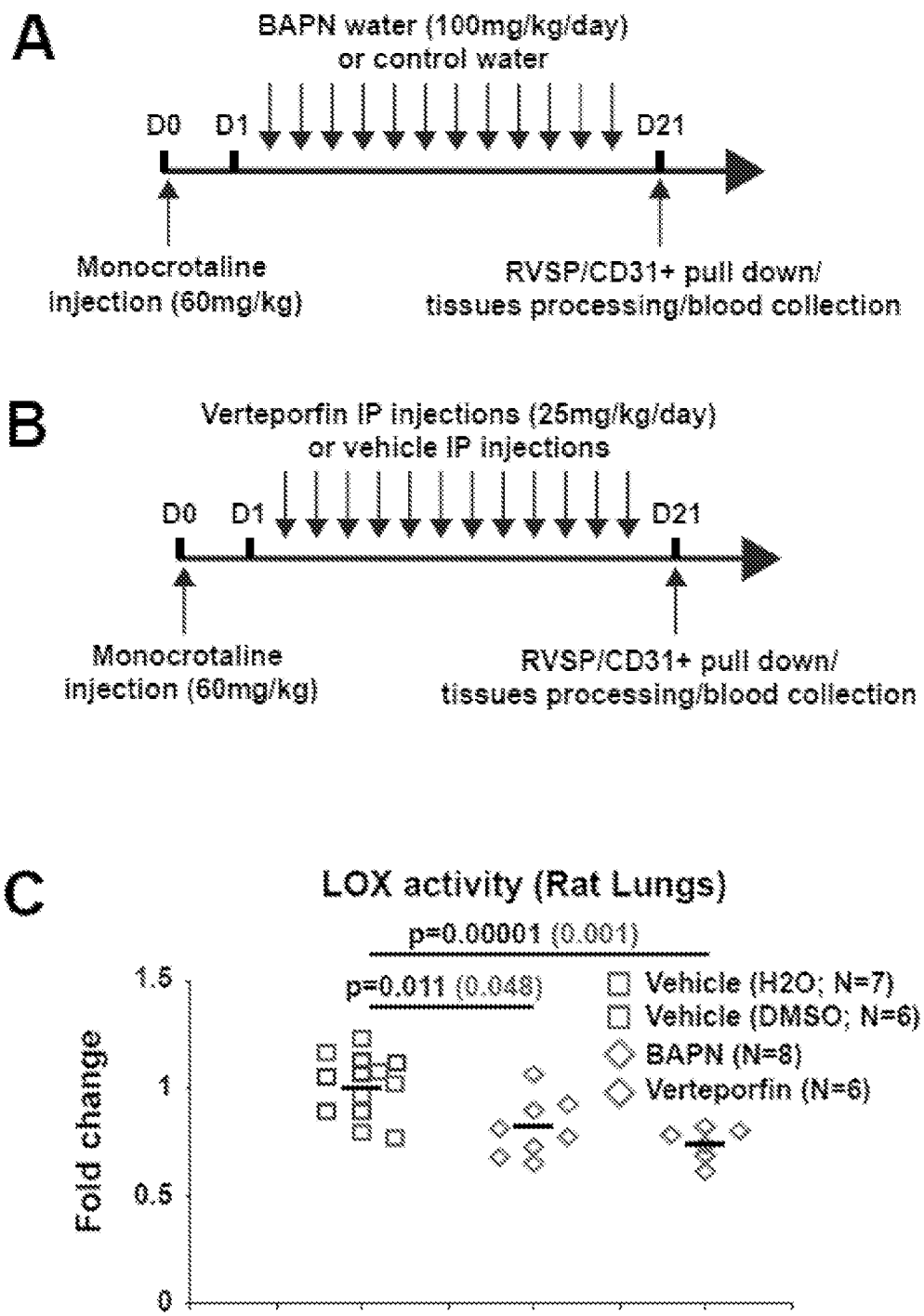
FIG. 4 (A-I) demonstrates manipulation of mechanotransduction in monocrotaline-exposed rats affects glutaminolysis decreased pulmonary vascular proliferation and prevents PAH. A-B) Following monocrotaline exposure, rats were treated either with daily BAPN or vehicle (A) or either with daily intraperitoneal injections of vehicle or verteporfin (B). C) Both BAPN and Verteporfin decreased LOX activity in lungs of monocrotaline-exposed rats. D) Atomic force microscopy revealed decreased pulmonary arteriolar (<100 mm) stiffness in BAPN and Verteporfin treated rats. Black lines denote median; symbols denote individual PA measurements. E-F) RT-qPCR of PAH CD31+ cells revealed a decrease of CTGF and CYR61 two YAP/TAZ target genes as well as a decrease of GLS expression (E) and activity (F) in BAPN and Verteporfin treated rats. G) Hematoxyline/Eosin coloration and co-immunofluorescence microscopy revealed a decreased of vessel thickness and muscularization as well as a decreased of YAP1+ cells, a decreased of GLS1 vascular intensity, and a decreased of CD31/PCNA and α-SMA/PCNA double-positive cells in BAPN and Verteporfin treated rats compared to vehicles rats. H-I) Verteporfin and in a lower extent BAPN ameliorated PAH severity, as quantified by RVSP (I). In all panels, mean expression in control groups was assigned a fold change of 1, to which relevant samples were compared. $*P<0.05$; $P<0.01$, $*P<0.001$. Scale bars, 50 µm.
Figure 4:
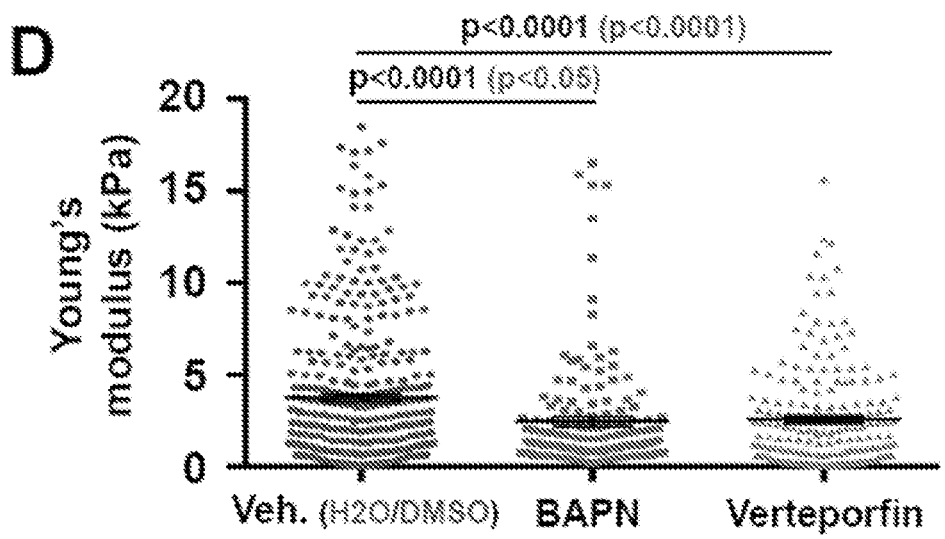
Figure 4:
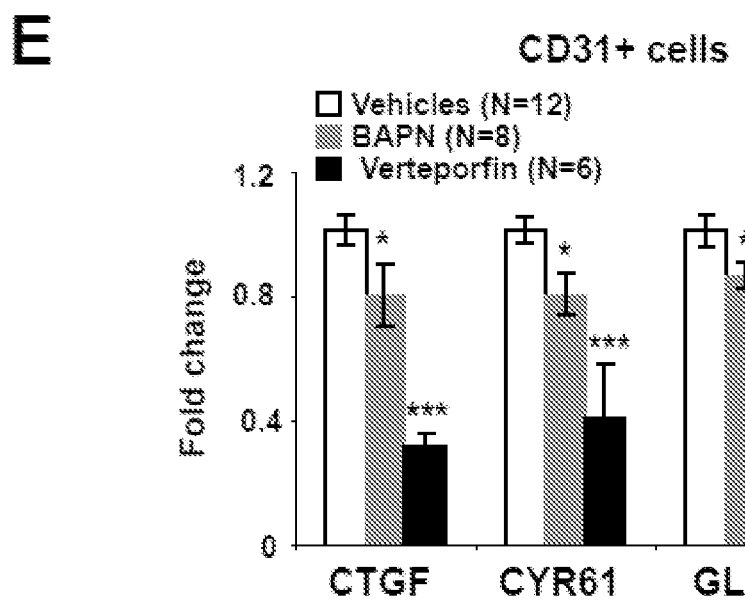
Figure 4:
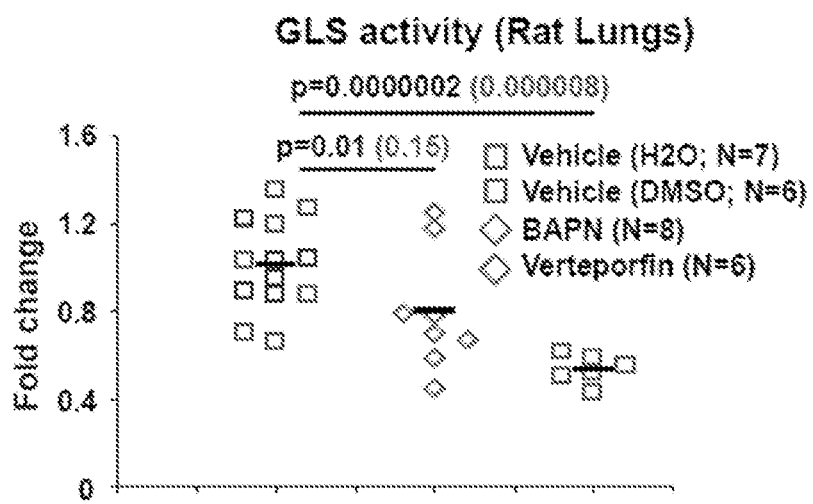
Figure 4:
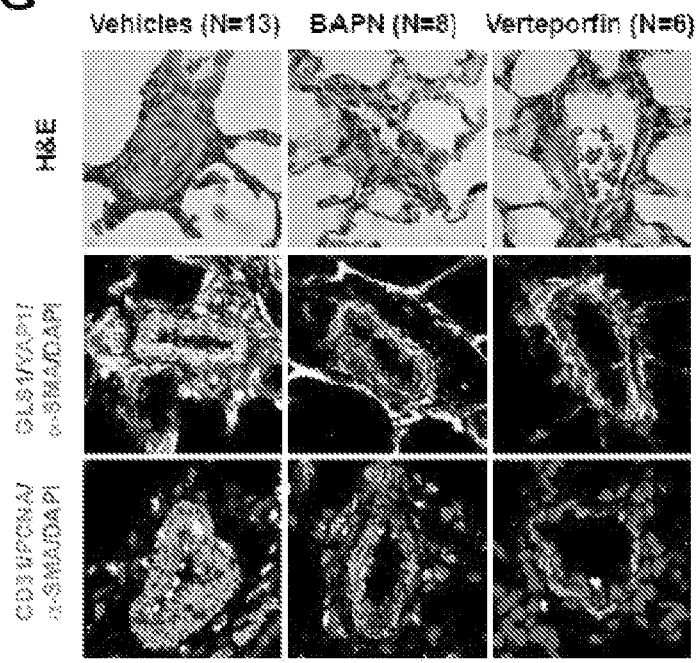
Figure 4:
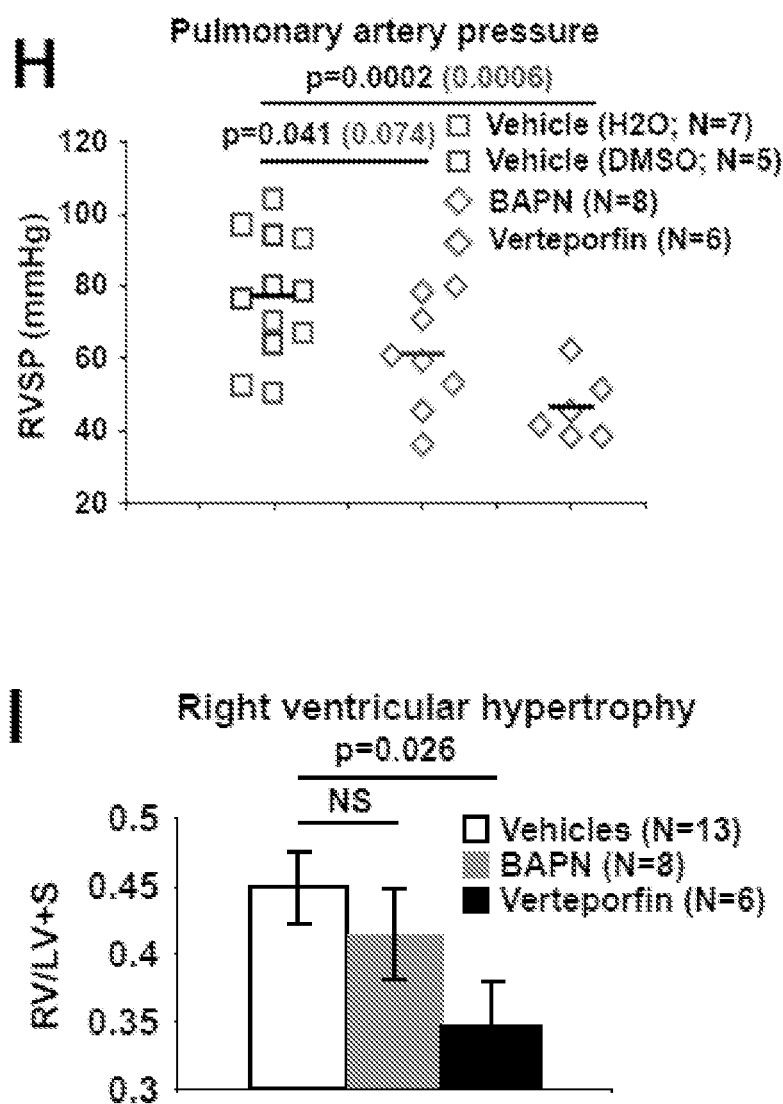

Finally, the identification of the mechanoactivation of glutaminolysis in PH sets the stage to develop novel clinical management strategies in PH. Thus far, pharmacologic inhibition of PDK by dichloroacetate has been the most prominent metabolic targeting strategy under clinical investigation for PH. The results described herein demonstrate that a range of functionally connected targets related to matrix remodeling and glutaminolysis show promise for further therapeutic development in PH. The improvement of hemodynamic and histologic indices of PH in monocrotaline-exposed rats with BAPN (FIG. 4) reinforces the importance of collagen crosslinking and ECM remodeling in PH pathogenesis and is consistent with prior studies inhibiting Lox (lysyl oxidase) in chronic hypoxic PH. However, therapeutic use of a specific Lox inhibitor alone may suffer from modest efficacy (i.e., improving right ventricular remodelling, FIG. 4), potentially due to the importance of several other lysyl oxidases that may show redundant or complementary function. Yet, when coupled with targeting of the downstream YAP1-GLS1 metabolic axis, an additive or perhaps synergistic therapeutic benefit may emerge in inhibiting pulmonary vascular proliferation and remodeling. This may be particularly evident with YAP1, given the multiple emerging beneficial effects even beyond metabolism of altering HIPPO signaling in the pulmonary vasculature and the robust improvement of severe rodent PH when using the YAP1 inhibitor verteporfin alone (FIG. 4).

The compounds or compositions described can be administered initially in a suitable dosage that can be adjusted as required, depending on the clinical response. Preliminary doses, for example, as determined in animal tests, and the scaling of dosages for human administration is performed according to art-accepted practices. For example, methods for the extrapolation of effective dosages in mice, and other animals, to humans are known to the art; for example, see U.S. Pat. No. 4,938,949, Freireich et al., *Cancer Chemother Reports,* 1966, 50(4):219-244. Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. In some examples compositions that exhibit large therapeutic indices are used.

The therapeutically effective dose can be estimated initially from cell culture assays. A dose can be formulated in animal models to achieve a circulating plasma concentration range that includes the $IC_{50}$ (i.e., the concentration of the therapeutic compound which achieves a half-maximal inhibition of symptoms) as determined in cell culture assays or animal models. Levels in plasma can be measured, for example, by ELISA or HPLC. The effects of any particular dosage can be monitored by a suitable bioassay. Examples of dosages are: about $0.1 \times IC_{50}$, about $0.5 \times IC_{50}$, about $1 \times IC_{50}$, about $5 \times IC_{50}$, $10 \times IC_{50}$, about $50 \times IC_{50}$, and about $100 \times IC_{50}$.

Examples of therapeutically effective amount of compounds described herein are from about 1 μg/kg to about 40 mg/kg, depending on the compounds and the severity of the symptoms. The appropriate therapeutically effective doses can be selected by a treating clinician and in some examples range approximately from about 1 μg/kg to about 40 mg/kg, from about 1 μg/kg to about 25 mg/kg, from about 1 μg/kg to about 10 mg/kg, from about 10 μg/kg to about 1 mg/kg, from about 10 μg/kg to about 100 μg/kg, or from about 100 μg/kg to about 1 mg/kg. Additionally, certain specific dosages in animals are indicated in the Examples.

For verteporfin, an effective amount can range from about 1 mg/kg to about 50 mg/kg (e.g., from about 2.5 mg/kg to about 30 mg/kg or from about 10 mg/kg to about 25 mg/kg). Effective doses will also vary, as recognized by those skilled in the art, dependent on route of administration, excipient usage, and the possibility of co-usage with other therapeutic treatments including use of other therapeutic agents. In some examples, the therapeutically effective amount of verteporfin, a salt, prodrug, or derivative thereof, or a combination thereof is about 10-25 mg/kg per day.

For C-968 and CB839 an effective amount can range from about 1 mg/kg to about 30 mg/kg (e.g., from about 2.5 mg/kg to about 20 mg/kg or from about 5 mg/kg to about 15 mg/kg). Effective doses will also vary, as recognized by those skilled in the art, dependent on route of administration, excipient usage, and the possibility of co-usage with other therapeutic treatments including use of other therapeutic agents. In some examples, the therapeutically effective amount of C-968 or CB839, a salt, prodrug, or derivative thereof, or a combination thereof is about 10 mg/kg per day.

The dosage can be determined by a physician and adjusted, as necessary, to suit observed effects of the treatment. The compositions can be given as a bolus dose, to maximize the circulating levels for the greatest length of time after the dose. Continuous infusion can also be used after the bolus dose. In some examples, the compound or composition can be administered in separate administrations of 2, 3, 4, or 6 equal doses. For example, the about 25 mg/kg per day can be administered in separate administrations of 2, 3, 4, or 6 equal doses. In another example, the about 10 mg/kg per day can be administered in separate administrations of 2, 3, 4, or 6 equal doses.

The compounds or compositions described herein are suitable for short term and long term use. "Short-term use", as used herein, can refer to the administration to a patient of no more than about 20 doses of the compounds or compositions disclosed. Accordingly, the term "long-term use", as used herein, can refer to the administration to a patient of more than about 20 doses of the compounds or compositions disclosed.

The compounds and compositions described can be administered alone or in combination with one or more additional therapeutic agents, such as an analgesic agent used in the treatment of nociception, inflammatory, functional, or neuropathic pain or an anti-inflammatory agent. The one or more additional therapeutic agent may or may not produce a therapeutic effect when administered on its own, but results in such an effect (e.g., pain reduction) when administered with any of the compound or composition disclosed.

The one or more additional therapeutic agents and the compounds and compositions described herein can be administered in any order, including simultaneous administration, as well as temporally spaced order of up to several days apart. The administration of the one or more additional agents and the compounds and compositions described herein can be by the same or different routes. In some examples, the one or more additional agents can be combined with the compounds and compositions described herein.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. All patents, patent applications, and publications referenced herein are incorporated by reference in their entirety for all purposes.

EXAMPLES

Example 1

Experimental Procedures

Cell Culture and Reagents

HEK293T cells (American Type Culture Collection) were cultivated in DMEM containing 10% fetal bovine serum (FBS). Primary human pulmonary arterial endothelial cells (PAECs) were grown in EGM-2 cell culture media (Lonza), and experiments were performed at passages 3 to 6. Primary human pulmonary arterial smooth muscle cells (PASMCs) were cultured in SmGM-2 cell culture media (Lonza), and experiments were performed at passages 3 to 9. Inhibitors of GLS1 (2, 3): BPTES (Bis-2-(5-phenylacetamido-1,3,4-thiadiazol-2-yl)ethyl sulphide), DON (6-Diazo-5-oxo-L-norleucine), and C968 (Glutaminase Inhibitor, Compound 968, 5-(3-Bromo-4-(dimethylamino)phenyl)-2,2-dimethyl-2,3,5,6-tetrahydrobenzo[a]phenanthridin-4(1H)-one) were purchased from Sigma-Aldrich and used at concentration of 10 M, 5 M and 10 M respectively. Glutamate was purchased from Sigma Aldrich and used at concentration of 2 mM. Aspartate was purchased from Sigma Aldrich and used at concentration of 10 mM.

Oligonucleotides and Transfection

On Target Plus siRNAs for YAP (J-012200-07 and J-012200-05,), TAZ (WWTR1; J-016083-05 and J-016083-06), GLS (J-004548-09, si-GLS_1; J-004548-10, si-GLS_2), and scrambled control D-001810-01 and D-001810-02) were purchased from ThermoScientific/Dharmacon. siRNA experiments are representative of results obtain with either siYAP_1/TAZ_1 or siYAP_2/TAZ_2. PAECs, and PASMCs were plated in collagen-coated plastic (50 μg/mL) and transfected 24 h later at 70-80% confluence using siRNA (25 nM) and Lipofectamine 2000 reagent (Life Technologies), according to the manufacturers' instructions. Eight hours after transfection, cells were trypsinized and re-plated on hydrogel.

Plasmids

The YAP1 coding sequence was purchased (Addgene; Plasmid #18881) and sub-cloned in the pCDH-CMV-MCS-EF1-copGFP (System Biosciences) using EcoRI and NotI restriction sites. The lentiviral parent vector expressing GFP was used as a control. Stable expression of these constructs in PAECs, and PASMCs was achieved by lentiviral transduction. All cloned plasmids were confirmed by DNA sequencing.

Lentivirus Production

HEK293T cells were transfected using Lipofectamine 2000 (Life Technologies) with lentiviral plasmids along with packaging plasmids (pPACK, System Biosciences), according to the manufacturer's instructions. Virus was harvested, sterile filtered (0.45 µm), and utilized for subsequent infection of PAECs, and PASMCs (24-48 hours incubation) for gene transduction.

Messenger RNA Extraction

Cells were homogenized in 1 ml of QiaZol reagent (Qiagen). Total RNA content, was extracted using the miRNeasy kit (Qiagen) according to the manufacturer's instructions. Total RNA concentration was determined using a ND-1000 micro-spectrophotometer (NanoDrop Technologies).

Quantitative RT-PCR of Messenger RNAs

Messenger RNAs were reverse transcribed using the Multiscript RT kit (Life Technologies) to generate cDNA. cDNA was amplified via fluorescently labeled Taqman primer sets using an Applied Biosystems 7900HT Fast Real Time PCR device. To specifically determine the relative expression of the two GLS1 isoforms KGA and GAC, TaqMan gene expression assays Hs01014019_m1 and Hs01022166_m1 were used respectively. Fold-change of RNA species was calculated using the formula ($2^{-\Delta\Delta Ct}$), normalized to RPLP0 expression.

ChIP-qPCR

PAECs were cultivated on plastic for 48 h. Cells were dual cross-linked with 2 mM disuccinimidyl glutarate (DSG) for 45 minutes and then in 1% paraformaldehyde for 15 minutes at room temperature. Fixed cells were lysed in 10 ml of Lysis Buffer 1 [50 mM HEPES (pH 7.5), 140 mM NaCl, 1 mM EDTA, 0.1% IGEPAL 630 (Sigma Aldrich)], containing 0.05% Triton X100, 2.5% glycerol and supplemented with 1× protease inhibitor cocktail (Roche) for 10 minutes on ice, followed by incubation in Buffer 2 [0.1 M Tris HCl (pH 8) and 200 mM NaCl with protease inhibitors] for 15 minutes at room temperature. Chromatin was sonicated at 30% of amplitude for 10 minutes (10 cycles of 1 minute). The samples were centrifuged (2×14,000 g for 5 minutes each), and soluble chromatin was transferred to a fresh tube. Crosslinked DNA after sonication was precipitated with 5 g of anti-YAP1 antibody (sc-15407X, Santa Cruz Biotechnology) or non-immune rabbit IgG (ab27472, Abcam) overnight at 4° C. Chromatin/antibody complex was pulled down with PureProteome™ Protein G Magnetic Beads (Millipore) and washed in the low- and high-salt buffers. After cross-linking reversion (65° C. for 4 hours) and Proteinase K treatment, chromatin was purified by phenol-chloroform extraction and ethanol precipitation. Precipitated DNA was analyzed by qPCR using primers generated for predicted TEAD binding sites or a non-relevant genomic region (Control).

Microarrays

PAECs were transfected with a siRNA control (si-NC) or a siRNA against GLS1 (si-GLS_1) and cultivated on soft hydrogel (1 kPa) or stiff hydrogel (50 kPa). Forty-eight hours post-transfection, cells were lysed, and RNA was extracted for hybridization on Affymetrix microarrays (HuGene 2.0 ST), according to the manufacturer's instruction. Briefly, total RNA was extracted from PAECs cells using the miRNeasy kit (Qiagen) according to the manufacturer's instructions. Total RNA concentration was determined using an ND-1000 micro-spectrophotometer (NanoDrop Technologies). Biotinylated cDNA were prepared from 100 ng of total RNA using the WT Plus amplification kit (Affymetrix). Following fragmentation, 5.5 µg of cDNA were hybridized to the GeneChip Human Gene 2.0 ST Array (Affymetrix). GeneChips were washed and stained in the Affymetrix Fluidics Station 450 and scanned using the Affymetrix GeneChip Scanner 3000 7G. Raw data were normalized using RMA in the Affymetrix Expression Console and presented as log transformed signal intensity.

Pathway Enrichment Analysis

A one-way ANOVA test was used on a gene-by-gene basis to test for differential expression between si-GLS1-treated and vehicle-treated PAECs on both soft and stiff matrix backgrounds. Differentially expressed genes were selected based on a p-value cutoff of 0.05 and a fold-change cutoff of 1.5. Pathway enrichment of differentially expressed genes was performed using the Reactome FI analysis tool in the Cytoscape 2.8.1 environment (4). Pathway-by-pathway heat maps were generated using the TM4 MultiExperiment Viewer (5).

Immunoblotting and Antibodies

Cells were lysed in Laemmeli buffer (Boston BioProducts). Protein lysate were resolved by SDS-PAGE and transferred onto a PVDF membrane (Biorad). Membranes were blocked in 5% non-fat milk in TN buffer (50 mM Tris-HCl pH 7.4, 150 mM NaCl) or 5% BSA in TN buffer and incubated in the presence of the primary and then secondary antibodies. After washing in TN buffer containing 0.1% Tween, immunoreactive bands were visualized with the ECL system (Amersham Biosciences). Primary antibodies for YAP1 (#4912; 1/1000) and YAP/TAZ (#8418; 1/1000) were obtained from Cell Signaling. Primary antibodies for GLS1 (ab156876; 1/1000), PC (ab115579; 1/1000), LDHA (ab47010; 1/1000) were obtained from Abcam. A primary antibody for tubulin (T4026; 1/5000) was obtained from Sigma Aldrich. A primary antibody for TAZ (sc-48805) was obtained from Santa Cruz Biotechnology. Appropriate secondary antibodies (anti-rabbit, anti-mouse and anti-goat) coupled to HRP were used (Dako).

Immunofluorescence

After various indicated treatments, cultured cells were fixed with PBS/PFA 4% for 10 min and permeabilized with PBS/Triton 100X 0.1% for 10 min. The cells were then incubated with anti-PCNA (#4912; 1/100; Invitrogen), anti-Ki67 (ab15580; 1/200; Abcam), and/or anti-cleaved caspase-3 (1/200; Cell Signaling) at room temperature for 2 hours. Secondary antibodies coupled with Alexa-594 and/or Alexa-488 (Thermo Scientific) were used at 1/500. Nuclei were counterstained with DAPI (Sigma).

Cell Counting Assays

After specified pre-treatment or transfection protocols as indicated, PAECs or PASMCs were plated in triplicate in 6 well plates at 30 000 cells per well. After overnight incubation for cells to adhere, 6 wells were counted to determine initial count at time of treatments (glutamate, aspartate, BPTES, DON or C968). After 2 days, 4 days or 6 days, the contents of the wells were trypsinized and counted, and proliferation rate was calculated.

BrdU Proliferation Assay

Exponentially growing cells were plated in the indicated matrix for 48 hours. For proliferation assays, 5-bromo-2- uridine (BrdU) was added to the cell culture medium for 1 hour, and BrdU incorporated into the DNA was revealed using a detection kit (BrdU Cell Proliferation Assay Kit #6813, Cell Signaling).

Scratch Assay

Confluent PAECs were wounded using pipet tips and wound bed closures were followed serially over 10 hours. Brightfied images were taken each hour through a 106 phase contrast objective with a CoolSNAPHQ CCD Camera managed by Metamorph Software (Roper Scientific). Wound bed areas were quantified using the NIH ImageJ software (http://rsb.info.nih.gov/ij/).

Mitochondrial Potential Measurements

As described previously (6), cells were stained with 2 nM TMRM (tetramethylrhodamine methyl ester, Life Technologies) and Hoechst (0.1 µg/ml) for 30 min at 37° C. 5 to 8 random images per well were recorded using a Nikon TE2000 epifluorescent microscope. Mean cell fluorescence intensity for each image was determined using the NIH ImageJ software.

Caspase 3/7 Assay

Caspase 3/7 activity was quantified using the Caspase-Glo 3/7 Assay (Promega), according to manufacturer's instructions. Briefly, cells were plated on hydrogel of different stiffness and treated as described. Twenty four hours after plating, cells were cultured in the presence or absence of serum for twenty-four hours. Cells were then lysed and 10 µg of total protein were incubated for 1 h with the caspase substrates, and luminescence was quantified by plate reader (SynergyHTX multi-mode reader, Biotek).

Animals

Monocrotaline-treated rats: As we previously described (7, 8), male Sprague-Dawley rats (10-14 week old) were injected with 60 mg/kg monocrotaline at time 0; at 0-4 weeks post-exposure, right heart catheterization was performed followed by harvest of lung tissue for RNA extraction or paraffin embedding, as described below (section: Tissue harvest).

Simian immunodeficiency virus-infected rhesus macaques: As previously described (9), rhesus (RM) macaques, aged 6 to 10 years, were obtained from national primate centers or vendors approved by the Division of Laboratory Animal Research at the University of Pittsburgh. Macaques were intravenously inoculated with SIV AB670 (gift of M. Murphey-Corb, University of Pittsburgh). Plasma viral loads and peripheral blood $CD4^+$ T cells were determined by quantitative RT-PCR and flow cytometry. Pulmonary artery catheterization was performed before infection and repeated at 6 months and 10-12 months after infection. Furthermore, lung tissue was obtained during necropsy, and pulmonary arteries were examined by a veterinary pathologist blinded to the identity of the monkeys.

Metabolite Extraction from Plasma

Accordingly to a previously published protocol (10), metabolites were extracted from 20 µL of plasma by adding 80 µL cold methanol 100% in which an internal standard (ISTD) was added.

Isolation of Rat Pulmonary Vascular Endothelial Cells

As previously reported (8, 11), lobes of lung tissue from a rat were diced with scissors, to which 200 µL of collagenase D solution (Sigma) was added for a final concentration of 2 mg/ml collagenase D in 4.8 mL HEPES buffer (pH=7.4). After incubation for 30 min at 37° C. with automated rotation, 20 µL of DNase I (Sigma, final concentration of 80 U/mL DNase I) was added and incubated on ice for 30 min. The solution was filtered twice by a 70 µm cell strainer (BD Biosciences) to yield a single cell suspension.

After two rounds of PBS wash, cell pelleting, and resuspension, the ACK lysing buffer (Gibco) was used to remove erythrocytes. Remained cells were incubated 30 min at 4° C. with a mouse anti-rat-CD31 antibody (BD Pharmigen 555025). Cells were PBS washed twice and incubated 15 min with anti-mouse IgG1 MicroBeads (Miltenyi Biotec) according to the manufacturer protocol. Single CD31-positive cells were then collected using an autoMACS Pro Separator, per the manufacturer's instructions (Miltenyi Biotec). The purity (>95%) of CD31 positive cells was confirmed by flow cytometric analysis by a FACScan flow cytometer (BD Biosciences) after cells labeling with the FITC-conjugated anti-CD31 (ab33858, Abcam).

Tissue Harvest of Rat Lungs

After physiological measurements by direct right ventricular puncture, the pulmonary vessels were gently flushed with 1 cc of saline to remove the majority of blood cells, prior to harvesting cardiopulmonary tissue. The heart was removed, followed by dissection and weighing of the right ventricle (RV) and of the left ventricle+septum (LV+S). Organs were then harvested for histological preparation or flash frozen in liquid N2 for subsequent homogenization and extraction of RNA and/or protein. To further process lung tissue specifically, prior to excision, lungs were flushed with PBS at constant low pressure (approximately 10 mmHg) via right ventricular cannulation, followed by tracheal inflation of the left lung with 10% neutral-buffered formalin (Sigma-Aldrich) at a pressure of approximately 20 cm H2O. After excision and 16 hours of fixation in 10% neutral-buffered formalin at 25° C., lung tissues were paraffin embedded via an ethanol-xylene dehydration series, before being sliced into 5 µm sections (Hypercenter XP System and Embedding Center, Shandon).

GLS1 Activity Assay

According to the manufacturer instructions (Glutaminase Microplate Assay Kit, Cohesion Biosciences), flash frozen rat lung tissue (0.1 g/sample) was homogenized in 1 mL of assay buffer on ice and centrifuged at 8000 g 4° C. for 10 min. Protein concentration was determined by Bradford assay. Samples, normalized to total protein (100 µg), were incubated with kit reagents for 1 hr at 37° C., and absorbances were measured at 420 nm.

Immunohistochemistry and Immunofluorescence of Lung Sections

Lung sections (5 µm) were deparaffinized and high temperature antigen retrieval was performed, followed by blocking in TBS/BSA 5%, 10% donkey serum and exposure to primary antibody and biotinylated secondary antibody (Vectastain ABC kit, Vector Labs) for immunohistochemistry or Alexa 488, 568 and 647-conjugated secondary antibodies (Thermo Fisher Scientific) for immunofluorescence. A primary antibody against YAP1 (#4912; 1/200 or sc101199; 1/50) were obtained from Cell Signaling and Santa Cruz Biotechnology respectively. Primary antibodies against, GLS1 (ab156876; 1/100), PC (ab115579; 1/100), LDHA (ab47010; 1/200) and α-SMA (ab32575; 1/1000) were purchased from Abcam. A primary antibody against CD31 (sc-1506; 1/100), was purchased from Santa Cruz Biotechnology. A primary antibody against PCNA (13-3900, 1/100) was purchased from Thermo Fisher Scientific. In most cases, color development was achieved by adding streptavidin-biotinylated alkaline phosphatase complex (Vector Labs) followed by Vector Red alkaline phosphatase substrate solution (Vector Labs). Levamisole was added to block endogenous alkaline phosphatase activity (Vector Labs). Pictures were obtained using an Olympus Bx51 microscope or ZEISS LSM Exciter confocal microscope. Small pulmonary vessels (<100 μm diameter) present in a given tissue section (>10 vessels/section) that were not associated with bronchial airways were selected for analysis (N>5 animals/group). Intensity of staining was quantified using ImageJ software (NIH). Degree of pulmonary arteriolar muscularization was assessed in paraffin-embedded lung sections stained for α-SMA by calculation of the proportion of fully and partially muscularized peripheral (<100 μm diameter) pulmonary arterioles to total peripheral pulmonary arterioles, as previously described (12). All measurements were performed blinded to condition.

Atomic Force Microscopy

Rat lungs were inflated with 0.025 g of OCT by g of body weight, frozen on liquid nitrogen vapor and store at −80° C. Rat lung slices (10 μm thickness) were cut out from their glass slide and the fragment of glass containing the sample was glued on the bottom of a 50 mm dish (Willco Glass Bottom Dish). Before measurements the sample was first rinsed and after covered with 4 ml of PBS 1×. The mechanical properties of the samples were studied using a BioScope Catalyst atomic force microscope (Bruker) coupled with and optical microscope (Leica DMI6000B) that enables, by phase contrast, to pinpoint the areas of interest. For each sample, from five to a maximum of 9 vessels (<100 μm diameter) were analyzed using the "Point and Shoot" method, collecting from 35 to 80 force-distance curves at just as many discrete points. The experiments of microindentation were performed in PBS using a probe with a Borosilicate Glass spherical tip (5 μm of diameter) and a cantilever with a nominal spring constant of 0.06 N/m (Novascan). Indentations were carried out using a velocity of 2 μm/s, in relative trigger mode and by setting the trigger threshold to 2 nN. The apparent Young's modulus was calculated using the NanoScope Analysis 1.50 software (Bruker), fitting the force curves to the Hertz spherical indentation model and using a Poisson's ratio of 0.4. To avoid large indentation, a minimum and a maximum Force Fit Boundary of 5% and 25% respectively of the whole force curve was taken into account for the fit.

Picrosirius Red Stain and Quantification

Picrosirius Red stain was achieved through the use of 5 μm paraffin sections stained with 0.1% Picrosirius Red (Direct Red80, Sigma-Aldrich) and counterstained with Weigert's hematoxylin to reveal fibrillar collagen. The sections were then serially imaged using with an analyzer and polarizer oriented parallel and orthogonal to each other. Microscope conditions (lamp brightness, condenser opening, objective, zoom, exposure time, and gain parameters) were maintained throughout the imaging of all samples. A minimal threshold was set on appropriate control sections for each experiment in which only the light passing through the orthogonally-oriented polarizers representing fibrous structures (i.e., excluding residual light from the black background) was included. The threshold was maintained for all images across all conditions within each experiment. The area of the transferred regions that was covered by the thresholded light was calculated and at least 10 sections/vessel per condition were averaged together (NIH ImageJ software). Targeted LC-MS/MS Metabolite extraction was performed essentially as described with minor modifications (35). Briefly, metabolites were extracted from cultured cells and CD31+ cells on dry ice using 80% aqueous methanol pre-cooled at −80° C. Metabolites were extracted from plasma pre-cleared by centrifugation at 20,000×g for 10 min at 4° C. Supernatants were extracted with four volumes of 100% methanol pre-cooled at −80° C. for four hours at −80° C. An internal standard, [$^{13}C_4$]-2-oxoglutarate (Cambridge Isotope Laboratories) was added during metabolite extraction. Insoluble material from both cell and plasma extractions was removed by centrifugation at 20,000×g for 15 min at 4° C. The supernatant was analysed by targeted LC-MS/MS as previously described (36). Metabolites were separated using a ZIC-HILIC stationary phase (150 mm×2.1 mm×3.5 mm; Merck). The MS parameters were optimized using a glutamine standard solution. Monitored mass transitions were 87>87 (pyruvate), 115>73+99 (succinate), 132>88 (aspartate), 145>101 (2OG), 145>127 (glutamine), 146>128 (glutamate), and 149>105([$^{13}C_4$]-2OG). Mass transitions and retention time windows were confirmed by the analysis of neat and matrix-spiked standards. Peak areas were quantified by Xcalibur Software (Thermo) and manually reviewed.

Extracellular Flux Analyses

PAECs (30,000 cells/well) or PASMCs (50,000 cells/well) were plated in Seahorse Bioscience 24 well plates pre-coated with 20 μL of soft or stiff gel (as described in Supplemental). After overnight incubation to allow attachment, cells were washed 2 times in assay media (DMEM without phenol red or pyruvate containing 0.5% dialyzed FBS and 0.1 mg/mL uridine at pH 7.4; manufactured by Seahorse Biosciences) and incubated in 500 μL of fresh assay media. Oxygen consumption rate (OCR) and extracellular acidification rate (ECAR, a surrogate marker of glycolysis) were measured on an XF24 or XFe24 Analyzer (Seahorse Biosciences). Mitochondrial and glycolytic stress assays were performed according to the manufacturer's protocols. OCR and ECAR were normalized to cell count measured after assay completion.

Inhibition of YAP1 in PH Rats

To induce PH, male Sprague-Dawley rats (10-14 week old) were injected intraperitoneally with 60 mg/kg monocrotaline (Sigma-Aldrich). After two days, rats underwent intraperitoneal injection daily with 25 mg/kg of verteporfin (Active Biochemicals Company, Ltd) solubilized in 5% dimethyl sulfoxide (DMSO, Sigma-Aldrich). Two days after the last injection on day 21 post-monocrotaline injection, right heart catheterization was performed followed by harvest of lung tissue and CD31+ cells for RNA or protein extraction, paraffin embedding, or cryopreservation with OCT (Sigma-Aldrich), as we described (2).

Inhibition of GLS1 in PH Rats

To induce PH, male Sprague-Dawley rats (10-14 week old) were injected intraperitoneally with 60 mg/kg monocrotaline (Sigma-Aldrich). After two days, serial intraperitoneal injections were given daily of C968 (10 mg/kg, Sigma-Aldrich), and after seven days post-monocrotaline injection, serial intraperitoneal injections were given daily of CB839 (10 mg/kg, Selleck Chemicals). Two days after the last injection on day 21 post-monocrotaline injection, right heart catheterization was performed followed by harvest of lung tissue and CD31+ cells for RNA or protein extraction, paraffin embedding, or cryopreservation with OCT (Sigma-Aldrich), as we described (2).

Human Subjects

Figure 8:
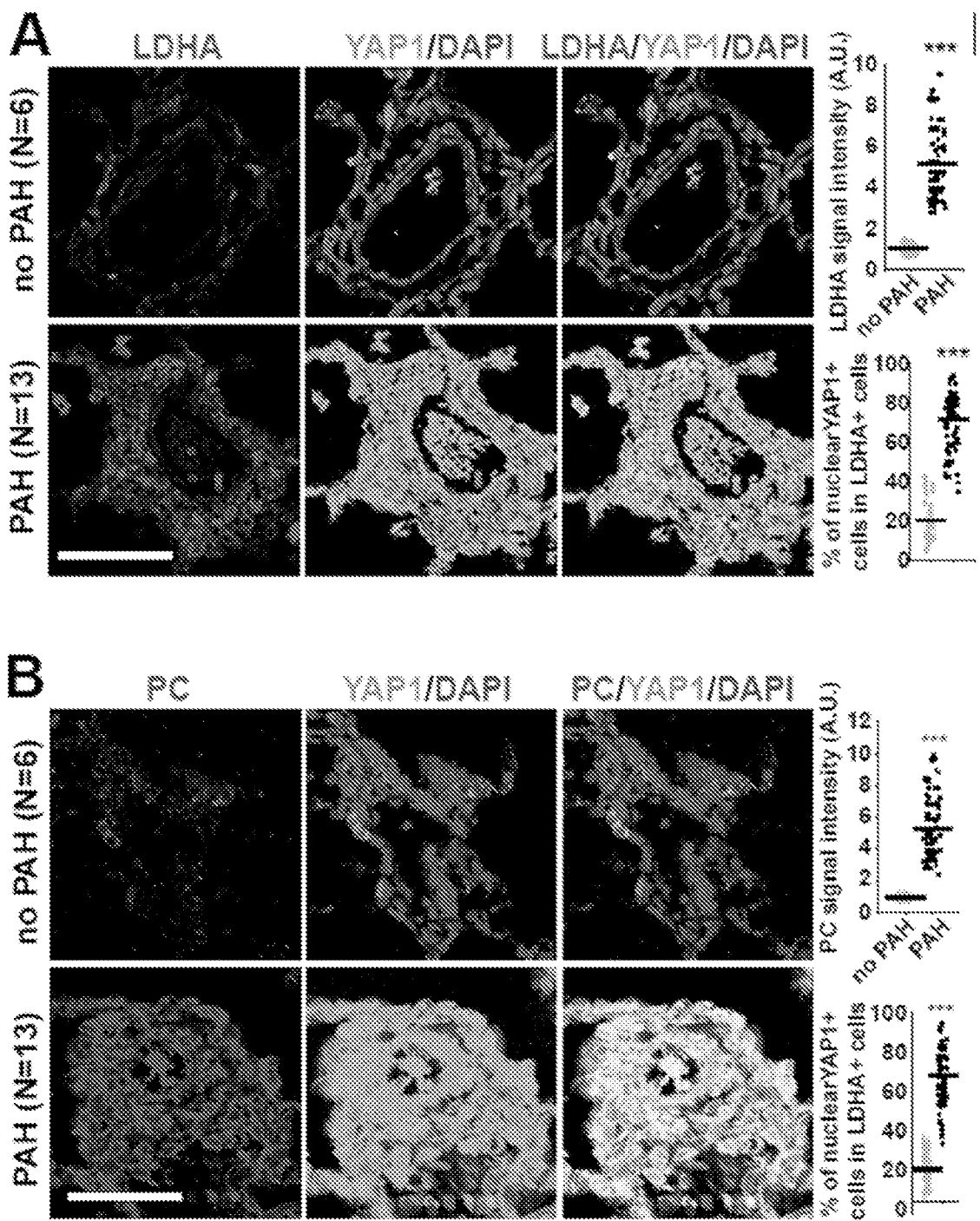
FIG. 8 (A-E) shows that an increase of periarteriolar fibrillar collagen correlates with increases of GLS, glutaminolysis, and aspartate production in human patients suffering from multiple forms of PAH. A-B) Co-immunofluorescence microscopy and quantification revealed that the increase of periarteriolar fibrillar collagen deposition is accompanied by increased LDHA (A) and PC (B) expression in human PAH (n=6). Such staining further demonstrated an increase in YAP1/LDHA (A) and YAP1/PC (B) double-positive cells in diseased pulmonary arterioles. C) These changes were accompanied by an increase of proliferating pulmonary vascular cells (Ki67+) in both medial (α-SMA+) and endothelial (vWF+) compartments and a significant reduction of vascular apoptotic cells (CC-3+). D-E) Similar changes were observed in plexiform lesions.
Figure 8:
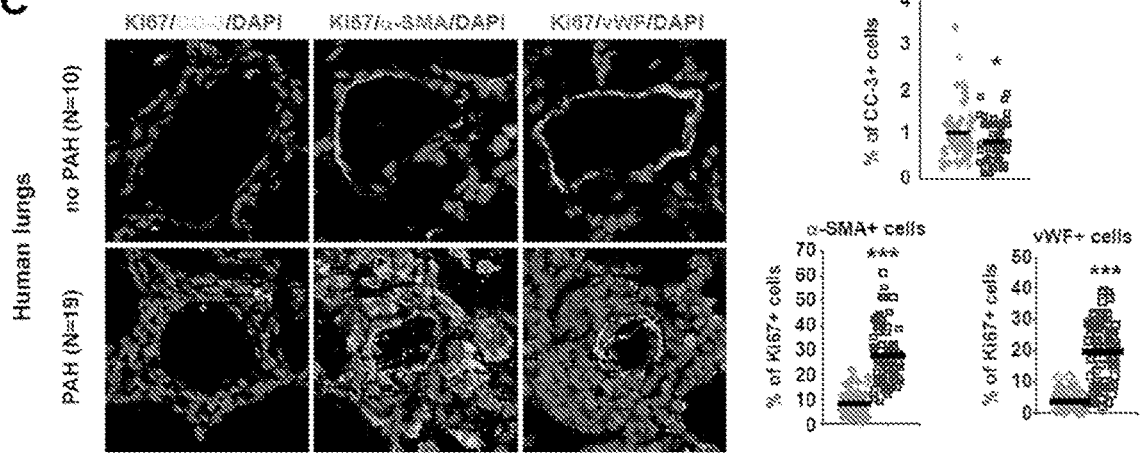
Figure 8:
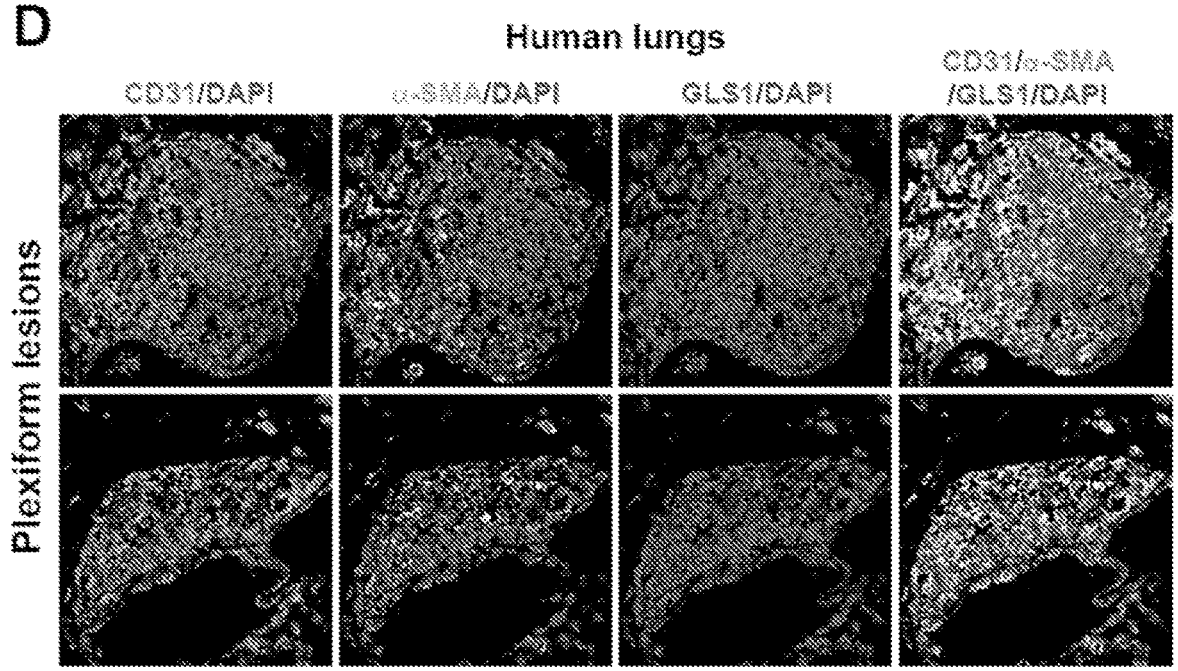
Figure 8:
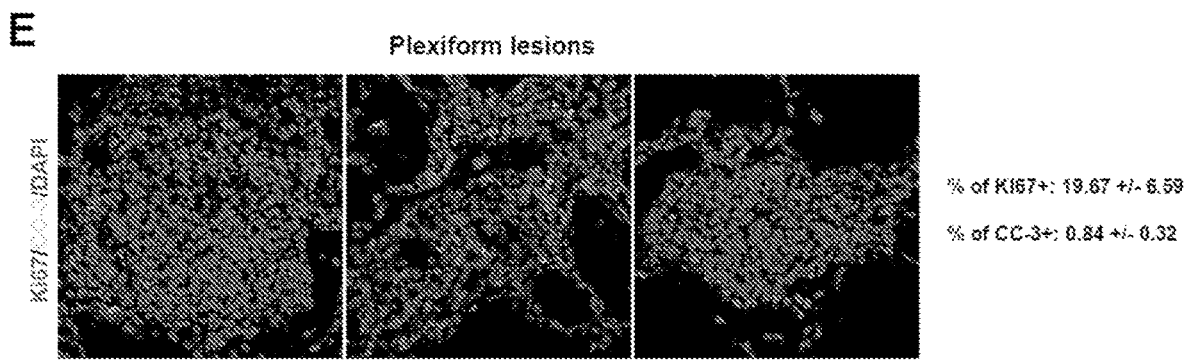
Figure 9:
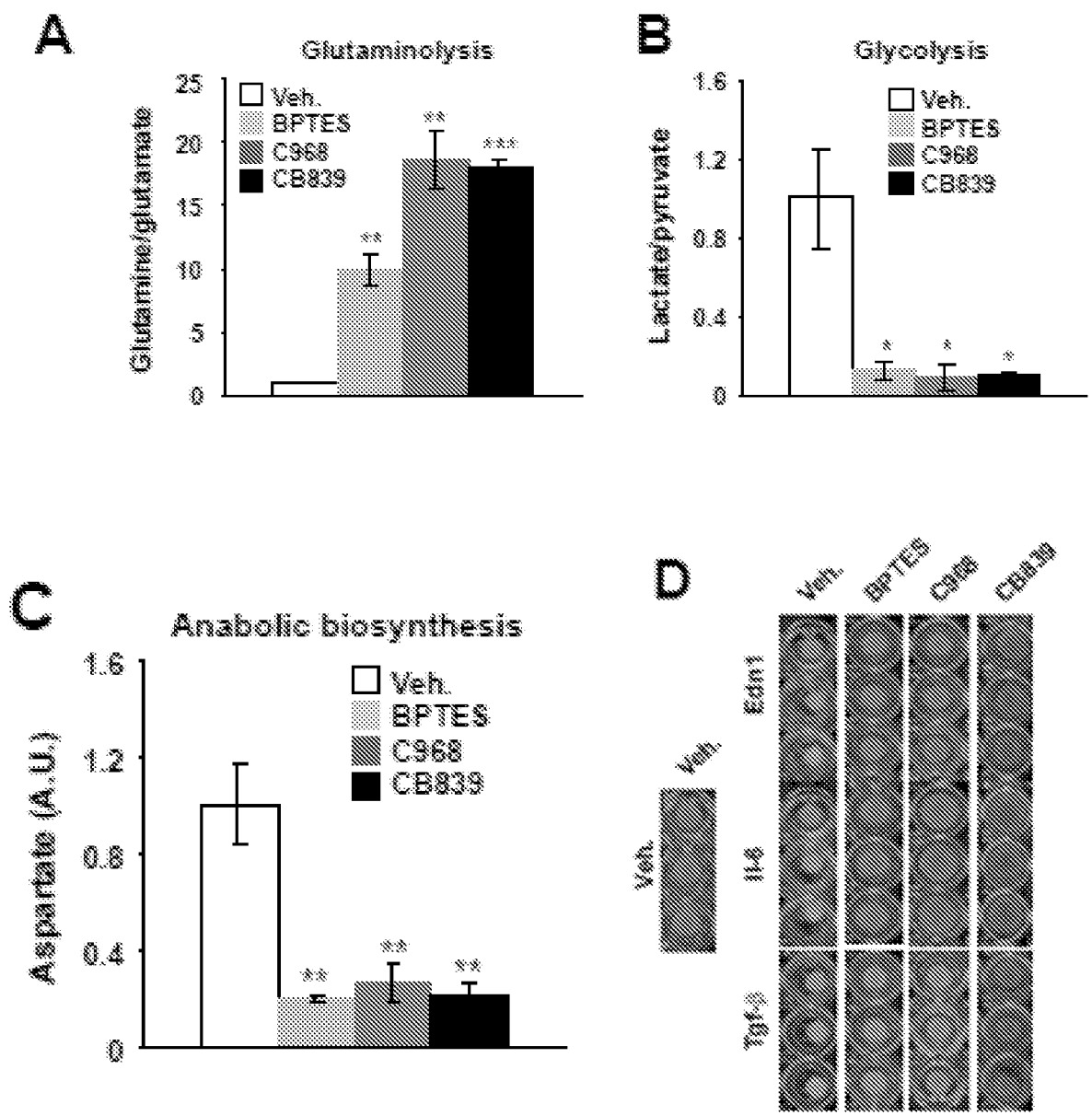
FIG. 9 (A-L) demonstrates that glutaminolysis sustains the metabolic demands of activated PAAFs in order to build a pro-diseased extracellular matrix. A-C) Pharmacological inhibition of GLS1 by either BPTES, C968 or CB839 blunted metabolic activation of PAAFs cultivated on stiff matrix as reflected by decreased glutaminolysis (A), glycolysis (B) and aspartate production (C). D-E) Pharmacological inhibition of GLS1 by either BPTES, C968 or CB839 decreased PAAFs dependent ECM remodelling upon stimulation by pro-inflammatory cytokines (EDN1, IL6 or TGF-b). F) RT-qPCR revealed that inhibition of GLS1 by either C968 or CB839 decreased TGF-b-induced ECM related genes expression as well as fibroblast activation marker (a-SMA). G-H) Fibrilar collagen visualization (G) and quantification (H) by picrosirius red staining confirmed a decreased of ECM remodelling by activated PAAF (TGF-b) in presence of GLS1 inhibitors. I-M) PAAFs were cultivated upon indicated treatments. Cells were removed and pulmonary arterial endothelial cells (PAECs) were cultivated on the matrix synthesized by the PAAF. PCNA staining (I) and quantification revealed a decreased of proliferative cells (PCNA+) on matrix remodelled by PAAFs treated with TGF-b+GLS1 inhibitor compared to controls (TGF-b). In the same conditions, RT-qPCR revealed a decreased of pro-inflammatory cytokines genes expression (J-L) by PAECs cultivated on matrix synthesized by PAAF treated with TGF-b+GLS1 inhibitor compared to controls (TGF-b). Data are expressed as mean±SEM (*P<0.05, § P<0.01, # P<0.001) of at least 3 independent experiments performed in triplicate. Paired samples were compared by 2-tailed Student's t test, while 1-way ANOVA and post-hoc Tukey's tests were used for group comparisons.
Figure 9:
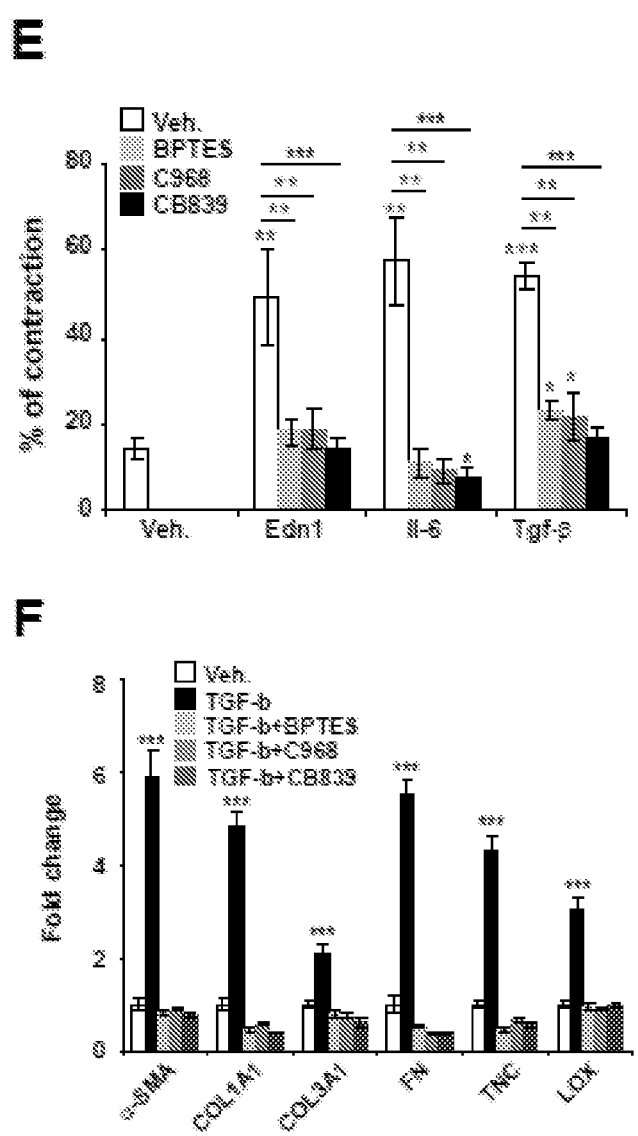
Figure 9:
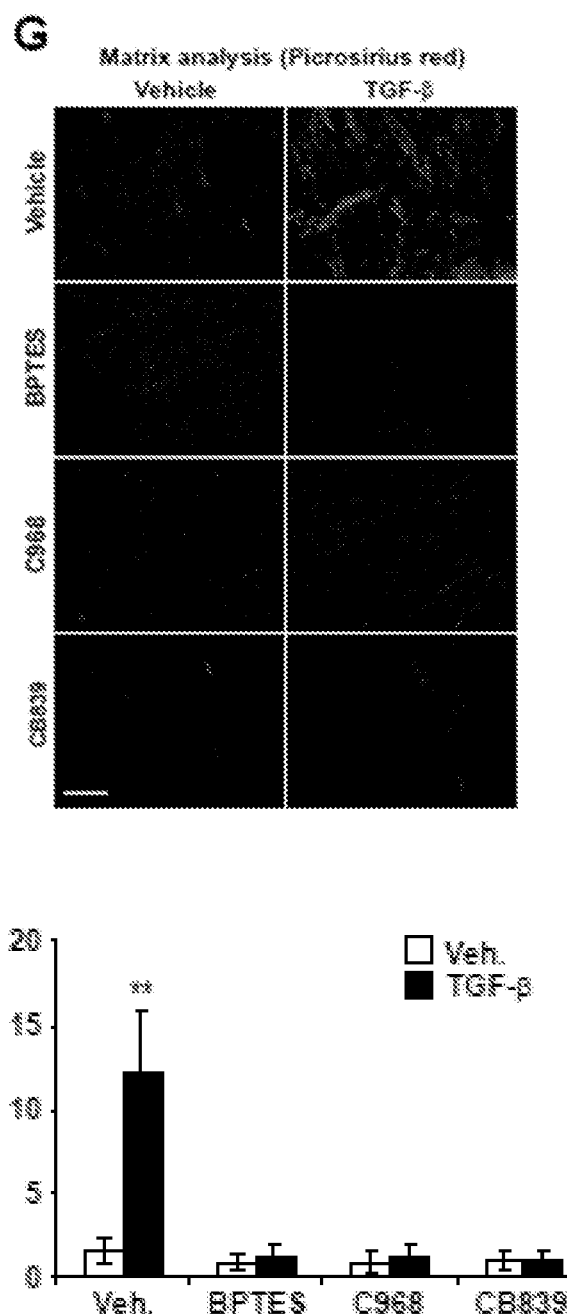
Figure 9:
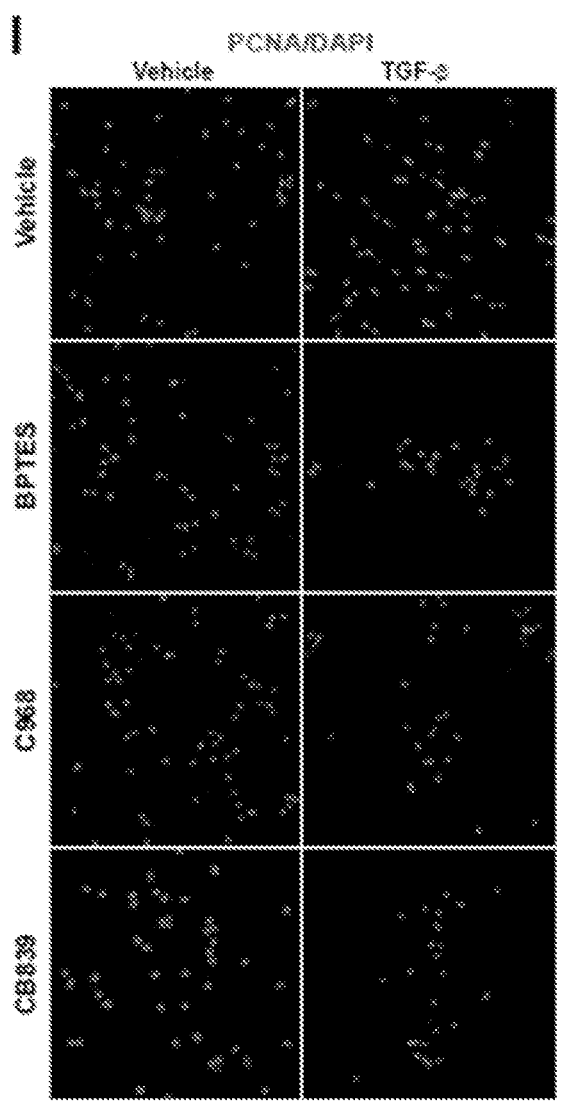
Figure 9:
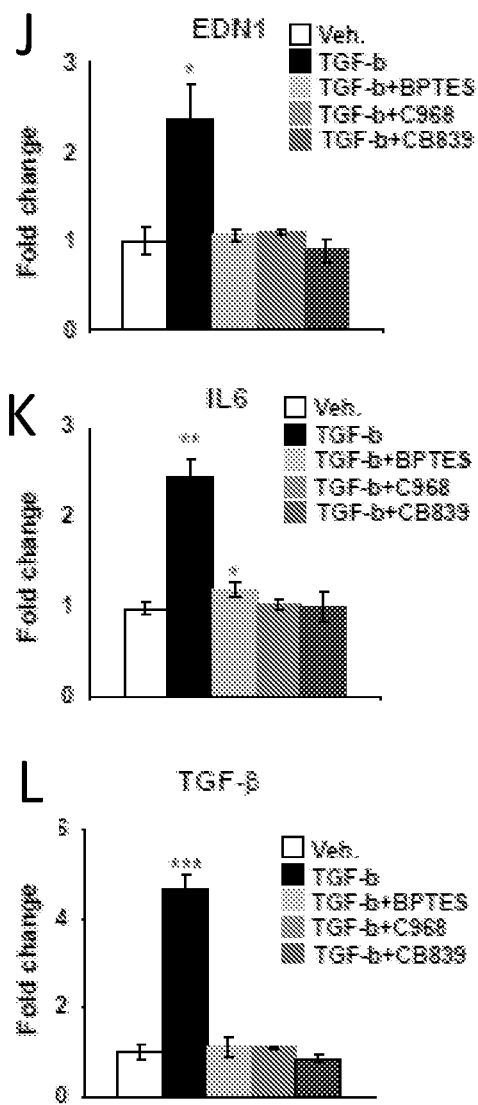
Figure 10:
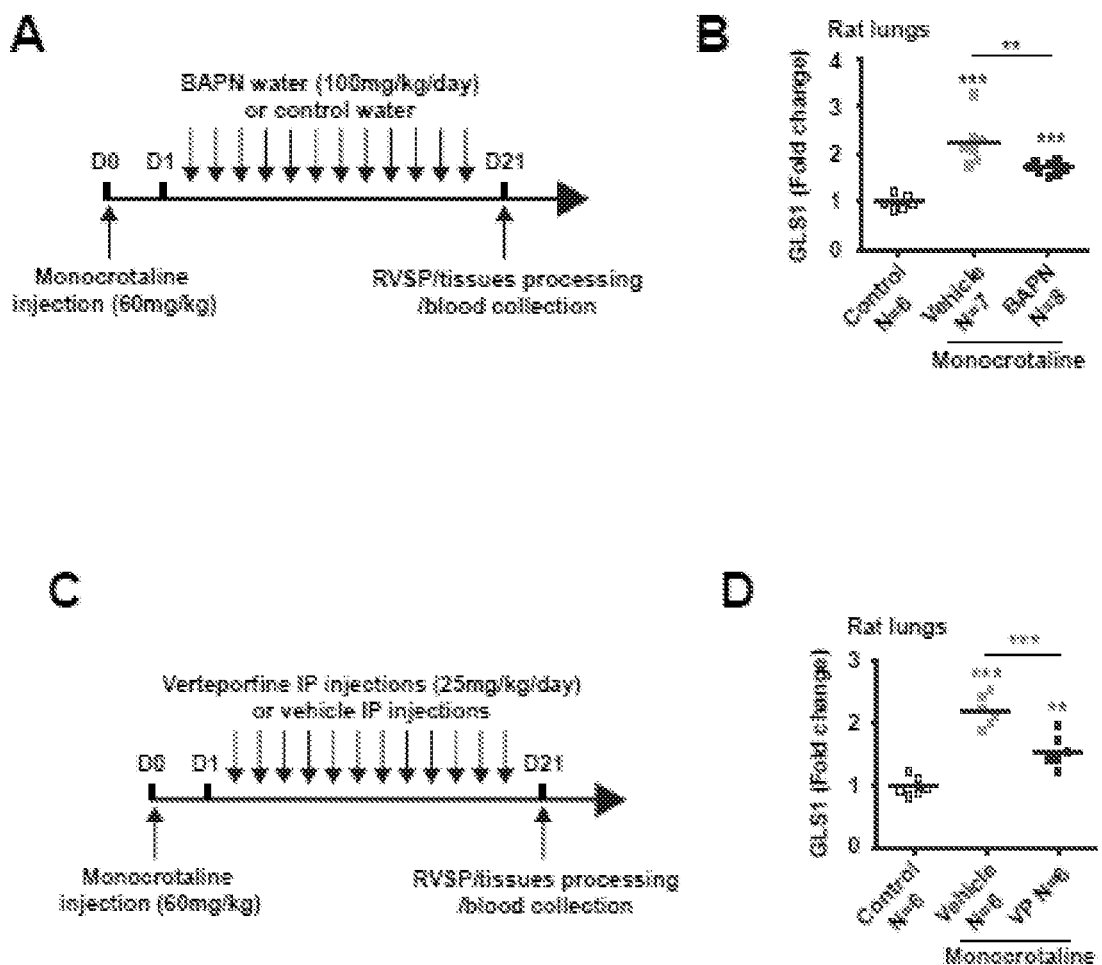
FIG. 10 (A-F) shows pharmacological inhibition of ECM remodelling or GLS1 reveal a feedback loop between ECM stiffness and glutaminolysis. A-D) Following monocrotaline exposure, rats were treated with daily BAPN (n=8) versus vehicle (A-B; n=7) or with daily i.p. injections of separate verteporfin (n=6) versus separate vehicle (C-D; n=6). As assessed by RT-qPCR, both BAPN and verteporfin decreased GLS1 expression in lungs of monocrotaline-exposed rats. E-F) Following monocrotaline exposure, rats were treated with daily CB839 (n=8) versus vehicle (E-F; n=7). Atomic force microscopy (F) revealed decreased pulmonary arteriolar (<100 μm diameter) stiffness in CB839-treated rats. Horizontal lines denote median; symbols denote individual pulmonary arterial measurements. In all panels, mean expression in control groups was assigned a fold change of 1, to which relevant samples were compared. Paired samples were compared by 2-tailed Student's t test, while 1-way ANOVA and post-hoc Tukey's tests were used for group comparisons (*P<0.05, # P<0.001).
Figure 10:
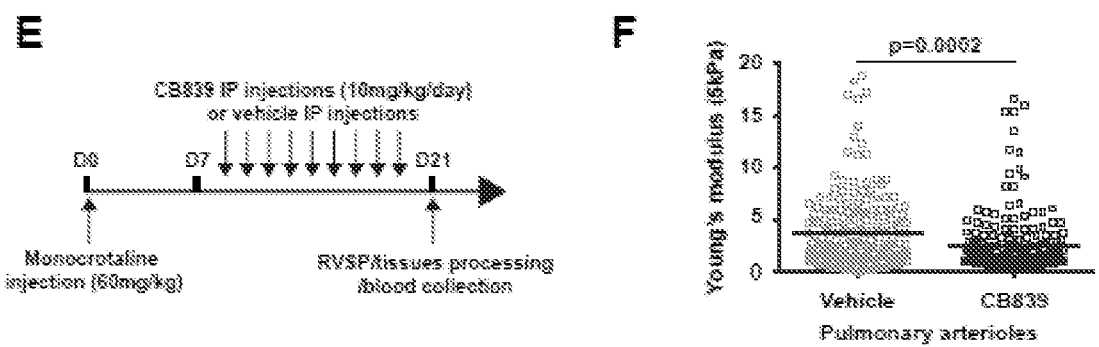

Informed consent was obtained for all study procedures. For formalin-fixed paraffin-embedded lung samples, human PH specimens were collected from unused or discarded surgical samples (Table 2), some of which we have described previously (37); non-diseased human lung specimens from the New England Organ Bank have been described (38). For plasma harvest and analysis described in FIG. 8E-G, individuals were chosen with clinically significant dyspnea and undergoing right heart catheterization at the Brigham and Women's Hospital, Boston, Mass., USA (Table 3, some of whom were described in (26)). Subjects were stratified by the presence or absence of clinical PH, as defined by elevated mean pulmonary arterial pressure >25 mmHg (mPAP). For measurements of pulmonary artery compliance, a cohort of 42 HIV-infected individuals underwent pulmonary arterial catheterization at the University of Pittsburgh, Pittsburgh, Pa., USA, as part of ongoing studies of lung disease in HIV-infected persons. A diagnosis of PAH (mPAP>25 mmHg) was made in 11 individuals (Table 4). Based on these invasive hemodynamic measurements, pulmonary arterial compliance was calculated by stroke volume/pulse pressure. Finally, in human subjects where peripheral plasma was analyzed for circulating metabolites (Table 5), a separate cohort of HIV-infected individuals were recruited at the University of California, San Francisco, San Francisco, Calif., USA either with documented PAH (assessed by invasive pulmonary arterial catheterization (mPAP>25 mmHg) or without PAH (assessed either with invasive pulmonary arterial catheterization (mPAP<25 mmHg or by non-invasive echocardiographic estimation of pulmonary arterial systolic pressure <40 mm Hg).

Human Plasma Sampling

To collect blood from subjects from the main pulmonary artery, clinically indicated right heart catheterization procedures were performed by standard protocol via a right internal jugular approach under fluoroscopic guidance, as previously described (37). The catheter was positioned into the main pulmonary artery, as confirmed by fluoroscopy and hemodynamic waveforms. Blood was then drawn from the distal catheter port and collected in standard vacutainer tubes with K+-EDTA anticoagulant. Plasma was extracted after standard centrifugation of blood, followed by storage at −80° C. To collect venous peripheral blood from HIV-positive subjects, as we previously described (40), venous blood was collected in standard anticoagulant (EDTA)-treated vacutainer tubes. Cellular elements were pelleted in each blood sample following blood draw via centrifugation at 2000×g for 10 min. The supernatant plasma was then aliquoted and immediately frozen at −80° C.

Statistics

Cell culture experiments were performed at least three times and at least in triplicate for each replicate. The number of animals in each group was calculated to measure at least a 20% difference between the means of experimental and control groups with a power of 80% and standard deviation of 10%. The number of unique patient samples for this study was determined primarily by clinical availability. In situ expression/histologic analyses of both rodent and human tissue, and pulmonary vascular hemodynamics in mice and rats were performed in a blinded fashion. Numerical quantifications for in vitro experiments using cultured cells or in situ quantifications of transcript/miRNA expression represent mean±standard deviation (SD). Numerical quantifications for physiologic experiments using rodents or human reagents represent mean±standard error of the mean (SEM). Immunoblot images are representative of experiments that have been repeated at least three times. Micrographs are representative of experiments in each relevant cohort. Normality of data distribution was determined by Shapiro Wilk testing. Paired samples were compared by a 2-tailed Student's t test for normally distributed data, while Mann-Whitney U non-parametric testing was used for non-normally distributed data. For comparisons among groups, one-way ANOVA and post-hoc Tukey testing was performed. A P-value less than 0.05 was considered significant.

Example 2

Mechanical Stimuli Regulate Metabolic Reprogramming in Pulmonary Vascular Endothelial and Smooth Muscle Cells To determine whether mechanical/physical cues conveyed by ECM stiffness modulate vascular cell metabolism, a metabolic screening of pulmonary vascular cell types was performed by culture on soft or stiff matrix. Via extracellular flux analysis, oxygen consumption rate (OCR) and extracellular acidification rate (a surrogate marker of glycolysis) were assessed in pulmonary arterial endothelial cells (PAECs). As reflected by extracellular acidification rate quantification, ECM stiffness increased basal glycolysis while concomitantly decreasing glycolytic reserve capacity, calculated as the difference between oligomycin A-induced extracellular acidification rate and basal extracellular acidification rate (data not shown). Thus, cells on stiff matrix displayed a glycolytic flux closer to their maximal rate compared with cells on soft matrix. Alternatively, increased ECM stiffness significantly decreased basal OCR, ATP-dependent OCR (difference between basal OCR and oligomycin A-inhibited OCR), and maximal OCR (reflected by induction via carbonyl cyanide-p-trifluoromethoxyphenyl-hydrazone, FCCP), thus reflecting a decrease in mitochondrial oxidative phosphorylation. Corresponding with these metabolic changes, stiff matrix decreased overall mitochondrial potential (data not shown). Similar results were observed for pulmonary arterial smooth muscle cells (PASMCs) (data not shown). Taken together, stiff conditions act as a mechanical stimulus to increase glycolysis and decrease mitochondrial oxidative phosphorylation.

To determine the activity of glycolysis, anaplerosis, and the TCA cycle under these same mechanical conditions, candidate intracellular amino acids and metabolites were measured by liquid chromatography-tandem mass spectrometry (LC-MS/MS) in PAECs. Consistent with increased glycolysis and decreased oxidative phosphorylation in stiff conditions, an increase of lactate/pyruvate ratio was observed. Further consistent with decreased oxidative phosphorylation stiff matrix decreased succinate levels and increased lactate production (data not shown). Importantly, ECM stiffening also decreased intracellular glutamine accompanied by a robust increase of glutamate and aspartate consistent with a putative anaplerotic process accompanying accelerated glycolysis. Levels of three key enzymes in PAECs—lactate dehydrogenase A (LDHA), both GLS1 isoforms (KGA and GAC), and PC—implicated in both glycolysis (LDHA) and anaplerosis (GLS1 and PC) were elevated in stiff matrix (data not shown). As above, similar results were obtained for PASMCs (data not shown). Thus, exposure to stiff matrix not only alters glycolysis and oxidative phosphorylation but also controls anaplerotic replenishment of amino acids.

Example 3

ECM Stiffness Depends on YAP/TAZ to Control Metabolism

Figure 2:
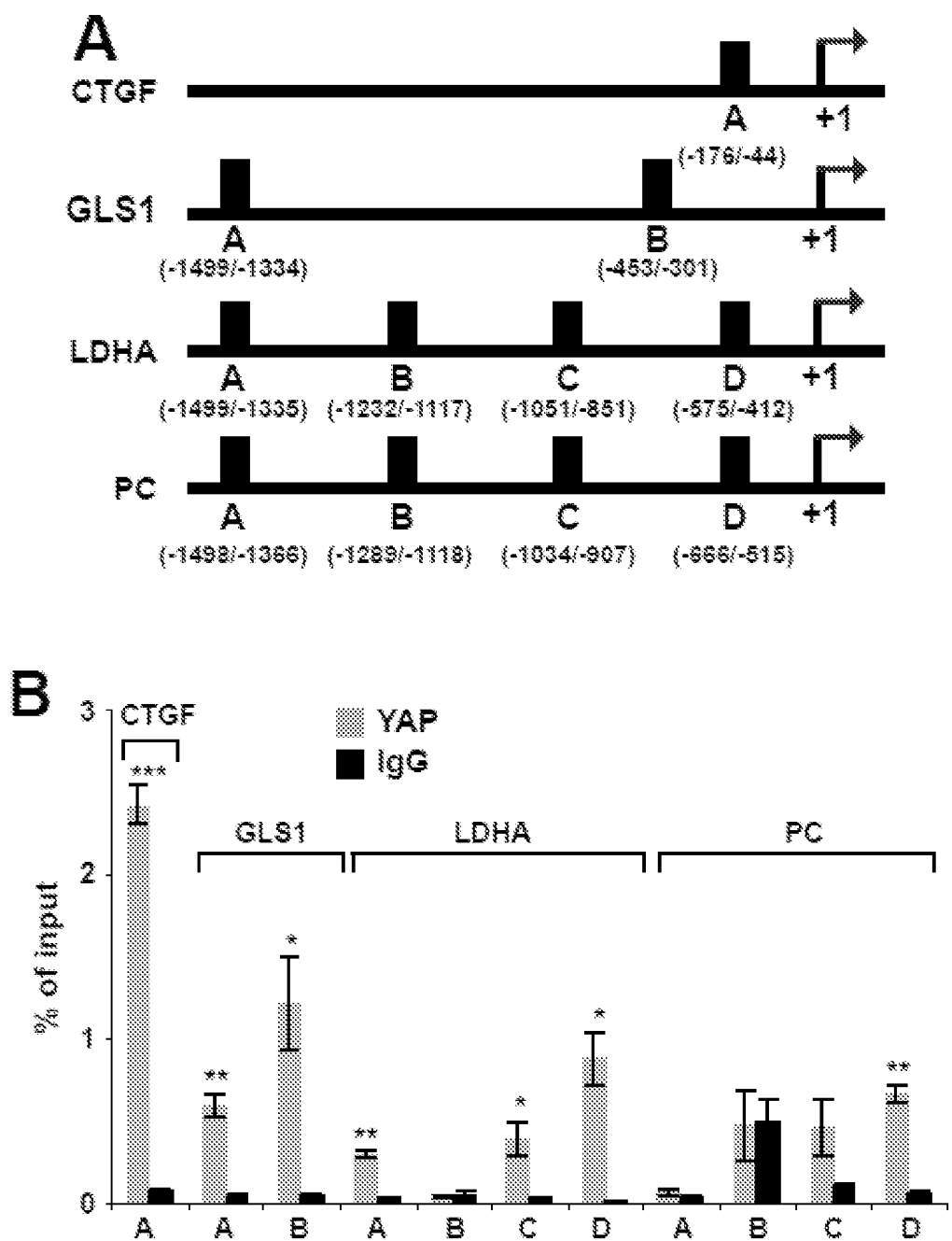
FIG. 2 (A-H) YAP/TAZ control the transcription of key metabolic enzymes. A) Sequence analysis predicted the presence of TEAD binding sites (labeled as A-D) in the promoter regions of GLS1, LDHA, and PC. B) ChIP-qPCR confirmed the presence of TEAD/YAP binding sites in the GLS1, LDHA, and PC promoter regions. CTGF, a known YAP target, was used as a positive control. Results are expressed as percent of total input DNA prior to immunoprecipitation with anti-YAP or anti-IgG control. C-E) RT-qPCR (C) accompanied by immunoblotting (D) and densitometry (E) revealed that increased GLS1, LDHA, and PC expression in PAECs in stiff matrix was blunted by YAP/TAZ knockdown. F-H) RT-qPCR (F) and immunoblotting/densitometry (G-H) revealed that YAP (pYAP) increased GLS1, LDHA, and PC expression in PAECs in soft matrix. In all panels, mean expression in control groups (siNC, pYAP cultivated on soft matrix) was assigned a fold change of 1, to which relevant samples were compared. Data are expressed as mean±SEM ($*P<0.05$; $P<0.01$, $*P<0.001$). Scale bars, 20 µm. (Similar results were found in PASMCs (peripheral arterial smooth muscle cells), data not shown).
Figure 2:
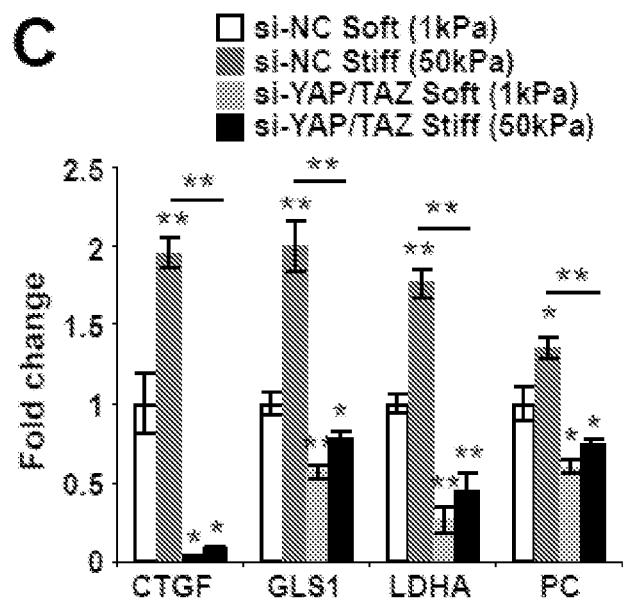
Figure 2:
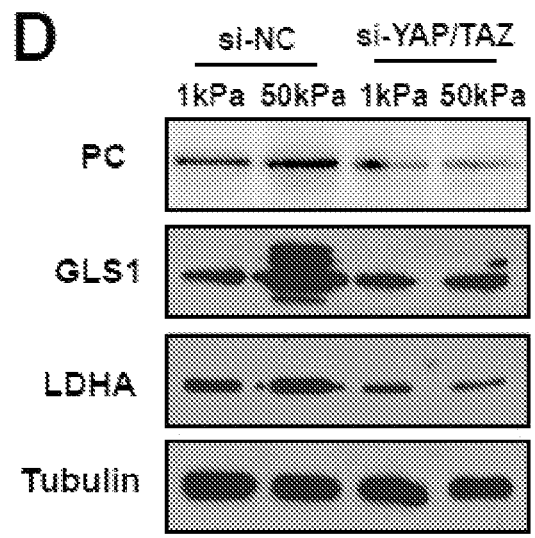
Figure 2:
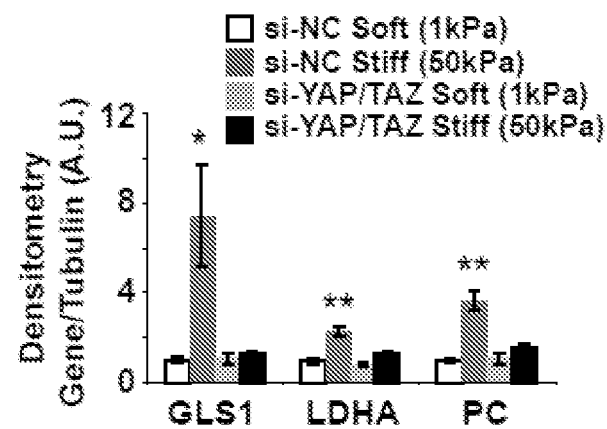
Figure 2:
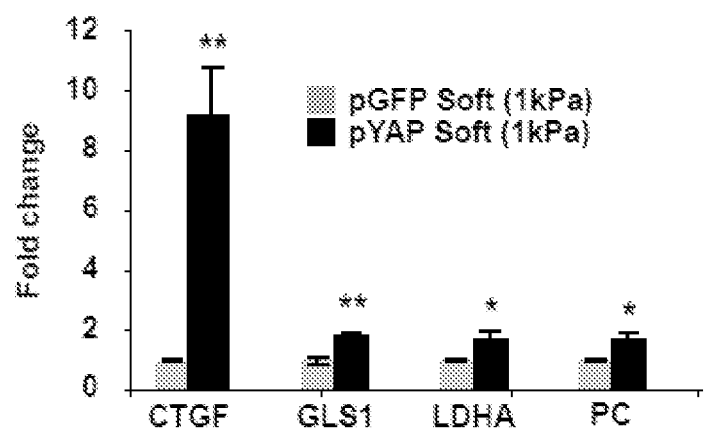
Figure 2:
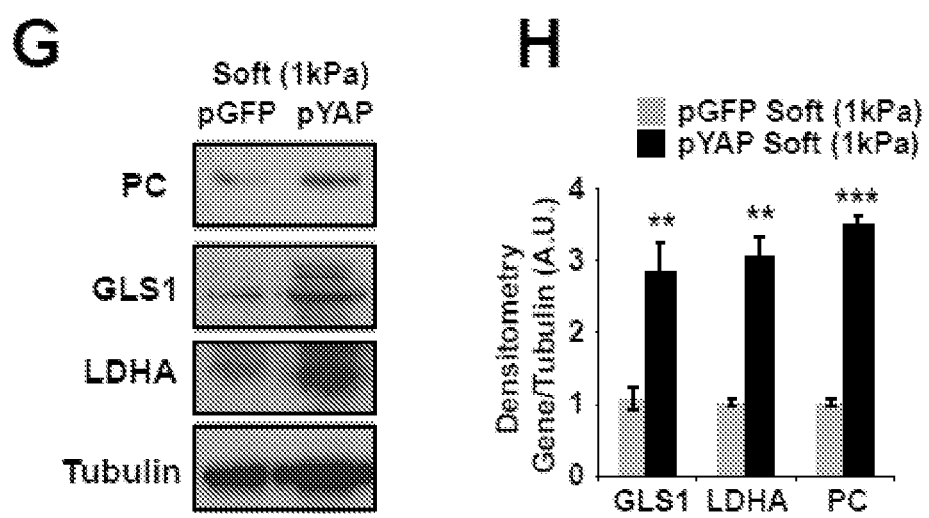

Given prior findings that YAP and TAZ act as mechanosensors in pulmonary vascular cells, it was determined whether YAP/TAZ are important in modulating the consequences of ECM stiffening on metabolic reprogramming. In PAECs in stiff matrix, YAP/TAZ knockdown (FIG. 2A) decreased lactate/pyruvate ratio (FIG. 2B), reflecting its control over glycolysis. YAP/TAZ knockdown also blunted the anaplerotic actions of stiff ECM on glutamine, glutamate, and aspartate production (FIG. 2C). Correspondingly, mitochondrial membrane potential was also sustained during YAP/TAZ knockdown in stiff matrix (data not shown). Conversely, in PAECs grown in soft matrix, stable expression of YAP (pYAP) increased lactate/pyruvate ratio; decreased glutamine and increased glutamate and aspartate; and consequently, decreased mitochondrial membrane potential (data not shown). Notably, the same pathways of glycolysis and glutaminolysis mechanically controlled by stiff ECM in PAECs were activated by YAP/TAZ in PASMCs (data not shown).

Several putative binding sites for YAP/TAZ complexes (TEAD sites) were revealed by sequence analysis of the promoter regions of key metabolic enzymes responsible for glycolysis and glutaminolysis—LDHA, GLS1, and PC (FIG. 2A). ChIP-qPCR demonstrated the direct binding of YAP on at least one site for each gene (FIG. 2B). Correspondingly, siRNA knockdown of YAP/TAZ in PAECs (FIG. 2C-E) and in PASMCs (data not shown) decreased target gene expression, while forced YAP expression in PAECs in soft matrix increased their levels (FIG. 2F-H). Taken together, YAP/TAZ are integral to the mechano-triggered, glycolytic and glutaminolytic metabolic reprogramming events initiated by ECM stiffness.

Example 4

Figure 3:
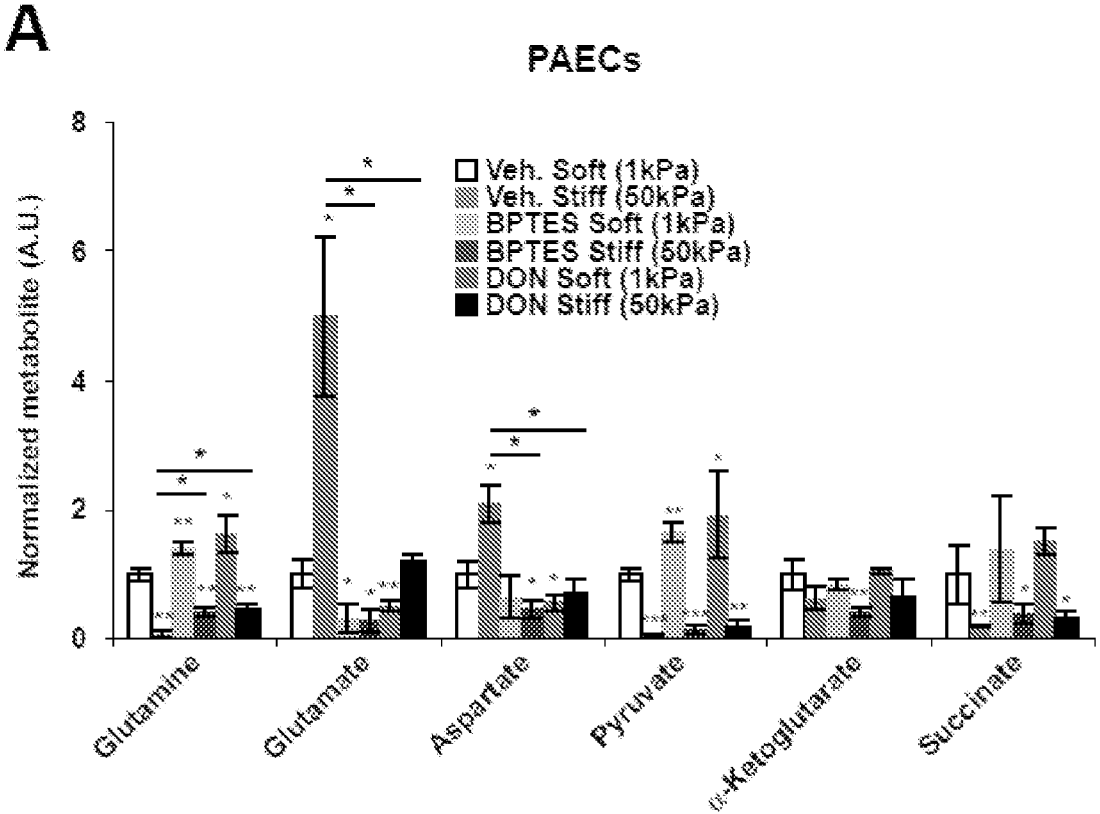
FIG. 3 (A-G) demonstrates pharmacologic or genetic inhibition of GLS blunts the up-regulation of glutaminolysis in stiff matrix. A-C) In PAECs, targeted LC-MS/MS revealed that pharmacologic inhibition of GLS (BPTES or DON) blunted the alterations of metabolite expression in stiff matrix. Specifically, compared with stiff matrix control (si-NC Stiff), GLS1 inhibition increased glutamine, pyruvate, and succinate, decreased glutamate and aspartate (A), and decreased lactate (B) as well as lactate/pyruvate ratio (C). D) Immunoblot analysis confirmed the knockdown of GLS1 by 2 independent siRNA sequences. E-G) In PAECs, GLS1 knockdown blunted the alterations of metabolite expression in stiff matrix, increasing glutamine, pyruvate, and succinate; decreasing glutamate and aspartate (E); and decreasing lactate/pyruvate ratio (F-G). In all panels, mean expression in control groups (soft matrix) was assigned a fold change of 1, to which relevant samples were compared. Data are expressed as mean±SD ($*P<0.05$; $P<0.01$, $*P<0.001$).
Figure 3:
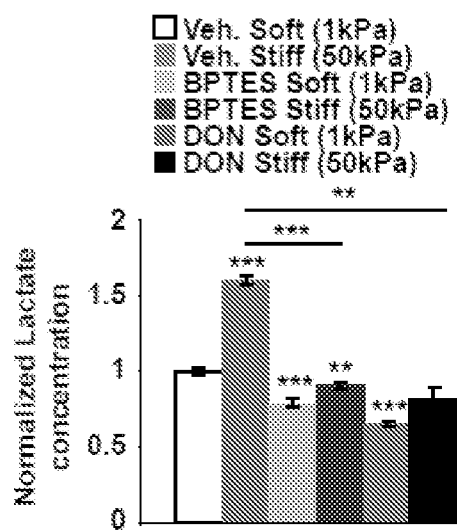
Figure 3:
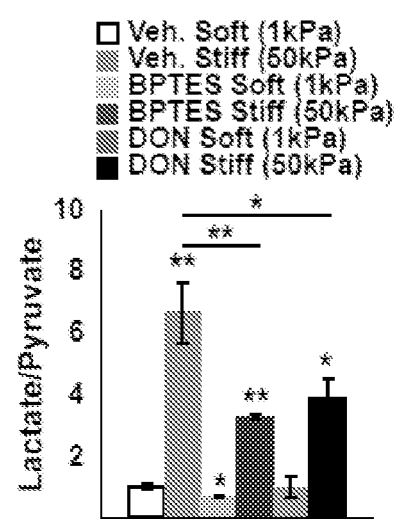
Figure 3:
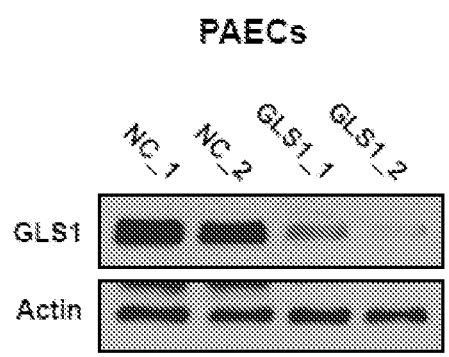
Figure 3:
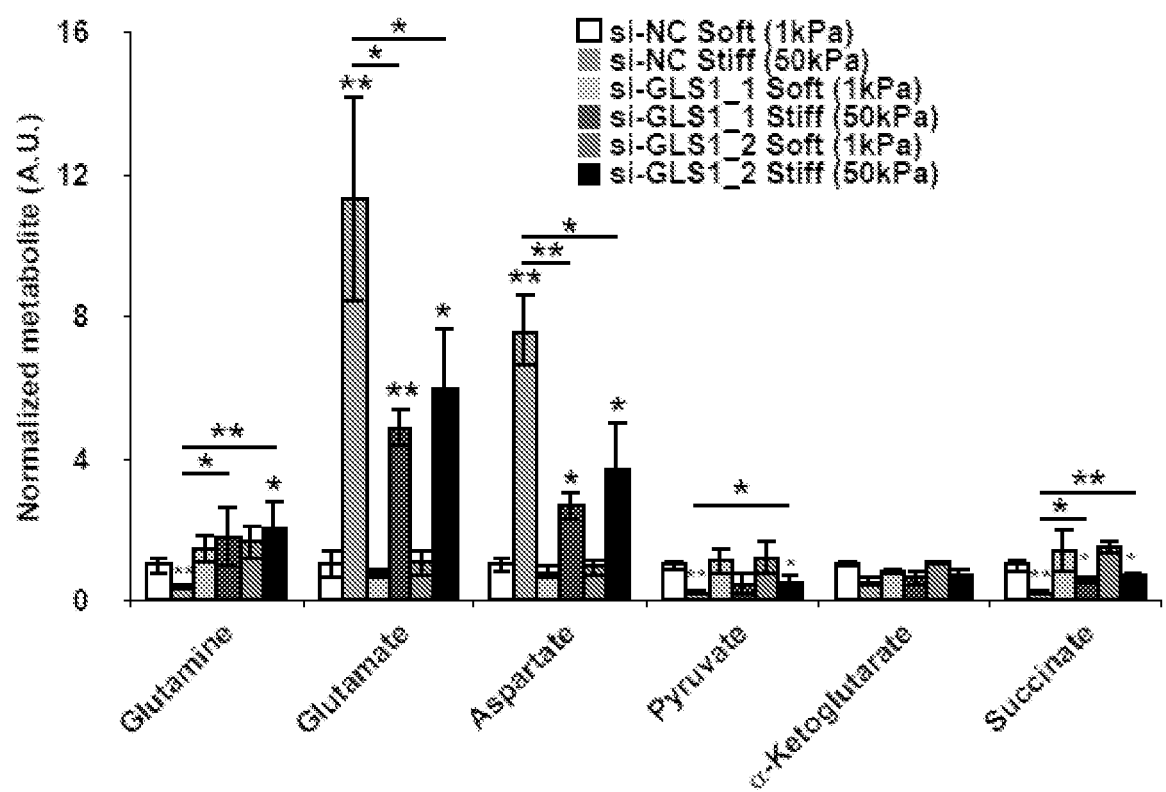
Figure 3:
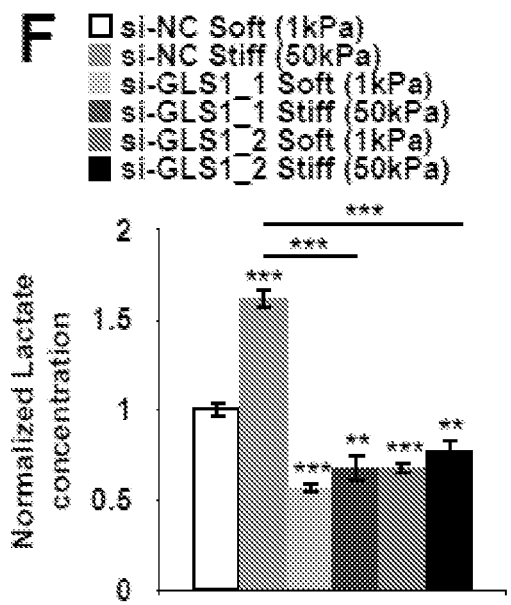
Figure 3:
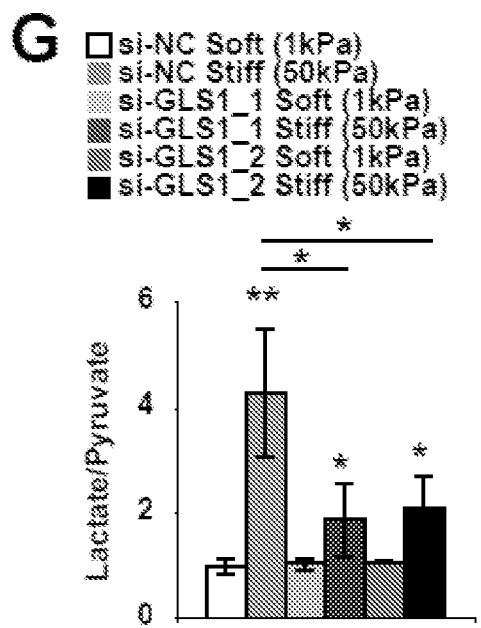

Increased GLS1 Expression and Glutaminolysis are Critical for Sustaining Glycolysis and Cell Proliferation in a Stiff Environment To determine whether GLS1 is critical for stiffness-induced and YAP/TAZ-dependent glutaminolysis, PAECs were cultivated in soft or stiff matrix, and exposed to known inhibitors of two isoforms of GLS1 (KGA and GAC), BPTES (Bis-2-(5-phenylacetamido-1,3,4-thiadiazol-2-yl) ethyl sulphide), DON (6-Diazo-5-oxo-L-norleucine), or CB-968 (glutaminase inhibitor, compound 968, C-968) (FIG. 3A-C) or siRNA (si-GLS; FIG. 3D-G). As quantified by LC-MS/MS, inhibition of GLS in PAECs blunted the stiffness-induced processes of glutamine consumption, glutamate production, and aspartate production (FIGS. 3A and E). GLS1 inhibition also decreased glycolysis in stiff matrix, as indicated by decreased lactate/pyruvate ratio (FIG. 3B-C, FIG. 3F-G). Similar alterations of metabolic activity were observed when inhibiting GLS1 in PASMCs (data not shown).

To identify downstream molecular processes regulated by GLS1, expression array analysis and pathway enrichment of PAECs exposed to si-GLS in stiff matrix cells revealed a systematic reprogramming of multiple pathways, notably down-regulating cell cycle genes controlling proliferative capacity and factors involved in extracellular matrix organization controlling cell migration (Table 1). As assessed by cell count, BrdU pulse, caspase 3/7 activity, and PCNA/cleaved caspase-3 double staining, GLS1 inhibition had a negligible effect on apoptosis and on proliferation in soft matrix but blunted proliferation in stiff matrix in PAECs (data not shown). Moreover, corresponding to the transcriptomic results affecting matrix organization, GLS inhibition, achieved via siRNA or pharmacologic means, inhibited cell migration (data not shown). Similar effects were observed in PASMCs (data not shown).

To investigate whether the anaplerotic production of glutamate and aspartate is central to the actions of GLS1 to sustain proliferation, glutamate or aspartate supplementation was performed in cells lacking GLS1 or YAP/TAZ. Consistent with these results and prior observations, siRNA knockdown of GLS1 or YAP/TAZ decreased proliferation in either PAECs or PASMCs, as assessed by cell count and quantitation of the proliferation marker, PCNA (data not shown). Importantly, in cells with diminished GLS1 or YAP/TAZ, cellular proliferation was at least partially restored by glutamate and more fully restored by aspartate supplementation (data not shown). Furthermore, aspartate supplementation similarly reversed the reduced cell migration of GLS1-deficient PAECs in stiff matrix (data not shown). Collectively, these results demonstrate that GLS1 and its control of glutamate and aspartate production by glutaminolysis are essential for metabolic reprogramming and consequent vascular cell proliferation and migration specific to stiff matrix exposure.

Example 5

The YAP/TAZ-GLS1 Axis Activates Glycolysis and Glutaminolysis in PAECs and PASMCs Exposed to Vascular Stiffness in Rodent and Human Instances of PH In Vivo In a rat model of inflammatory PAH (monocrotaline-induced), pulmonary arterial stiffening was recently described as an early pathological event accompanied by increased YAP/TAZ expression in diseased pulmonary arterioles. In this same monocrotaline rat model, it was determined whether glutaminolysis was activated and correlated with pulmonary arterial stiffness, YAP1 activation, and PAH. As previously reported, Picrosirius Red staining demonstrated an increase in fibrillar collagen deposition in diseased pulmonary arterioles derived from monocrotaline-exposed rats and correlated with an increase of pulmonary arteriolar stiffness, as demonstrated by atomic force microscopy (data not shown). These changes were accompanied by hemodynamic manifestations of PAH. From these rats, CD31+ endothelial cells were isolated from lungs three weeks after exposure to vehicle or monocrotaline, and metabolites were quantified by LC-MS/MS (data not shown). Consistent with observations of anaplerosis in cultured PAECs grown in stiff matrix, glutamine was decreased, and aspartate was increased in PAH CD31+ cells. Notably, no significant change in glutamate concentration was observed in these cells, which may suggest an elevated glutamate turnover in pulmonary cells in vivo. A decrease of succinate was also observed, indicative of a decrease in TCA cycle activity, and a glycolytic increase of the lactate/pyruvate ratio was present (data not shown). Consistent with such metabolite alterations, a significant increase of GLS1 expression in CD31+ cells was observed (data not shown). Immunoblotting also demonstrated a corresponding increase of GLS1, LDHA, and PC expression at the protein level in both CD31+ and CD31− cells from monocrotaline rat lungs (data not shown). In situ, confocal immunofluorescent microscopy revealed increased GLS1, PC, and LDHA staining in both CD31+ (endothelial) and α-SMA+ (smooth muscle) compartments of diseased pulmonary arterioles (data not shown).

Notably, up-regulation of GLS1, LDHA, and PC all correlated with increases of YAP1 nuclear localization and resultant up-regulation of PCNA+/Ki67+ proliferating cells in diseased pulmonary arterioles (data not shown). In order to determine the precise kinetics of these events during disease progression, in situ confocal immunofluorescent microscopy was performed at various stages of monocrotaline-induced PH in rats. Consistent with prior theories of endothelial apoptosis in PH, an early yet temporary induction of endothelial apoptosis was found as reflected by cleaved caspase-3 in situ staining and via caspase 3/7 activity (days 0-3 post-monocrotaline injection) (data not shown). This was then followed by a subsequent decrease of apoptosis and an increase of smooth muscle and endothelial cell proliferation, correlating with an increase of vascular GLS1 expression. Taken together, and consistent with in vitro findings, these results demonstrated that, following vascular injury and just after an early wave of endothelial apoptosis, the development of pulmonary vascular stiffness and glutaminolysis follows the same kinetics as the increase of proliferation of diseased endothelial and smooth muscle cells in vivo.

It was further questioned whether glutaminolytic reprogramming is an active process in human PAH to sustain pulmonary vascular cell proliferation. A cohort of human PAH patients (n=13) stemming from causes ranging from idiopathic and hereditary etiologies as well as scleroderma were studied (Table 2), and compared with non-PAH subjects (n=6) who died from traumatic or unrelated causes (2). Correlating with increased periarteriolar collagen remodeling in PAH cases, a concurrent up-regulation of GLS1, PC, and LDHA was observed in both CD31+ (endothelial) and α-SMA+ (smooth muscle) cells (data not shown). As with the PAH rats, GLS1 was increased simultaneously with YAP1 nuclear localization, and YAP1 nuclear localization correlated with increased PCNA+/Ki67+ proliferating vascular cells (data not shown). Similar observations were made in plexiform lesions—late stage vascular lesions where active proliferation and quiescent apoptosis were consistently observed (data not shown). Importantly, alterations of these metabolic enzymes correlated with metabolite profiles in circulating plasma, as assessed by LC-MS/MS in samples originating from the main pulmonary artery of PH individuals (mean pulmonary arterial pressure [mPAP]≥25 mmHg, patient demographic information in Table 3). In subjects with particularly high pulmonary arterial pressures (mean pulmonary pressure >45 mm Hg), lactate/pyruvate ratio was elevated reflective of increased glycolysis while glutamine/glutamate ratio was decreased and aspartate was increased, indicative of up-regulated glutaminolysis and anaplerosis, as compared with non-PH individuals (mPAP <25 mmHg, data not shown). Together, these results support the idea that vascular stiffening activates YAP/TAZ in order to induce a glutaminolytic metabolic switch and vascular proliferation in PAH across both rodent and human instances of disease in vivo.

Example 6

The YAP/TAZ-GLS1 Axis Induces Glycolysis and Glutaminolysis in Primates with SIV-PAH and in Persons with HIV-Induced PAH Because rodent models of PAH do not replicate all aspects of disease in humans, it was determined if this same molecular axis is active in a more relevant model organism without the use of a direct hypoxic stimulus. Previously, a non-human primate model of human immunodeficiency virus (HIV)-induced PAH was described in rhesus macaques infected with simian immunodeficiency virus (SIV). Importantly, such a model replicates the hemodynamic and histologic manifestations of PAH. It also displays an incomplete penetrance with 50-60% of infected macaques developing PAH, thus consistent with the incomplete penetrance of PAH with HIV infection in humans. Importantly, similar to the monocrotaline-exposed rats, in a cohort of SIV-infected macaques with confirmed hemodynamic and histologic manifestations of PAH, Picrosirius Red staining demonstrated an increase of periarteriolar fibrillar collagen as compared to non-PAH, SIV-infected animals (data not shown). Diseased pulmonary arterioles in SIV-PAH macaques also displayed increased GLS1, PC, and LDHA, correlating with increased YAP1 nuclear localization, proliferating PCNA+/Ki67+ cells, and non-apoptotic, cleaved caspase-3-negative cells (data not shown).

Finally, stemming from these findings in SIV-PAH macaques, it was determined whether humans suffering from HIV-PAH may also display signs of increased pulmonary vascular stiffness and consequent alterations in vascular glycolysis and glutaminolysis. A cohort of 42 HIV-infected individuals who underwent pulmonary arterial catheterization were studied, leading to a diagnosis of PAH in 11 individuals (Table 4). Analysis of invasive hemodynamic data of HIV-PAH subjects revealed a significant decrease of pulmonary arterial compliance consistent with an increase of pulmonary artery stiffness as compared with HIV-infected, non-PAH individuals. Importantly, by quantifying peripheral venous plasma metabolites from a separate cohort of HIV-infected persons with and without PAH (Table 4), an increase of lactate/pyruvate ratio was observed, indicative of increased glycolytic activity, while a decrease in glutamine/glutamate ratio and an increase in aspartate were consistent with up-regulation of glutaminolysis and anaplerosis in HIV-PAH (data not shown). Consequently, mirroring the molecular findings in rodent and other instances of human PAH, these observations of YAP/TAZ-GLS1 activation in HIV-PAH correlate with the tightly linked connection between pulmonary vascular stiffness and metabolic dysregulation.

Example 7

Modulation of Pulmonary Vascular Stiffness and YAP/TAZ-Dependent Mechanotransduction Regulates Glutaminolysis and PH Manifestation In Vivo To establish definitively whether periarteriolar ECM remodeling and YAP/TAZ modulate vascular cell metabolism in vivo, it was determined whether alteration of YAP/TAZ-dependent mechanotransduction directly controls glutaminolysis and PH development in the monocrotaline rat model. First, using a known pharmacologic inhibitor (β-aminoproprionitrile, BAPN) of Lox, the enzyme responsible for collagen crosslinking and consequent matrix stiffening, it was determined whether inhibition of ECM stiffening could prevent the metabolic changes and downstream PH manifestations observed in monocrotaline-exposed rats (FIG. 4A). BAPN treatment indeed decreased pulmonary Lox activity and consequent periarteriolar ECM stiffening, as assessed by atomic force microscopy (FIG. 4C-E), without adverse effects on left ventricular cardiac function (data not shown). Consistent with the in vitro results, reduction of ECM stiffening by BAPN led to a decrease of YAP1-dependent gene expression (FIG. 4E) and decreased downstream GLS activity, as reflected by direct enzymatic activity measurement and consequent alterations of metabolite expression (FIG. 4F-G). Such metabolic effects further decreased vascular endothelial and smooth muscle proliferation, as reflected by in situ arteriolar staining (FIG. 4G), and ameliorated hemodynamic and histologic manifestations of PH, as measured by vascular remodeling and muscularization (FIG. 4G), and right ventricular systolic pressure (RVSP) (FIG. 4H).

Second, in a parallel fashion, a known pharmacologic inhibitor (verteporfin) of YAP1 was used to interrogate whether YAP1 activity is also essential for activating vascular glutaminolysis and PH in this same rat model of disease (FIG. 4B). As expected, verteporfin decreased YAP1-dependent gene expression (FIG. 4E) without adverse effects on left ventricular cardiac function or systemic blood pressure (data not shown). Consequently, in a similar fashion to BAPN but to a much more robust degree, verteporfin improved the downstream metabolic (GLS1 expression and activity, FIG. 4F-G), proliferative (FIG. 4G), and end-stage manifestations of PH, including reductions in vascular remodeling/muscularization, RVSP, and right ventricular remodelling (Fulton index) (FIG. 4G-I). As a result, these data provide causative evidence in vivo that ECM stiffening relies upon YAP/TAZ-specific mechanotransduction in order to induce pulmonary vascular glutaminolysis and anaplerosis, proliferation, and PH.

Example 8

Figure 5:
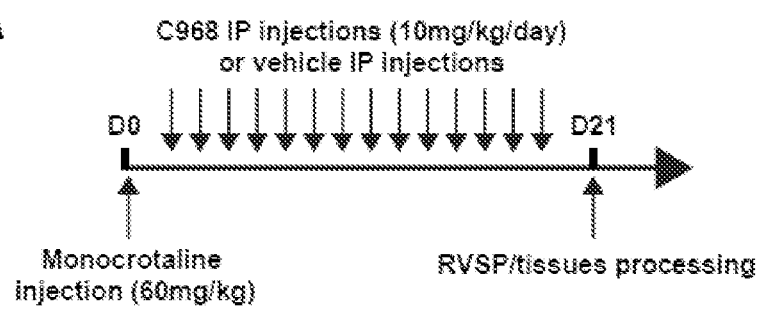
FIG. 5 (A-H) shows pharmacologic inhibition of GLS in monocrotaline-exposed rats decreased glutaminolysis and associated pulmonary vascular cells proliferation. After monocrotaline disease induction, rats were treated with daily intraperitoneal injections of vehicle, C968 or CB839, two pharmacological inhibitors of GLSas described in the schematics of the experimental protocol (A-B).C-D) Either C968 (C) or CB839 (D) decreased GLS activity in lungs of monocrotaline-exposed rats. E-H) Co-immunofluorescence microscopy revealed Ki67/PCNA-positive proliferating cells in diseased pulmonary arterioles (vehicle). Either C968 or CB839 reduced the number of Ki67/PCNA positive cells in α-SMA+ medial (G-H) and CD31/vWF+ endothelial (E-F) compartments. In all panels, mean expression in control groups was assigned a fold change of 1, to which relevant samples were compared. Data are expressed as mean±SEM ($*P<0.05$; $P<0.01$, $*P<0.001$). Scale bars, 50 µm.
Figure 5:
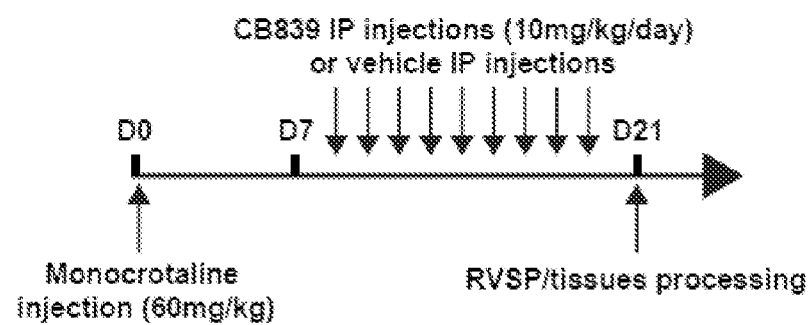
Figure 5:
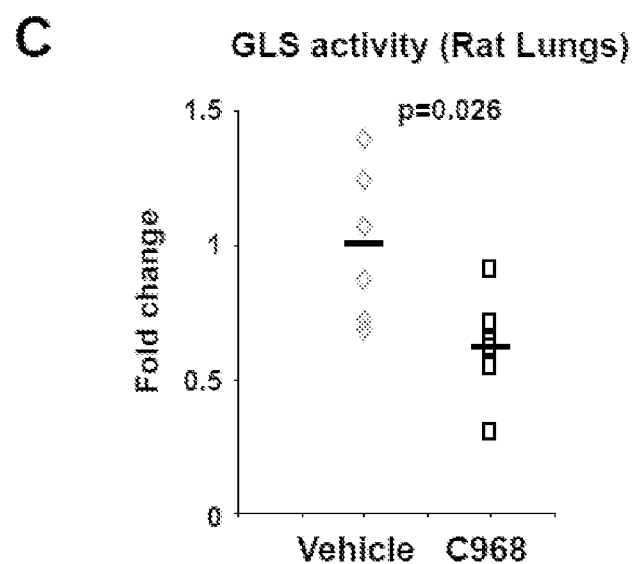
Figure 5:
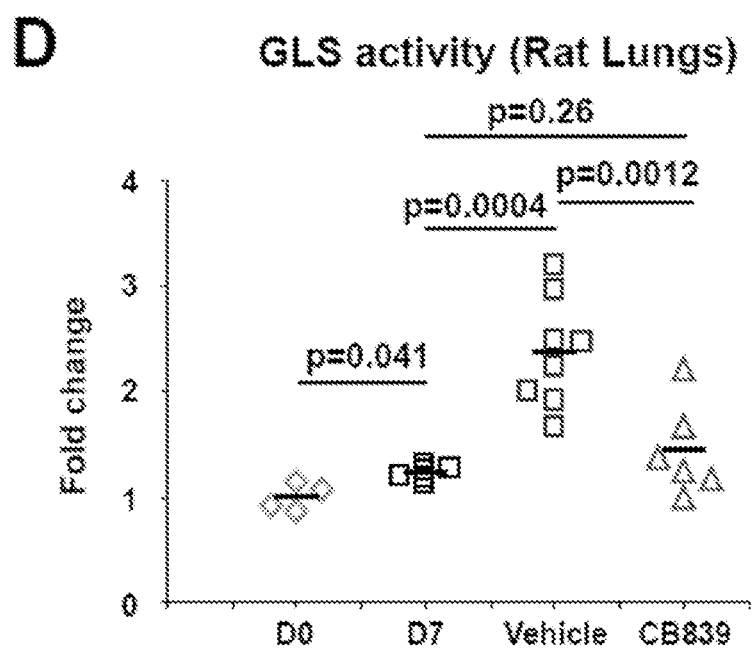
Figure 5:
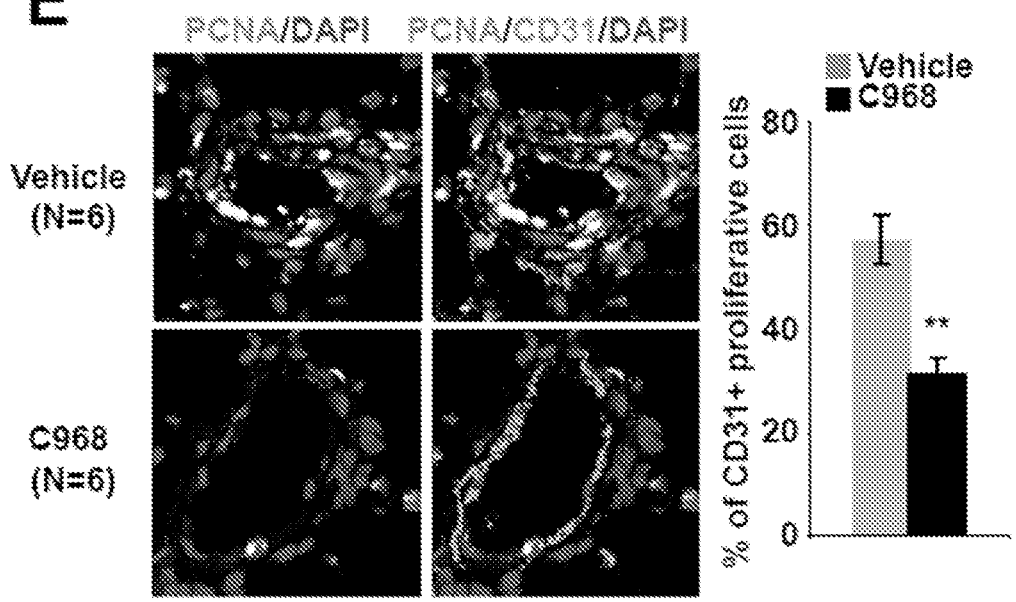
Figure 5:
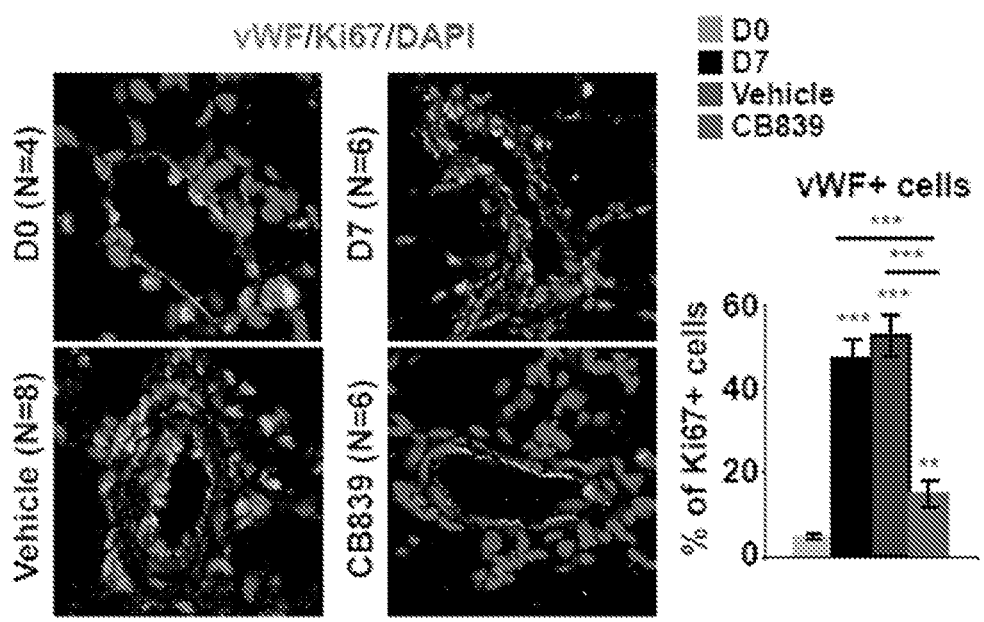
Figure 5:
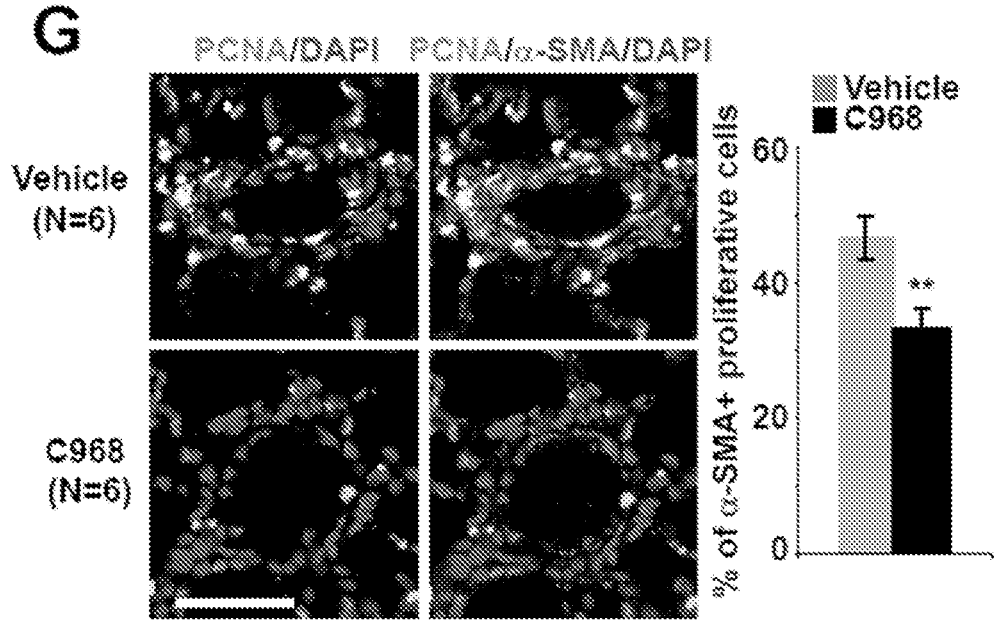
Figure 5:
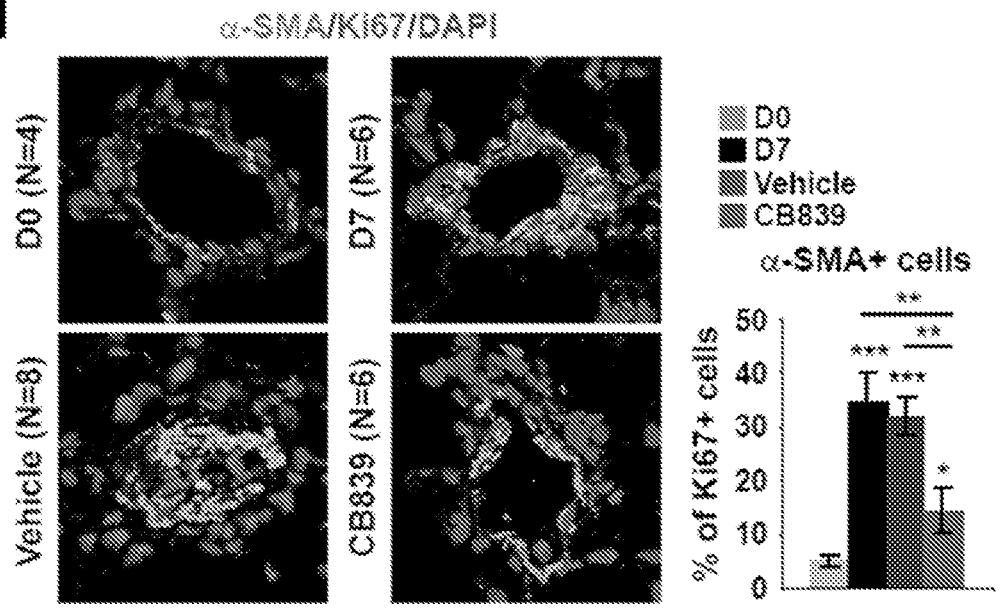

GLS1-Dependent Inhibition of Glutaminolysis Decreases Pulmonary Vascular Cell Proliferation In Vivo and Ameliorates PH Finally, to investigate whether glutaminolysis itself is essential for promoting pulmonary vascular proliferation in PH, two separate pharmacologic inhibitors of GLS1 (C968 and CB-839) were administered in monocrotaline-exposed rats using either a disease prevention (FIG. 5A) or disease reversal (FIG. 5B) dosing protocol. To induce PH, male Sprague-Dawley rats (10-14 week old) were injected intraperitoneally with 60 mg/kg monocrotaline (Sigma-Aldrich). After two days, serial intraperitoneal injections were given daily of C968 or CB-839 (10 mg/kg, Sigma-Aldrich), and after seven days post-monocrotaline injection, serial intraperitoneal injections were given daily of C968 or CB-839 (10 mg/kg, Selleck Chemicals). Two days after the last injection on day 21 post-monocrotaline injection, right heart catheterization was performed followed by harvest of lung tissue and CD31+ cells for RNA or protein extraction, paraffin embedding, or cryopreservation with OCT (Sigma-Aldrich), as described previously (Bertero T, et al. Cell Reports. 2015; 13(5):1016-32).

Figure 6:
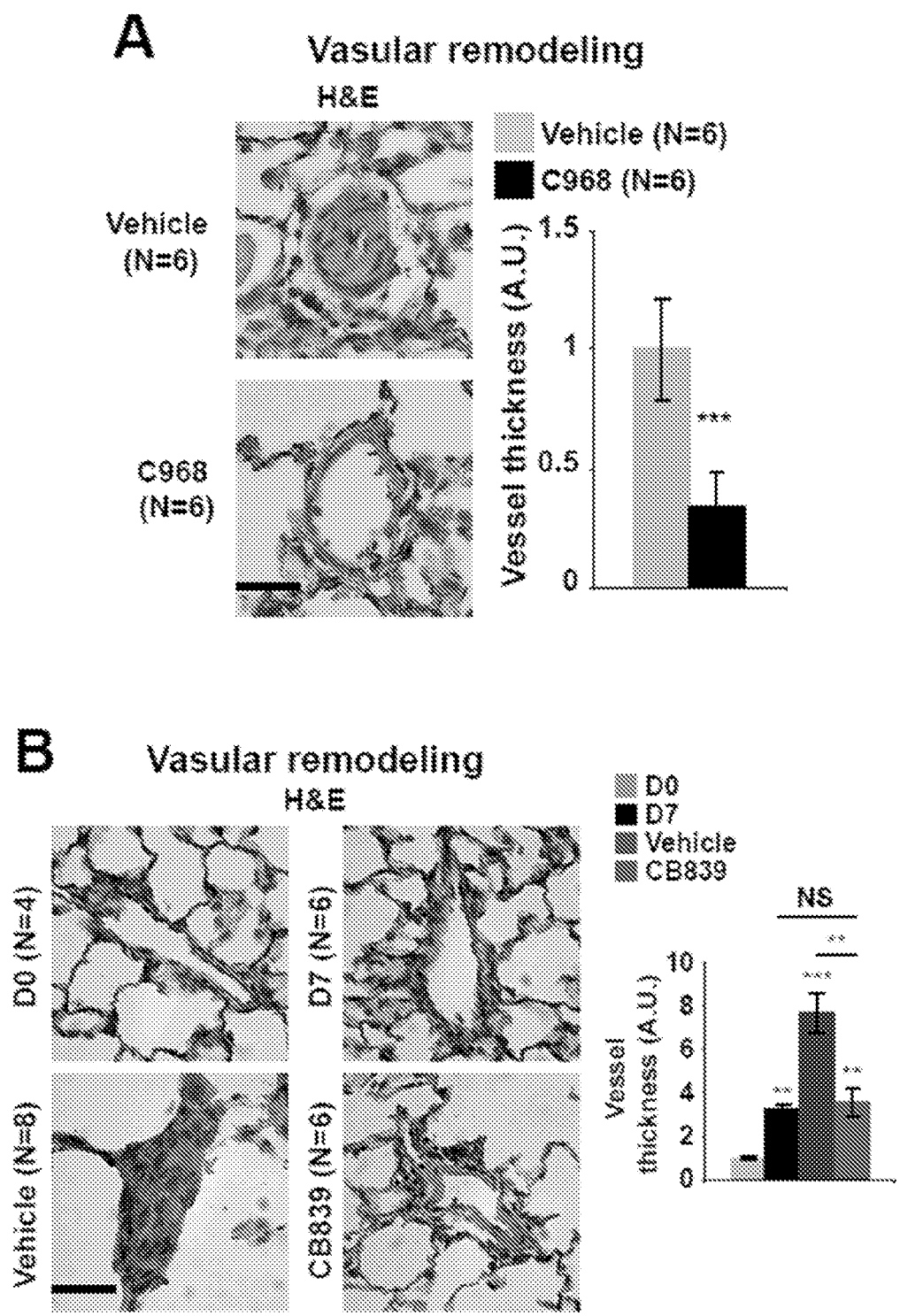
FIG. 6 (A-H) shows pharmacologic inhibition of GLS in monocrotaline-exposed rats improved PAH manifestations. Following monocrotaline injection in both prevention experiment (C968) or reversal study inhibition of glutaminolysis ameliorated PAH severity, as quantified by vascular remodeling (A-B), arteriolar muscularization (C-D), RVSP (E-G) and right ventricular hypertrophy (Fulton index, RV/LV+S) (H). In all panels, mean expression in control groups was assigned a fold change of 1, to which relevant samples were compared. Data are expressed as mean±SEM ($*P<0.05$; $P<0.01$, $*P<0.001$). Scale bars, 50 µm.
Figure 6:
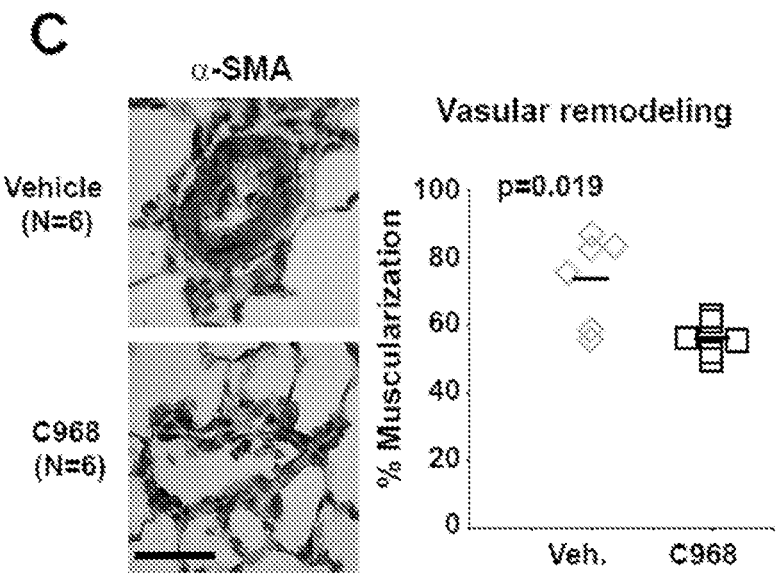
Figure 6:
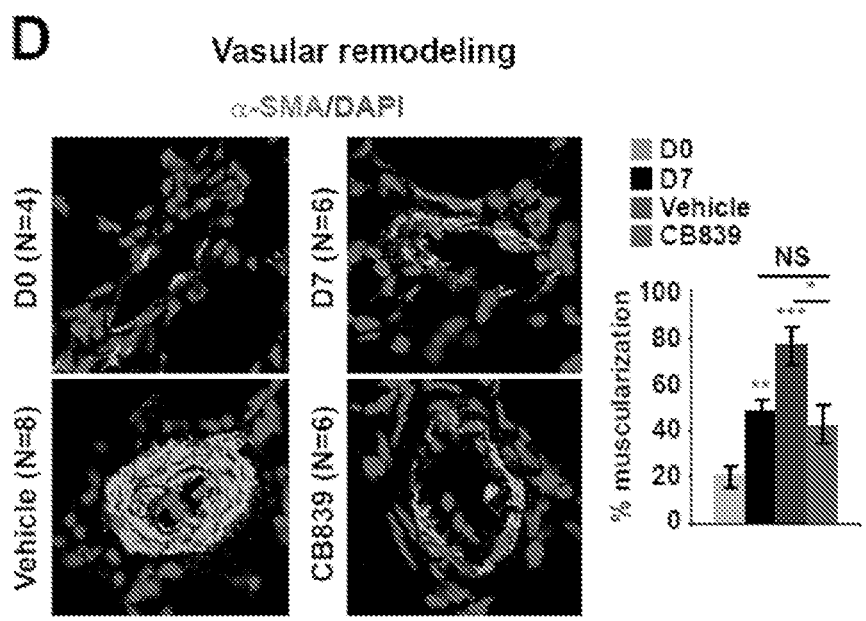
Figure 6:
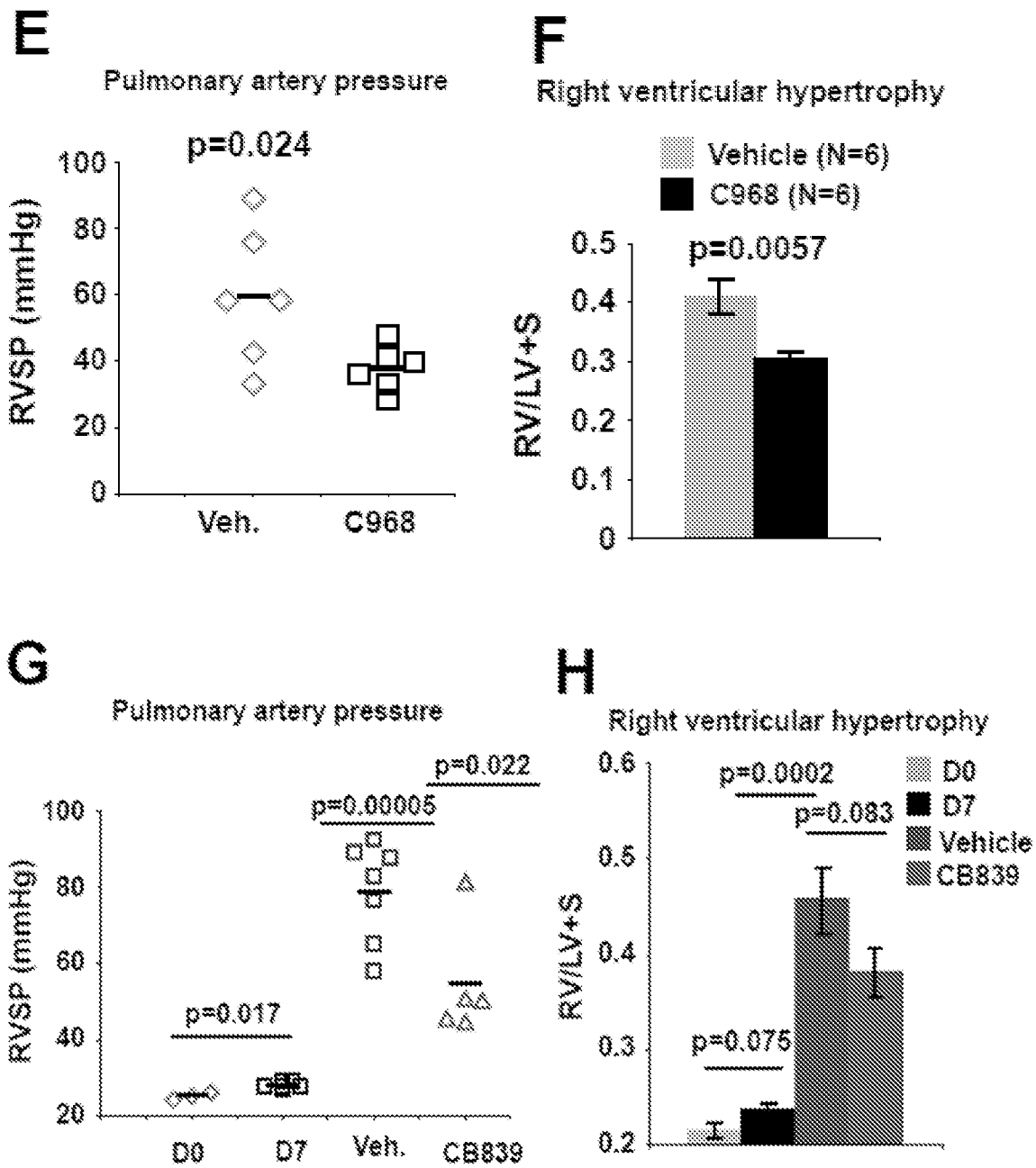
Figure 7:
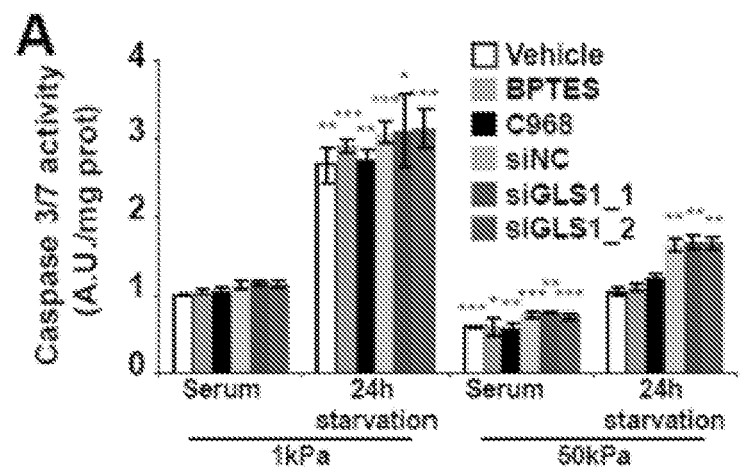
FIG. 7 (A-C) shows the genetic or pharmacologic inhibition of GLS1 controls PAEC proliferation but not apoptosis. A-C) PAECs were plated on soft (1 kPa) or stiff (50 kPa) matrix and exposed to indicated treatments. Apoptosis (A-C) and proliferation (B-C) were quantified 48 h after plating. A) Enzymatic assay revealed an increase of caspase 3/7 activity 24 h after serum depletion in soft matrix and, to a lesser extent, in stiff matrix. No significant changes were observed in the presence of pharmacological inhibitors of GLS1 (BPTES, C968) or after GLS1 knockdown by two independent siRNAs (si-GLS1_1, siGLS1_2) as compared with control treatments (Vehicle control; siRNA scrambled control, siNC). B-C) As revealed by immunofluorescent microscopy (B) and quantification (C), proliferation was increased by matrix stiffening (as reflected by PCNA+ stain) but was decreased by pharmacologic GLS1 inhibition. Apoptosis (as reflected by cleaved caspase-3 staining, CC-3+) was increased by serum starvation in both soft and stiff conditions but was not affected by GLS1 inhibition. In all panels, mean expression in control groups (soft matrix) was assigned a fold change of 1, to which relevant samples were compared. Data are expressed as mean±SD ($*P<0.05$; $P<0.01$, $*P<0.001$).
Figure 7:
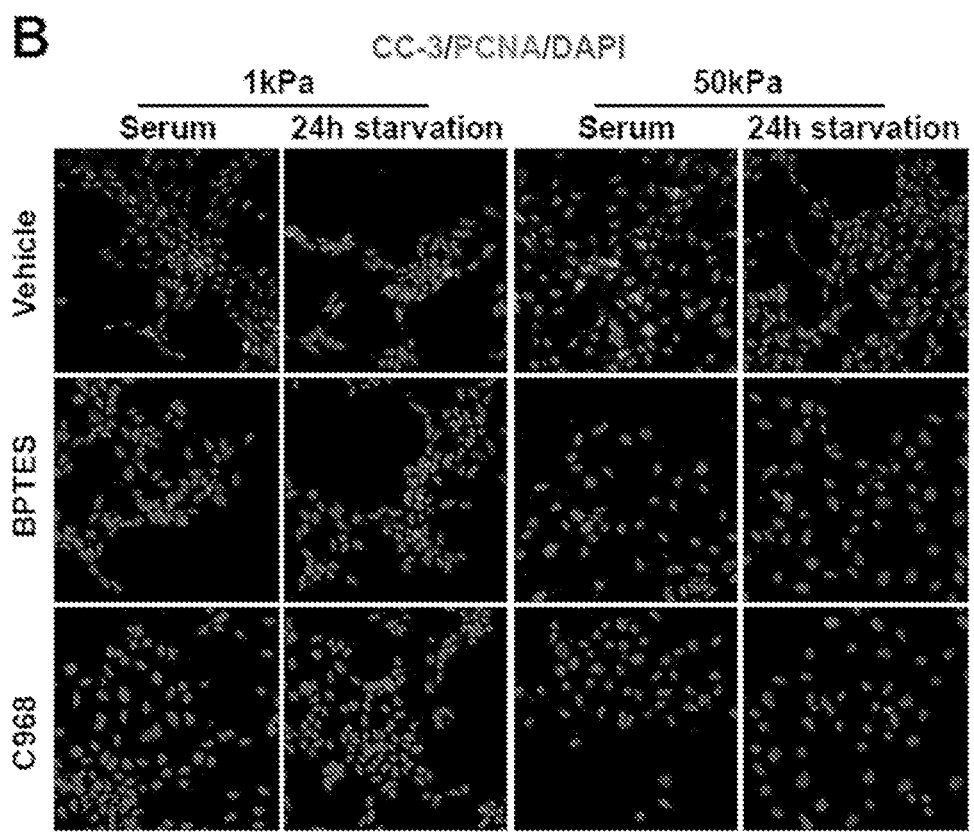
Figure 7:
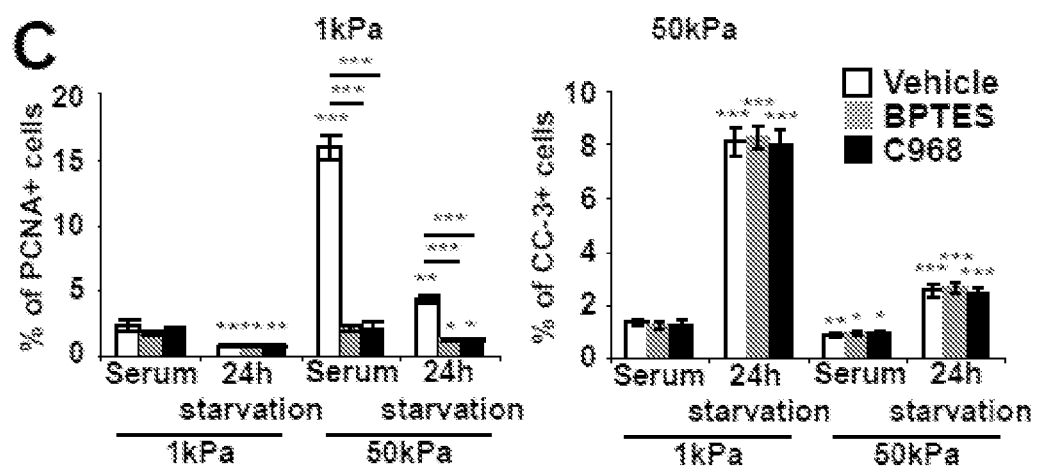

In both cases, C968 and CB-839 treatments decreased GLS1 activity in whole rat lung as compared with control (FIG. 5C-D) without adverse effects on left ventricular function or systemic blood pressure (data not shown). Correspondingly, C968 and CB-839 both decreased the presence of proliferation markers (PCNA+/Ki67+) in CD31+/vWF+ (endothelial) and α-SMA+ (smooth muscle) pulmonary arteriolar cells as compared with control PH rats (FIG. 5E-H). As a result, both C968 and CB-839 significantly decreased pulmonary arteriolar remodeling (FIG. 6A-B) and muscularization (FIG. 6C-D), right ventricular systolic pressure (RVSP) (FIG. 6E, FIG. 6G), and right ventricular remodeling (FIG. 6F, FIG. 6H). Taken together, these results directly implicate GLS1 and glutaminolysis, a process dependent upon ECM stiffening, as critical metabolic mediators necessary for sustaining pulmonary vascular proliferation in PH.

TABLE 1

Pathway enrichment of PAECs genes differentially expressed in response to GLS knockdown in stiff matrix.

| Pathway | Pathway Size | Overlap Size | pval | FDR | Overlapping Genes (Up) | Overlapping Genes (Down) |
|---|---|---|---|---|---|---|
| NF-kappa B signaling pathway (KEGG) | 91 | 9 | <0.0001 | 2.67E−03 | LY96 | PTGS2 CXCL2 IL8 CXCL12 BCL2A1 TNFAIP3 DDX58 VCAM1 |
| Extracellular matrix organization (Reactome) | 263 | 16 | <0.0001 | 3.00E−03 | ADAM9 ADAM17 NID2 | LTBP1 PLOD2 ADAMTS1 LAMC2 FGF2 VCAN FBLN5 TGFB2 SDC4 VCAM1 FBN2 COL8A1 COL5A2 |
| Malaria (KEGG) | 49 | 7 | <0.0001 | 3.00E−03 | — | CSF3 THBS2 IL8 SELE TGFB2 CCL2 VCAM1 |
| TNF signaling pathway (KEGG) | 110 | 9 | 0.0001 | 9.00E−03 | — | PTGS2 VEGFC CXCL1 CXCL2 SELE CXCL10 TNFAIP3 CCL2 VCAM1 |
| Beta5 beta6 beta7 and beta8 integrin cell surface interactions (NCBI) | 17 | 4 | 0.0002 | 1.76E−02 | — | EDIL3 PLAUR CYR61 VCAM1 |
| NOD-like receptor signaling pathway (KEGG) | 57 | 6 | 0.0003 | 2.52E−02 | — | CXCL1 CXCL2 IL8 TNFAIP3 CCL2 PYDC1 |
| Interferon alpha/beta | 63 | 6 | 0.0005 | 3.57E−02 | GBP2 | OASL MX2 EGR1 IFIT2 |

TABLE 1-continued

Pathway enrichment of PAECs genes differentially expressed in response to GLS knockdown in stiff matrix.

| Pathway | Pathway Size | Overlap Size | pval | FDR | Overlapping Genes (Up) | Overlapping Genes (Down) |
|---|---|---|---|---|---|---|
| signaling (Reactome) | | | | | | IFIT1 |
| E2F transcription factor network (NCBI) | 68 | 6 | 0.0007 | 4.69E-02 | — | MYBL2 CCNE1 RBBP8 RRM2 TYMS CDC25A |
| Cytokine-cytokine receptor interaction (KEGG) | 265 | 12 | 0.0009 | 5.17E-02 | — | VEGFC CXCL1 CSF3 CXCL2 IL8 TNFSF15 CXCL11 CXCL12 TGFB2 CXCL10 CCL2 TNFSF10 |
| Mitotic G1-G1/S phases (Reactome) | 134 | 8 | 0.0012 | 6.55E-02 | — | MYBL2 CCNE1 CDC7 RRM2 PSMD10 WEE1 TYMS CDC25A |
| ATF-2 transcription factor network (NCBI) | 58 | 5 | 0.0021 | 1.11E-01 | — | IL8 DUSP5 DUSP1 SELE TGFB2 |
| Cell Cycle Checkpoints (Reactome) | 118 | 7 | 0.0024 | 1.07E-01 | UBE2D1 | MAD2L1 CCNE1 CDC7 PSMD10 WEE1 CDC25A |
| Validated transcriptional targets of AP1 family members Fra1 and Fra2 (NCBI) | 36 | 4 | 0.0024 | 1.15E-01 | HMOX1 | PLAUR IL8 CCL2 |
| Beta1 integrin cell surface interactions (NCBI) | 66 | 5 | 0.0037 | 1.48E-01 | — | PLAUR LAMC2 THBS2 VCAM1 COL5A2 |
| Beta3 integrin cell surface interactions (NCBI) | 43 | 4 | 0.0045 | 1.68E-01 | — | EDIL3 PLAUR CYR61 SDC4 |
| AP-1 transcription factor network (NCBI) | 70 | 5 | 0.0047 | 1.63E-01 | — | CYR61 IL8 DUSP1 CCL2 EGR1 |
| Alpha9 beta1 integrin signaling events (NCBI) | 24 | 3 | 0.0062 | 2.08E-01 | — | VEGFC SAT1 VCAM1 |
| Amoebiasis (KEGG) | 109 | 6 | 0.007 | 2.22E-01 | SERPINB9 | LAMC2 CXCL1 IL8 TGFB2 COL5A2 |
| Metabolism of amino acids and derivatives (Reactome) | 147 | 7 | 0.0079 | 2.38E-01 | ENOPH1 NQO1 GCLM | PSMD10 PHGDH GLS SAT1 |
| BARD1 signaling events (NCBI) | 29 | 3 | 0.0104 | 2.86E-01 | — | CCNE1 RBBP8 BARD1 |
| Beta2 integrin cell surface interactions (NCBI) | 29 | 3 | 0.0104 | 2.86E-01 | — | PLAUR CYR61 VCAM1 |
| VEGF and VEGFR signaling network (NCBI) | 10 | 2 | 0.0106 | 2.66E-01 | PGF | VEGFC |
| Signaling by VEGF (Reactome) | 10 | 2 | 0.0106 | 2.66E-01 | PGF | VEGFC |
| ECM-receptor interaction (KEGG) | 86 | 5 | 0.0109 | 2.62E-01 | — | LAMC2 THBS2 RELN SDC4 COL5A2 |
| Cell cycle (KEGG) | 124 | 6 | 0.0126 | 2.90E-01 | — | MAD2L1 CCNE1 CDC7 TGFB2 WEE1 CDC25A |
| Rheumatoid arthritis (KEGG) | 90 | 5 | 0.013 | 2.87E-01 | — | CXCL1 IL8 CXCL12 TGFB2 CCL2 |
| Syndecan-4-mediated signaling events (NCBI) | 32 | 3 | 0.0135 | 2.85E-01 | — | FGF2 CXCL12 SDC4 |

TABLE 1-continued

Pathway enrichment of PAECs genes differentially expressed in response to GLS knockdown in stiff matrix.

| Pathway | Pathway Size | Overlap Size | pval | FDR | Overlapping Genes (Up) | Overlapping Genes (Down) |
|---|---|---|---|---|---|---|
| ATM pathway (NCBI) | 34 | 3 | 0.0158 | 3.20E−01 | — | XRCC4 RBBP8 CDC25A |
| Interferon gamma signaling (Reactome) | 63 | 4 | 0.0166 | 3.23E−01 | GBP2 | OASL GBP1 VCAM1 |
| PI3K-Akt signaling pathway (KEGG) | 346 | 11 | 0.0181 | 3.41E−01 | PGF PPP2R3A | VEGFC LAMC2 FGF5 CCNE1 FGF2 CSF3 THBS2 RELN COL5A2 |
| ErbB1 downstream signaling (NCBI) | 100 | 5 | 0.0195 | 3.57E−01 | F2RL2 | ZFP36 DUSP1 DIAPH3 EGR1 |
| Extrinsic Pathway for Apoptosis (Reactome) | 14 | 2 | 0.0199 | 3.53E−01 | ADAM17 | TNFSF10 |
| p53 signaling pathway (KEGG) | 68 | 4 | 0.0212 | 3.66E−01 | ZMAT3 | CCNE1 RRM2 PMAIP1 |
| Pyrimidine metabolism (KEGG) | 105 | 5 | 0.0235 | 3.91E−01 | TK2 | CDA RRM2 PNPT1 TYMS |
| Cell adhesion molecules (CAMs) (KEGG) | 143 | 6 | 0.0236 | 3.81E−01 | — | VCAN SELE CD274 SDC4 CDH2 VCAM1 |
| ISG15 antiviral mechanism (Reactome) | 71 | 4 | 0.0244 | 3.82E−01 | — | HERC5 MX2 DDX58 IFIT1 |
| Chemokine signaling pathway (KEGG) | 189 | 7 | 0.0272 | 4.10E−01 | — | CXCL1 CXCL2 IL8 CXCL11 CXCL12 CXCL10 CCL2 |
| RIG-I/MDA5 mediated induction of IFN-alpha/beta pathways (Reactome) | 79 | 4 | 0.0341 | 4.87E−01 | UBE2D1 | HERC5 TNFAIP3 DDX58 |
| Calcineurin-regulated NFAT-dependent transcription in lymphocytes (NCBI) | 46 | 3 | 0.0344 | 4.66E−01 | — | PTGS2 IL8 EGR1 |
| FGF signaling pathway (NCBI) | 46 | 3 | 0.0344 | 4.66E−01 | — | PLAUR SPRY2 CDH2 |
| Sprouty regulation of tyrosine kinase signals (Biocarta) | 19 | 2 | 0.0349 | 4.50E−01 | — | SPRY4 SPRY2 |
| Cholesterol biosynthesis (Reactome) | 19 | 2 | 0.0349 | 4.50E−01 | HMGCS1 DHCR24 | — |
| GPCR ligand binding (Reactome) | 433 | 12 | 0.0351 | 4.42E−01 | F2RL2 | HTR1B CXCL1 CXCL2 IL8 CXCL11 CXCL12 CXCL10 CCL2 P2RY1 PTGER4 ADRB2 |
| TGF-beta signaling pathway (KEGG) | 80 | 4 | 0.0354 | 4.34E−01 | — | LTBP1 GDF6 FST TGFB2 |
| Segmentation clock (Biocarta) | 21 | 2 | 0.0418 | 4.95E−01 | ADAM17 | DKK2 |
| Inhibition of matrix metalloproteinases (Biocarta) | 3 | 1 | 0.0449 | 5.25E−01 | — | RECK |
| Double-Strand Break Repair (Reactome) | 22 | 2 | 0.0454 | 5.20E−01 | — | XRCC4 BRIP1 |
| Axon guidance (KEGG) | 127 | 5 | 0.0468 | 5.30E−01 | — | SEMA6D SEMA3C SEMA3A SLIT2 CXCL12 |

TABLE 1-continued

Pathway enrichment of PAECs genes differentially expressed
in response to GLS knockdown in stiff matrix.

| Pathway | Pathway Size | Overlap Size | pval | FDR | Overlapping Genes (Up) | Overlapping Genes (Down) |
|---|---|---|---|---|---|---|
| Signaling by EGFR (Reactome) | 171 | 6 | 0.049 | 5.48E-01 | ADAM17 TNRC6A | FGF5 FGF2 ITPR2 SPRY2 |
| Signaling events mediated by PRL (NCBI) | 23 | 2 | 0.0491 | 5.38E-01 | — | CCNE1 EGR1 |

Pathway enrichment performed by Reactome FI tool (1) incorporating data from KEGG, Reactome, NCBI, and Biocarta databases.

TABLE 2

Clinical characteristics of PAH patients used for in situ staining.

| Age | Gender | mPAP (mmHg) | Clinical description |
|---|---|---|---|
| 34 | Female | 50 | Cardiopulmonary arrest (autopsy), Idiopathic |
| 64 | Female | 55 | Cardiopulmonary arrest (autopsy), Idiopathic |
| 68 | Female | 44 | Bilateral lung transplant, Scleroderma |
| 12 | Male | 53 | Bilateral lung transplant, BMPRII mutation |
| 16 | Male | 62 | Bilateral lung transplant, Idiopathic |
| 1 | Male | 50 | Lung resection, Trisomy 21 |
| 19 | Male | 48 | Lung resection, Idiopathic |
| 51 | Male | 48 | Lung transplant, Scleroderma |
| 42 | Female | 57 | Lung transplant, Scleroderma |
| 67 | Male | 50 | Lung transplant, Scleroderma |
| 60 | Female | 66 | Autopsy Scleroderma |
| 54 | Female | 54 | Autopsy Scleroderma |
| 72 | Female | 53 | Autopsy Scleroderma |

TABLE 3

Clinical characteristics of PH patients from whom plasma
was drawn for metabolite profiling from the main pulmonary
artery during pulmonary arterial catheterization.

| Age (Year) | Gender | mPAP (mmHg) | PVR (dynes · sec · cm$^{-5}$) |
|---|---|---|---|
| 73 | Female | 37 | 481 |
| 88 | Female | 46 | 631 |
| 65 | Female | 49 | 789 |
| 44 | Female | 46 | 387 |
| 67 | Female | 45 | 607 |
| 83 | Male | 54 | 926 |
| 81 | Female | 52 | 1031 |
| 52 | Male | 56 | 522 |
| 78 | Female | 51 | 960 |
| 67 | Female | 49 | 560 |
| 88 | Female | 45 | 542 |
| 56 | Male | 56 | 1396 |
| 67 | Female | 57 | 658 |
| 81 | Female | 42 | 663 |
| 23 | Male | 40 | 957 |
| 78 | Female | 44 | 536 |
| 79 | Female | 56 | 897 |
| 80 | Male | 50 | 826 |
| 78 | Male | 43 | 803 |

Mean pulmonary arterial pressure (mPAP), pulmonary vascular resistance (PVR).

TABLE 4

Clinical characteristics of HIV-infected individuals
analyzed for pulmonary arterial compliance by invasive
pulmonary arterial catheterization.

| Variable | No PAH (n = 31) | PAH (n = 11) | p-value |
|---|---|---|---|
| Age, median (IQR) | 54 (46, 61) | 45 (41, 54) | 0.14 |
| Age, mean ± SD | 53 ± 11 | 47 ± 9 | 0.11 |
| Males, n (%) | 25 (80.6) | 7 (63.6) | 0.25 |
| Caucasian, n (%) | 19 (61.3) | 5 (45.5) | 0.36 |
| African-American, n (%) | 12 (38.7) | 6 (54.5) | |
| Ever smoker, n (%) | 16 (55.2) | 7 (77.8) | 0.23 |
| Systemic hypertension, n (%) | 14 (48.3) | 1 (11.1) | 0.046 |
| Coronary artery disease, n (%) | 7 (23.3) | 0 (0.0) | 0.11 |
| Hepatic disease, n (%) | 8 (26.7) | 2 (20.0) | 0.673 |
| COPD, n (%) | 5 (16.7) | 1 (11.1) | 0.685 |
| mPAP mmHg, median (IQR) | 20 (17, 30) | 37 (31, 52) | <0.001 |
| PCWP mmHg, median (IQR) | 13 (9, 21) | 11 (7, 13) | 0.2 |
| PVR woods unit, median (IQR) | 1.4 (1, 1.9) | 3.9 (3.5, 10.8) | <0.001 |
| PVR ≥ 3 woods unit, n (%) | 3 (12) | 10 (91) | <0.001 |
| EF ≤ 45%, n (%) | 4 (13.3) | 1 (9) | 0.71 |
| Diastolic Dysfunction, n (%) | 7 (26) | 2 (20) | 0.7 |

Ejection fraction (EF);
interquartile range (IQR);
mean pulmonary artery pressure (mPAP);
pulmonary arterial hypertension (PAH);
pulmonary capillary wedge pressure (PCWP);
pulmonary vascular resistance (PVR)

TABLE 5

Hemodynamic measurements of HIV-infected individuals
with PAH from whom peripheral venous plasma
was drawn for metabolite profiling.

| Age (Year) | mPAP (mmHg) | PASP (mmHg) |
|---|---|---|
| 44 | 35 | 81 |
| 37 | 37 | 63 |
| 36 | 38 | 74 |
| 60 | 47 | 60 |
| 35 | 51 | 67 |
| 37 | 53 | 84 |
| 48 | 55 | 73 |
| 45 | 56 | 73 |
| 41 | 58 | 71 |

Mean pulmonary artery pressure (mPAP, as measured by invasive hemodynamics); pulmonary arterial systolic pressure (PASP, as estimated by echocardiography).

SEQUENCES

SEQ ID NO: 1

MNPASAPPPL PPPGQQVIHV TQDLDTDLEA LFNSVMNPKP

SSWRKKILPE SFFKEPDSGS HSRQSSTDSS GGHPGPRLAG

-continued

```
GAQHVRSHSS PASLQLGTGA GAAGSPAQQH AHLRQQSYDV

TDELPLPPGW EMTFTATGQR YFLNHIEKIT TWQDPRKAMN

QPLNHMNLHP AVSSTPVPQR SMAVSQPNLV MNHQHQQQMA

PSTLSQQNHP TQNPPAGLMS MPNALTTQQQ QQQKLRLQRI

QMERERIRMR QEELMRQEAA LCRQLPMEAE TLAPVQAAVN

PPTMTPDMRS ITNNSSDPFL NGGPYHSREQ STDSGLGLGC

YSVPTTPEDF LSNVDEMDTG ENAGQTPMNI NPQQTRFPDF

LDCLPGTNVD LGTLESEDLI PLFNDVESAL NKSEPFLTWL

SEQ ID NO: 2
MDPGQQPPPQ PAPQGQGQPP SQPPQGQGPP SGPGQPAPAA

TQAAPQAPPA GHQIVHVRGD SETDLEALFN AVMNPKTANV

PQTVPMRLRK LPDSFFKPPE PKSHSRQAST DAGTAGALTP

QHVRAHSSPA SLQLGAVSPG TLTPTGVVSG PAATPTAQHL

RQSSFEIPDD VPLPAGWEMA KTSSGQRYFL NHIDQTTTWQ

DPRKAMLSQM NVTAPTSPPV QQNMMNSASG PLPDGWEQAM

TQDGEIYYIN HKNKTTSWLD PRLDPRFAMN QRISQSAPVK

QPPPLAPQSP QGGVMGGSNS NQQQQMRLQQ LQMEKERLRL

KQQELLRQAM RNINPSTANS PKCQELALRS QLPTLEQDGG

TQNPVSSPGM SQELRTMTTN SSDPFLNSGT YHSRDESTDS

GLSMSSYSVP RTPDDFLNSV DEMDTGDTIN QSTLPSQQNR

FPDYLEAIPG TNVDLGTLEG DGMNIEGEEL MPSLQEALSS

DILNDMESVL AATKLDKESF LTWL

SEQ ID NO: 3
MMRLRGSGML RDLLLRSPAG VSATLRRAQP LVTLCRRPRG

GGRPAAGPAA AARLHPWWGG GGWPAEPLAR GLSSSPSEIL

QELGKGSTHP QPGVSPPAAP AAPGPKDGPG ETDAFGNSEG

KELVASGENK IKQGLLPSLE DLLFYTIAEG QEKIPVHKFI

TALKSTGLRT SDPRLKECMD MLRLTLQTTS DGVMLDKDLF

KKCVQSNIVL LTQAFRRKFV IPDFMSFTSH IDELYESAKK

QSGGKVADYI PQLAKFSPDL WGVSVCTVDG QRHSTGDTKV

PFCLQSCVKP LKYAIAVNDL GTEYVHRYVG KEPSGLRFNK

LFLNEDDKPH NPMVNAGAIV VTSLIKQGVN NAEKFDYVMQ

FLNKMAGNEY VGFSNATFQS ERESGDRNFA IGYYLKEKKC

FPEGTDMVGI LDFYFQLCSI EVTCESASVM AATLANGGFC

PITGERVLSP EAVRNTLSLM HSCGMYDFSG QFAFHVGLPA

KSGVAGGILL VVPNVMGMMC WSPPLDKMGN SVKGIHFCHD

LVSLCNFHNY DNLRHFAKKL DPRREGGDQR VKSVINLLFA

AYTGDVSALR RFALSAMDME QRDYDSRTAL HVAAAEGHVE

VVKFLLEACK VNPFPKDRWN NTPMDEALHF GHHDVFKILQ

EYQVQYTPQG DSDNGKENQT VHKNLDGLL
```

The invention claimed is:

1. A method of treating a pulmonary vascular disease in a subject comprising administering to the subject a therapeutically effective amount of verteporfin, a salt, prodrug, or derivative thereof and C968 or CB-839; or a salt, prodrug, or derivative thereof.

2. The method of claim 1, wherein the pulmonary vascular disease is a pulmonary hypertension.

3. The method of claim 1, wherein the pulmonary vascular disease is a pulmonary arterial hypertension.

4. A method of reducing pulmonary vascular stiffness in a subject comprising administering to the subject a therapeutically effective amount of verteporfin, a salt, prodrug, or derivative thereof and C968 or CB-839; or a salt, prodrug, or derivative thereof.

* * * * *

SEQUENCE LISTING

<160> NUMBER OF SEQ ID NOS: 3

<210> SEQ ID NO 1
<211> LENGTH: 400
<212> TYPE: PRT
<213> ORGANISM: Homo sapiens

<400> SEQUENCE: 1

```
Met Asn Pro Ala Ser Ala Pro Pro Leu Pro Pro Gly Gln Gln
1               5                   10                  15

Val Ile His Val Thr Gln Asp Leu Asp Thr Asp Leu Glu Ala Leu Phe
            20                  25                  30

Asn Ser Val Met Asn Pro Lys Pro Ser Ser Trp Arg Lys Lys Ile Leu
        35                  40                  45

Pro Glu Ser Phe Phe Lys Glu Pro Asp Ser Gly Ser His Ser Arg Gln
    50                  55                  60

Ser Ser Thr Asp Ser Ser Gly Gly His Pro Gly Pro Arg Leu Ala Gly
65                  70                  75                  80

Gly Ala Gln His Val Arg Ser His Ser Ser Pro Ala Ser Leu Gln Leu
                85                  90                  95

Gly Thr Gly Ala Gly Ala Ala Gly Ser Pro Ala Gln Gln His Ala His
            100                 105                 110

Leu Arg Gln Gln Ser Tyr Asp Val Thr Asp Glu Leu Pro Leu Pro Pro
        115                 120                 125

Gly Trp Glu Met Thr Phe Thr Ala Thr Gly Gln Arg Tyr Phe Leu Asn
    130                 135                 140
```

```
His Ile Glu Lys Ile Thr Thr Trp Gln Asp Pro Arg Lys Ala Met Asn
145                 150                 155                 160

Gln Pro Leu Asn His Met Asn Leu His Pro Ala Val Ser Ser Thr Pro
                165                 170                 175

Val Pro Gln Arg Ser Met Ala Val Ser Gln Pro Asn Leu Val Met Asn
            180                 185                 190

His Gln His Gln Gln Met Ala Pro Ser Thr Leu Ser Gln Gln Asn
            195                 200                 205

His Pro Thr Gln Asn Pro Pro Ala Gly Leu Met Ser Met Pro Asn Ala
            210                 215                 220

Leu Thr Thr Gln Gln Gln Gln Gln Lys Leu Arg Leu Gln Arg Ile
225                 230                 235                 240

Gln Met Glu Arg Glu Arg Ile Arg Met Arg Gln Glu Glu Leu Met Arg
                245                 250                 255

Gln Glu Ala Ala Leu Cys Arg Gln Leu Pro Met Glu Ala Glu Thr Leu
            260                 265                 270

Ala Pro Val Gln Ala Ala Val Asn Pro Pro Thr Met Thr Pro Asp Met
            275                 280                 285

Arg Ser Ile Thr Asn Asn Ser Ser Asp Pro Phe Leu Asn Gly Gly Pro
290                 295                 300

Tyr His Ser Arg Glu Gln Ser Thr Asp Ser Gly Leu Gly Leu Gly Cys
305                 310                 315                 320

Tyr Ser Val Pro Thr Thr Pro Glu Asp Phe Leu Ser Asn Val Asp Glu
            325                 330                 335

Met Asp Thr Gly Glu Asn Ala Gly Gln Thr Pro Met Asn Ile Asn Pro
            340                 345                 350

Gln Gln Thr Arg Phe Pro Asp Phe Leu Asp Cys Leu Pro Gly Thr Asn
            355                 360                 365

Val Asp Leu Gly Thr Leu Glu Ser Glu Asp Leu Ile Pro Leu Phe Asn
370                 375                 380

Asp Val Glu Ser Ala Leu Asn Lys Ser Glu Pro Phe Leu Thr Trp Leu
385                 390                 395                 400

<210> SEQ ID NO 2
<211> LENGTH: 504
<212> TYPE: PRT
<213> ORGANISM: Homo sapiens

<400> SEQUENCE: 2

Met Asp Pro Gly Gln Gln Pro Pro Pro Gln Pro Ala Pro Gln Gly Gln
1               5                   10                  15

Gly Gln Pro Pro Ser Gln Pro Pro Gln Gly Gln Gly Pro Pro Ser Gly
            20                  25                  30

Pro Gly Gln Pro Ala Pro Ala Ala Thr Gln Ala Ala Pro Gln Ala Pro
            35                  40                  45

Pro Ala Gly His Gln Ile Val His Val Arg Gly Asp Ser Glu Thr Asp
            50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
            100                 105                 110

Gly Thr Ala Gly Ala Leu Thr Pro Gln His Val Arg Ala His Ser Ser
```

```
            115                 120                 125
Pro Ala Ser Leu Gln Leu Gly Ala Val Ser Pro Gly Thr Leu Thr Pro
    130                 135                 140
Thr Gly Val Val Ser Gly Pro Ala Ala Thr Pro Thr Ala Gln His Leu
145                 150                 155                 160
Arg Gln Ser Ser Phe Glu Ile Pro Asp Asp Val Pro Leu Pro Ala Gly
                165                 170                 175
Trp Glu Met Ala Lys Thr Ser Ser Gly Gln Arg Tyr Phe Leu Asn His
            180                 185                 190
Ile Asp Gln Thr Thr Thr Trp Gln Asp Pro Arg Lys Ala Met Leu Ser
        195                 200                 205
Gln Met Asn Val Thr Ala Pro Thr Ser Pro Val Gln Gln Asn Met
    210                 215                 220
Met Asn Ser Ala Ser Gly Pro Leu Pro Asp Gly Trp Glu Gln Ala Met
225                 230                 235                 240
Thr Gln Asp Gly Glu Ile Tyr Tyr Ile Asn His Lys Asn Lys Thr Thr
                245                 250                 255
Ser Trp Leu Asp Pro Arg Leu Asp Pro Arg Phe Ala Met Asn Gln Arg
            260                 265                 270
Ile Ser Gln Ser Ala Pro Val Lys Gln Pro Pro Leu Ala Pro Gln
        275                 280                 285
Ser Pro Gln Gly Val Met Gly Gly Ser Asn Ser Asn Gln Gln Gln
    290                 295                 300
Gln Met Arg Leu Gln Gln Leu Gln Met Glu Lys Glu Arg Leu Arg Leu
305                 310                 315                 320
Lys Gln Gln Glu Leu Leu Arg Gln Ala Met Arg Asn Ile Asn Pro Ser
                325                 330                 335
Thr Ala Asn Ser Pro Lys Cys Gln Glu Leu Ala Leu Arg Ser Gln Leu
            340                 345                 350
Pro Thr Leu Glu Gln Asp Gly Gly Thr Gln Asn Pro Val Ser Ser Pro
        355                 360                 365
Gly Met Ser Gln Glu Leu Arg Thr Met Thr Thr Asn Ser Ser Asp Pro
    370                 375                 380
Phe Leu Asn Ser Gly Thr Tyr His Ser Arg Asp Glu Ser Thr Asp Ser
385                 390                 395                 400
Gly Leu Ser Met Ser Ser Tyr Ser Val Pro Arg Thr Pro Asp Asp Phe
                405                 410                 415
Leu Asn Ser Val Asp Glu Met Asp Thr Gly Asp Thr Ile Asn Gln Ser
            420                 425                 430
Thr Leu Pro Ser Gln Gln Asn Arg Phe Pro Asp Tyr Leu Glu Ala Ile
        435                 440                 445
Pro Gly Thr Asn Val Asp Leu Gly Thr Leu Glu Gly Asp Gly Met Asn
    450                 455                 460
Ile Glu Gly Glu Glu Leu Met Pro Ser Leu Gln Glu Ala Leu Ser Ser
465                 470                 475                 480
Asp Ile Leu Asn Asp Met Glu Ser Val Leu Ala Ala Thr Lys Leu Asp
                485                 490                 495
Lys Glu Ser Phe Leu Thr Trp Leu
            500

<210> SEQ ID NO 3
<211> LENGTH: 669
<212> TYPE: PRT
<213> ORGANISM: Homo sapiens
```

```
<400> SEQUENCE: 3

Met Met Arg Leu Arg Gly Ser Gly Met Leu Arg Asp Leu Leu Leu Arg
1               5                   10                  15

Ser Pro Ala Gly Val Ser Ala Thr Leu Arg Arg Ala Gln Pro Leu Val
            20                  25                  30

Thr Leu Cys Arg Arg Pro Arg Gly Gly Gly Arg Pro Ala Ala Gly Pro
        35                  40                  45

Ala Ala Ala Ala Arg Leu His Pro Trp Trp Gly Gly Gly Trp Pro
50                  55                  60

Ala Glu Pro Leu Ala Arg Gly Leu Ser Ser Pro Ser Glu Ile Leu
65                  70                  75                  80

Gln Glu Leu Gly Lys Gly Ser Thr His Pro Gln Pro Gly Val Ser Pro
                85                  90                  95

Pro Ala Ala Pro Ala Ala Pro Gly Pro Lys Asp Gly Pro Gly Glu Thr
            100                 105                 110

Asp Ala Phe Gly Asn Ser Glu Gly Lys Glu Leu Val Ala Ser Gly Glu
        115                 120                 125

Asn Lys Ile Lys Gln Gly Leu Leu Pro Ser Leu Glu Asp Leu Leu Phe
130                 135                 140

Tyr Thr Ile Ala Glu Gly Gln Glu Lys Ile Pro Val His Lys Phe Ile
145                 150                 155                 160

Thr Ala Leu Lys Ser Thr Gly Leu Arg Thr Ser Asp Pro Arg Leu Lys
                165                 170                 175

Glu Cys Met Asp Met Leu Arg Leu Thr Leu Gln Thr Thr Ser Asp Gly
            180                 185                 190

Val Met Leu Asp Lys Asp Leu Phe Lys Lys Cys Val Gln Ser Asn Ile
        195                 200                 205

Val Leu Leu Thr Gln Ala Phe Arg Arg Lys Phe Val Ile Pro Asp Phe
210                 215                 220

Met Ser Phe Thr Ser His Ile Asp Glu Leu Tyr Glu Ser Ala Lys Lys
225                 230                 235                 240

Gln Ser Gly Gly Lys Val Ala Asp Tyr Ile Pro Gln Leu Ala Lys Phe
                245                 250                 255

Ser Pro Asp Leu Trp Gly Val Ser Val Cys Thr Val Asp Gly Gln Arg
            260                 265                 270

His Ser Thr Gly Asp Thr Lys Val Pro Phe Cys Leu Gln Ser Cys Val
        275                 280                 285

Lys Pro Leu Lys Tyr Ala Ile Ala Val Asn Asp Leu Gly Thr Glu Tyr
290                 295                 300

Val His Arg Tyr Val Gly Lys Glu Pro Ser Gly Leu Arg Phe Asn Lys
305                 310                 315                 320

Leu Phe Leu Asn Glu Asp Asp Lys Pro His Asn Pro Met Val Asn Ala
                325                 330                 335

Gly Ala Ile Val Val Thr Ser Leu Ile Lys Gln Gly Val Asn Asn Ala
            340                 345                 350

Glu Lys Phe Asp Tyr Val Met Gln Phe Leu Asn Lys Met Ala Gly Asn
        355                 360                 365

Glu Tyr Val Gly Phe Ser Asn Ala Thr Phe Gln Ser Glu Arg Glu Ser
370                 375                 380

Gly Asp Arg Asn Phe Ala Ile Gly Tyr Tyr Leu Lys Glu Lys Lys Cys
385                 390                 395                 400

Phe Pro Glu Gly Thr Asp Met Val Gly Ile Leu Asp Phe Tyr Phe Gln
```

```
            405                 410                 415
Leu Cys Ser Ile Glu Val Thr Cys Glu Ser Ala Ser Val Met Ala Ala
            420                 425                 430

Thr Leu Ala Asn Gly Gly Phe Cys Pro Ile Thr Gly Glu Arg Val Leu
            435                 440                 445

Ser Pro Glu Ala Val Arg Asn Thr Leu Ser Leu Met His Ser Cys Gly
            450                 455                 460

Met Tyr Asp Phe Ser Gly Gln Phe Ala Phe His Val Gly Leu Pro Ala
465                 470                 475                 480

Lys Ser Gly Val Ala Gly Gly Ile Leu Leu Val Val Pro Asn Val Met
            485                 490                 495

Gly Met Met Cys Trp Ser Pro Pro Leu Asp Lys Met Gly Asn Ser Val
            500                 505                 510

Lys Gly Ile His Phe Cys His Asp Leu Val Ser Leu Cys Asn Phe His
            515                 520                 525

Asn Tyr Asp Asn Leu Arg His Phe Ala Lys Lys Leu Asp Pro Arg Arg
            530                 535                 540

Glu Gly Gly Asp Gln Arg Val Lys Ser Val Ile Asn Leu Leu Phe Ala
545                 550                 555                 560

Ala Tyr Thr Gly Asp Val Ser Ala Leu Arg Arg Phe Ala Leu Ser Ala
            565                 570                 575

Met Asp Met Glu Gln Arg Asp Tyr Asp Ser Arg Thr Ala Leu His Val
            580                 585                 590

Ala Ala Ala Glu Gly His Val Glu Val Val Lys Phe Leu Leu Glu Ala
            595                 600                 605

Cys Lys Val Asn Pro Phe Pro Lys Asp Arg Trp Asn Asn Thr Pro Met
            610                 615                 620

Asp Glu Ala Leu His Phe Gly His His Asp Val Phe Lys Ile Leu Gln
625                 630                 635                 640

Glu Tyr Gln Val Gln Tyr Thr Pro Gln Gly Asp Ser Asp Asn Gly Lys
            645                 650                 655

Glu Asn Gln Thr Val His Lys Asn Leu Asp Gly Leu Leu
            660                 665
```